(12) United States Patent
Sharma et al.

(10) Patent No.: US 7,001,982 B2
(45) Date of Patent: Feb. 21, 2006

(54) NON-NATURAL C-LINKED CARBO-β-PEPTIDES WITH ROBUST SECONDARY STRUCTURES

(75) Inventors: Gangavaram Vasantha Madhava Sharma, Andhra Pradesh (IN); Kondireddi Ravinder Reddy, Andhra Pradesh (IN); Radha Krishna Palakodety, Andhra Pradesh (IN); Ajit Chand Kunwar, Andhra Pradesh (IN); Ravi Sankar Ampapathi, Andhra Pradesh (IN); Jagannadh Bulusu, Andhra Pradesh (IN); Jayaprakash Pagadala, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/403,815

(22) Filed: Mar. 31, 2003

(65) Prior Publication Data

US 2004/0192885 A1    Sep. 30, 2004

(51) Int. Cl.
C07K 1/06    (2006.01)
C07K 2/00    (2006.01)
C07K 5/023   (2006.01)
C07K 7/02    (2006.01)
C07K 9/00    (2006.01)

(52) U.S. Cl. ............ 530/322; 530/332; 530/333; 530/335; 530/337; 530/343; 930/30; 930/290

(58) Field of Classification Search .......... 530/300, 530/322, 332, 333, 335, 337, 343; 930/30, 930/290

See application file for complete search history.

(56) References Cited

U.S. PATENT DOCUMENTS 6,060,585 A * 5/2000 Gellman et al. ............ 530/323
6,617,425 B1 * 9/2003 Seebach .................... 530/329
6,677,431 B1 * 1/2004 DeGrado et al. ........... 530/326

OTHER PUBLICATIONS

Drey et al. Synthesis of Beta-Amino-Acid Peptides . . . Journal of the Chemical Society, Perkins Transactions I. 1973, pp. 2001-2006.*

(Continued)

*Primary Examiner*—Jeffrey Edwin Russel
(74) *Attorney, Agent, or Firm*—Ladas and Parry LLP

(57) ABSTRACT

Nonnatural C-linked carbo-β-peptides with robust secondary structures, which involves the synthesis of a new class of β-peptides called C-linked carbo-β-peptides. The compounds are favorably disposed for the formation of stable helical structures and are useful as biologically active carbo-β-peptides. The new class of β-peptides have the following formula Formula I

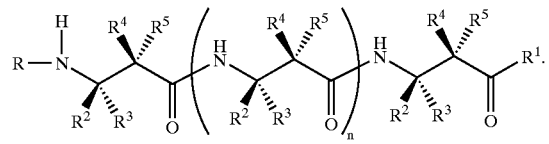

The new class of β-peptides are useful as biologically active molecules to disrupt biological interactions of proteins, for molecular design and to synthesize peptide libraries.

67 Claims, 9 Drawing Sheets

OTHER PUBLICATIONS

Sharma, G., et al., "Robust Mixed 10/12 Helices Promoted by "Alternating Chirality" in a New Family of C-Linked Carbo-beta.-peptides" XP-002300147 *Journal of the American Chemical Society* (2003) vol. 125, No. 45, pp. 13670-13671.

Palomo, C., "Design and Synthesis of a Novel Class of Sugar-Peptide Hybrids . . . " *Journal of the American Chemical Society* (2002) vol. 124, No. 29, pp. 8637-8643, XP009010582.

Jablonkai, I., "New Approach for Preparation of C-Glycoamino Acid Building Blocks" *American Peptide Society* (2001) pp. 52-53, XP009037661.

Sharma, G., et al., "Tetra-n-butylammonium fluoride: an efficient base for aza-Michael addition . . . " *Tetrahedron: Asymmetry* (2002) vol. 13, No. 1, pp. 21-24.

Seebach, D., et al., "Preparation and Structure of beta-Peptides Consisting of Geminally . . . " *Helvetica Chimica Acta* (1998) vol. 81, pp. 2218-2243, XP-001182275.

* cited by examiner

NON-NATURAL C-LINKED CARBO-β-PEPTIDES WITH ROBUST SECONDARY STRUCTURES

FIELD OF THE INVENTION

The present invention relates to Novel nonnatural C-linked carbo-β-peptides with robust secondary structures and process for the preparation of the said compounds.

The said novel β-peptides are derived from the coupling of a variety of C-linked carbohydrate β-amino acids. These β-peptides contain a variety of carbohydrate moieties on the backbone of β-peptide as carbohydrate recognition sites. The thus made β-peptides have shown stable helical structures.

BACKGROUND OF THE WORK

Reference may be made to J. Am. Chem. Soc., 116, 1054–1062 (1994), by Gellman et al, wherein the β- and γ-amino acids were postulated to fold in the same manner as α-amino acids through intramolecular hydrogen bonding.

In 1996, two groups of scientists, one led by Seebach et al and another by Gellman et al reported the first synthesis of β-peptides showing well-defined secondary structures. Reference may be made to Helv. Chim. Acta 79, 913–941 and 2043–2066 (1996), wherein it was the fist group worked on the synthesis of β-hexapeptide consisting of acyclic β-amino acid monomers and explored for the secondary structures along with effects of residue variation on the secondary structures.

Reference may be made to J. Am. Chem. Soc., 118, 13071–72 (1996), wherein Gellman group worked on the synthesis of β-peptides containing a cyclohexane 1,2-amino acid (ACHC) as β-amino acid monomer to derive a 14-helical structure. Reference may further be made to Nature 387, 381 (1997), wherein cyclopentane amino acid (ACPC) gave 12-helical structure.

Reference may be made to Helv. Chim. Acta 81, 932 (1998), wherein Seebach's group worked on $\beta^2$–$\beta^3$ mixed hexapeptide which exhibited a 12/10/12 helix (10/12 helix) while reference may be made to Helv. Chim. Acta. 81, 2218–2243(1998), wherein $\beta^{3,3}$, $\beta^{2,2}$ amino acids and their β-peptides were prepared, while $\beta^{3,3}$ have shown 8-helix.

Reference may be made to Angew. Chem. Int. Ed , 41, 230–253 (2002); Chem. Rev. 102, 491–514 (2002); Chem. Eur. J., 8, 4366–4376 (2002), which reviewed about a new class of 'sugar amino acids' wherein both the acid and amine components are installed on the carbohydrate frame and a variety of α,β,γ,δ,-sugar amino acids were prepared and converted into the corresponding peptides of a variety of secondary structures and biological activities.

OBJECTIVES OF THE INVENTION

The main object of the present invention is to synthesize a new class of C-linked carbo β-peptides.

Other object is to synthesize a new class of β-amino acids having carbohydrate moieties as side chains.

Yet another object is to convert the thus made newer C-linked carbo β-amino acids into the corresponding C-linked carbo β-peptides as a new class of β-peptides.

A further object is to synthesise these new C-linked carbo β-peptides as proteolytically stable peptide molecules.

The other object to synthesise the new class of C-linked carbo β-peptides is to enhance the water solubility and stability.

The objective for the synthesis of these new C-linked carbo β-peptides is to enhance the carbohydrate recognition sites in the peptides thus made.

Another object is to enhance the activity of the thus made peptides for their biological profile and develop them into anti-cancer, anti-microbial and other therapeutic class agents.

Another object of the present invention provides novel processes for the synthesis of said novel β-amino acids and β-peptides that would exhibit interesting biological activity. These synthetic process routes utilize commercial reagents and facilitate large scale preparation, and provide the new class of C-lined carbo β-peptides in sufficient quantities for further biological evaluation.

Another object of the present invention is to use chirality as the controlling point in giving stable secondary structures. C-Linked carbo β-amino acids, epimeric at the amine center for making the C-linked carbo β-peptides having stable secondary structures.

Other object of the present invention is to synthesize C-linked β-peptides with C-linked carbo β-amino acid with D configuration, C-linked β-amino acids with L-configuration and mixed peptides with D and L-C-linked carbo-β-amino acids.

SUMMARY OF THIS INVENTION

Figure 1:
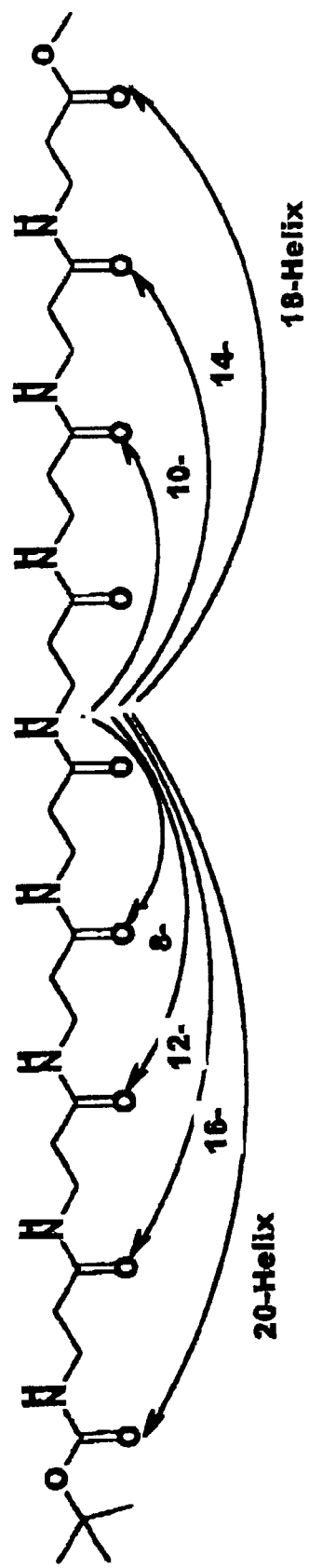
FIG. 1 represents the structure of poly β-alanine, wherein the hydrogen bonding is depicted indicating a variety of helical structures possible.
Figure 2:
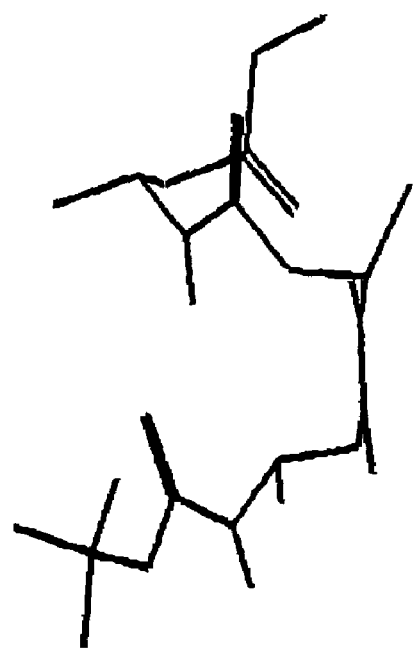
FIG. 2 represents Circular Dichroism (CD) plot for 43 in MeOH and its simulated model, where sugar is replaced with methyl for clarity and clear visualization.
Figure 2:
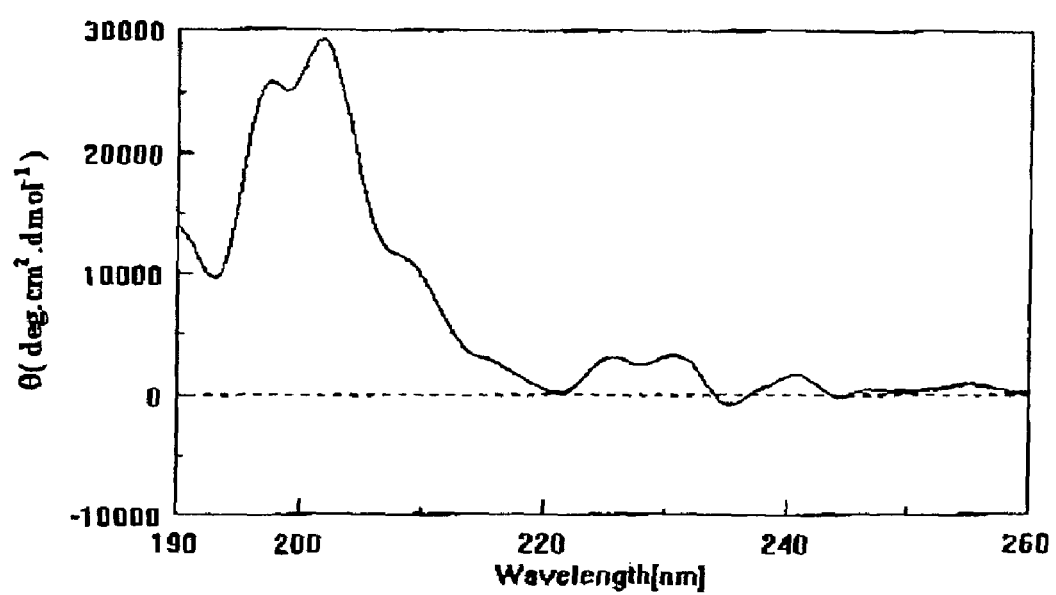

Accordingly the present invention provides Novel non-natural C-linked carbo-β-peptides with robust secondary structures, which comprises of the synthesis of a new class of β-peptides called C-linked carbo-β-peptides, most of which are favorably disposed for the formation of stable helical structures.

In an embodiment of the present invention, it would be desirable to synthesize new class of β-peptides, since the β-amino acids are part structures of several biologically active compounds.

In another embodiment of the present invention it deals with the synthesis of C-linked carbo β-amino acids since several sugar amino acids are part structures of biologically active compounds.

In yet another embodiment these new β-peptides, having carbohydrate moieties, would find immense use as biologically active carbo-β-peptides, the rationale for the synthesis of such new class of C-linked carbo β-peptides is to derive small bioactive peptides reported in this invention are as below:

1) β-peptides derived from β-amino acids unlike peptides from α-amino acids are metabolically more stable, since they are non-natural.
2) The β-peptides thus made in this invention due to the presence of carbohydrate structures would act as recognition sites.
3) The presence of carbohydrate moieties on the β-peptide chain would enhance the solubilities of these peptides tremendously, thereby facilitating the transportation.
4) The β-peptides thus made from C-linked carbo β-amino acids would impart a high degree of amphiphilicity due to the hydrophilic nature of the β-peptides.
5) The β-peptides with C-linked carbo β-amino acids thus made would show their peptide activity and can possess other favorable characters which are imparted such as enzymatic stability and transport profiles.
6) The β-peptides thus made from C-linked carbo β-amino acids due to the presence of both the carbohydrate and peptide moieties in their skeletons, would enhance the process of peptide based drug discovery, devoid of the problems associated with solubilities of peptide based active compounds. In addition, it imparts the proteolytic tolerance to these compounds.

DETAILED DESCRIPTION OF THE INVENTION

The present invention is related to the synthesis of C-linked carbo-β-peptides. Some of which favor the formation of novel helical secondary structures such as 12, 14 or 10/12 helices. The presence of carbohydrate moiety on the β-peptide backbone is desirable since, it helps not only as sugar recognition center in the new β-peptides, but also attributes amphiphilicity due to hydrophilic nature.

The synthetic protocol developed in the present invention is suitable for the synthesis of β-peptides with the following formula I.

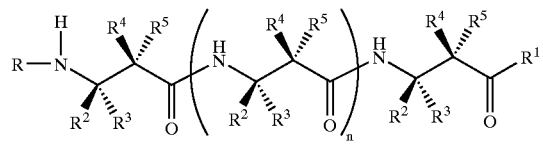

Formula I n=0, 1, 2, 3 . . .

R=H, Boc, Cbz, Fmoc, acetyl or salts such as HCl, TFA and others $R^1$=—O alkyl, —O-aralkyl, -amine, alkylamine, aryalkyl maine $R^2=R^3=R^4=R^5$=H $R^2$=sugar or hydroxy alkyl, amino alkyl/thioalkyl, $R^3=R^4=R^5$=H $R^3$=sugar or hydroxy alkyl, amino alkyl/thioalkyl, $R^2=R^4=R^5$=H $R^4$=sugar or hydroxy alkyl, amino alkyl/thioalkyl, $R^2=R^3=R^5$=H $R^5$=sugar or hydroxy alkyl, amino alkyl/thioalkyl, $R^2=R^3=R^4$=H $R^2=R^4$=sugar or hydroxy alkyl, amino alkyl/thioalkyl, $R^3=R^5$=H $R^3=R^5$=sugar or hydroxy alkyl, amino alkyl/thioalkyl, $R^2=R^4$=H $R^2=R^5$=sugar or hydroxy alkyl, amino alkyl/thioalkyl, $R^3=R^4$=H $R^3=R^4$=sugar or hydroxy alkyl, amino alkyl/thioalkyl, $R^2=R^5$=H $R^2=R^3$=sugar or hydroxy alkyl, amino alkyl/thioalkyl, $R^4=R^5$=H $R^4=R^5$=sugar or hydroxy alkyl, amino alkyl/thioalkyl, $R^2=R^3$=H Sugars can be monosaccharide pentoses such as D-xylo, D-ribo, D-lyxo, D-ara or the L-sugars such as L-xyl, L-rib, L-lyxo, L-ara in furanoside or pyranoside form; hexoses such as D-and L-glc, D-and L-gal, D-and L-man, D-and L-gul, D-and L-all, etc. in furanoside/pyranoside form; disaccharides such as lactose, maltose, cellobiose etc.; fully protected as acetates, benzoates, allyl or aralkyl ethers, alkylidene dioxolane derivatives, thio derivatives or totally unprotected sugars, D and L sugars in furanoside/pyranoside form having heterocyclic bases such as adenine, guanine, thymidine, cytosine or unnatural bases or heterocyclics having one or more than one heteroatoms such as O/N/S both in 5 and 6 membered rings, dexoy sugars/amino sugars natural/non-natural, rare sugars and higher sugars, bifunctional sugar amino acids The present invention provides a new class of C-linked carbo β-peptides having basic structure as depicted in structural formula I.

The main advantage of the present invention is that it allows the construction of C-linked carbo β-peptides hitherto unknown class, with secondary structures of high stability, the formation of the proposed secondary structures is well controlled through the variation of chirality at the a e bearing carbon stereo centre of C-linked β-amino acid monomer. Since these unnatural β-peptides can be synthesized with well defined and stable secondary structures, they can mimic the secondary structures of natural protein and thereby disrupt the biological interactions of biopolymers (proteins). Since, these peptides adopt stable secondary structures through chirality control, they are well suited for molecular design. Further to the invention, the C-linked carbo β-peptides are useful as base molecules to synthesize an array of peptide libraries with varying the sequence of β-amino acid carbohydrate moieties, functional groups and the like. Since the chirality plays a prominent role in deriving the secondary structures altering the substituent accordingly do not substantially disturb the secondary structures thus can be advantageously utilized to build vast array of C-linked carbo β-peptide with a wide variety of substituents with a similar stable secondary structures in solution.

Figure 3:
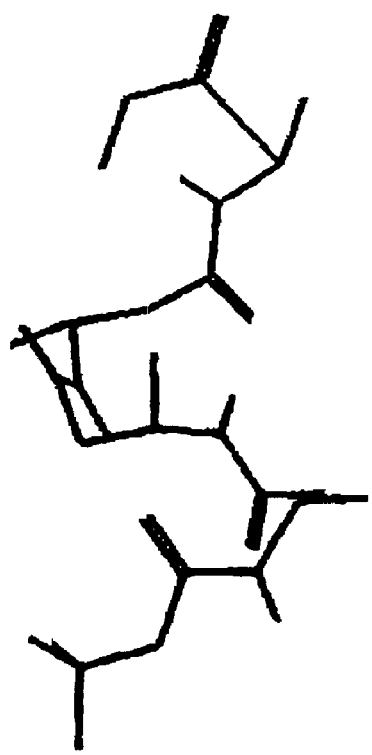
FIG. 3 represents Circular Dichroism (CD) plot for 38 in MeOH and its simulated model, where sugar is replaced with methyl for clarity and clear visualization.
Figure 3:
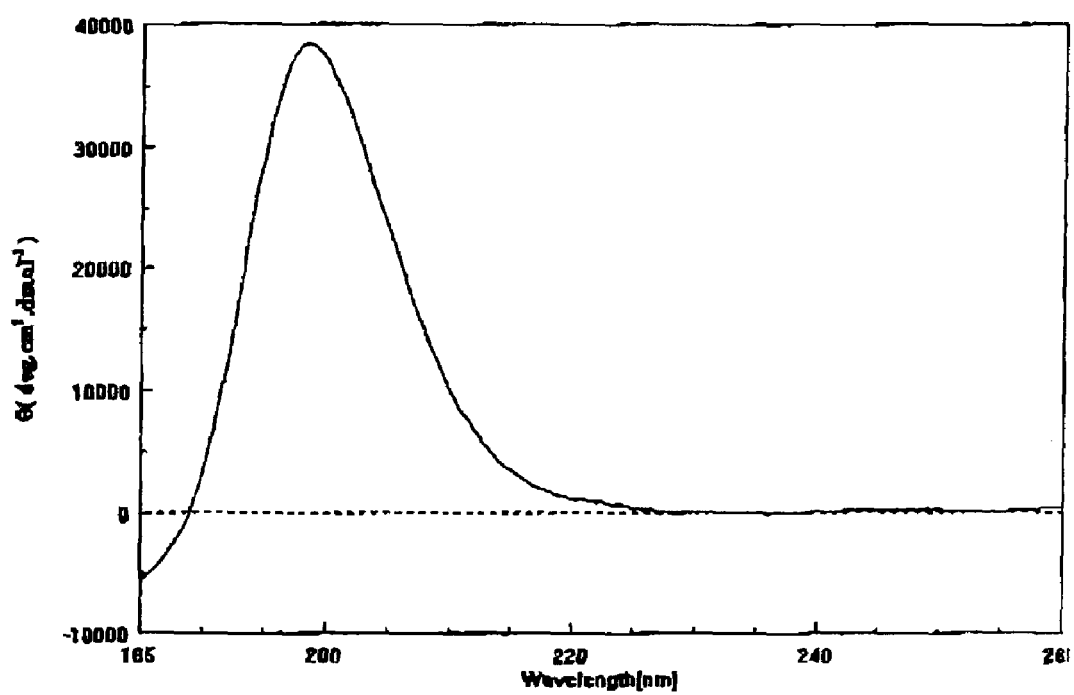
Figure 4:
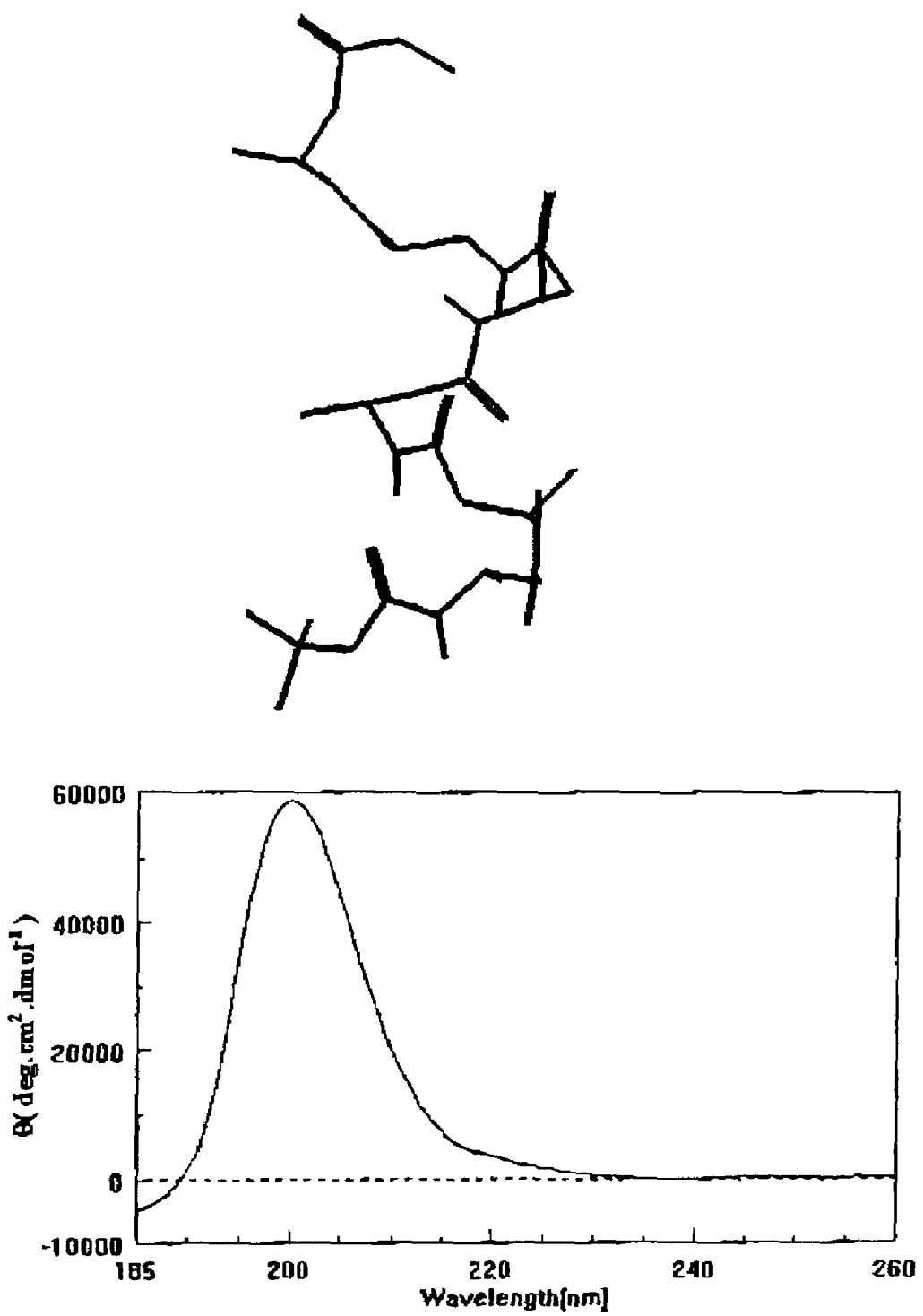
FIG. 4 represents Circular Dichroism (CD) plot for 41 in MeOH and its simulated model, where sugar is replaced with methyl for clarity and clear visualization.
Figure 5:
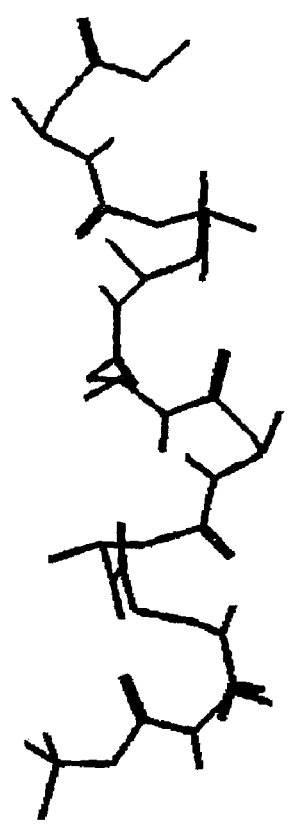
FIG. 5 represents Circular Dichroism (CD) plot for 42 in MeOH and its simulated model, where sugar is replaced with methyl for clarity and clear visualization.
Figure 5:
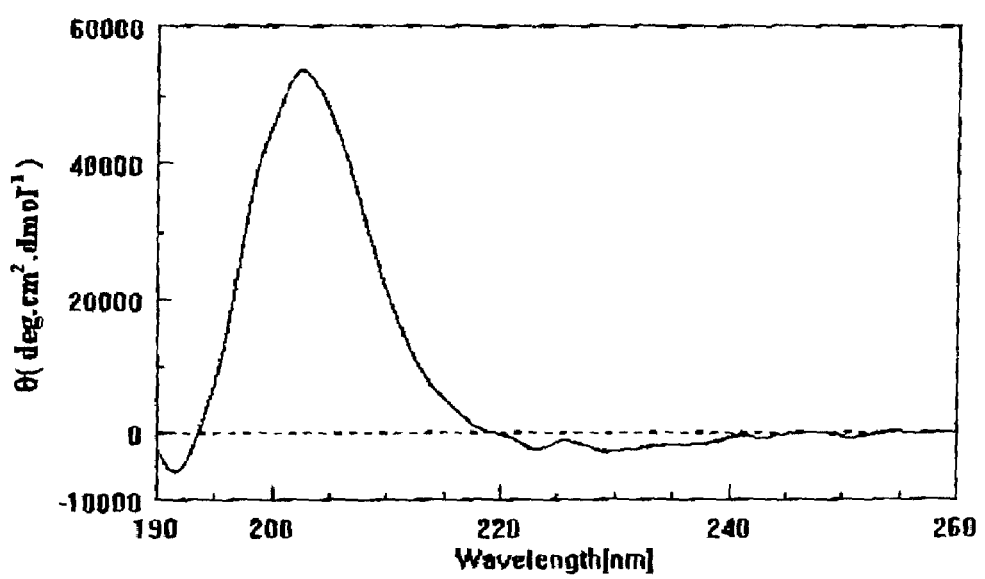
Figure 6:
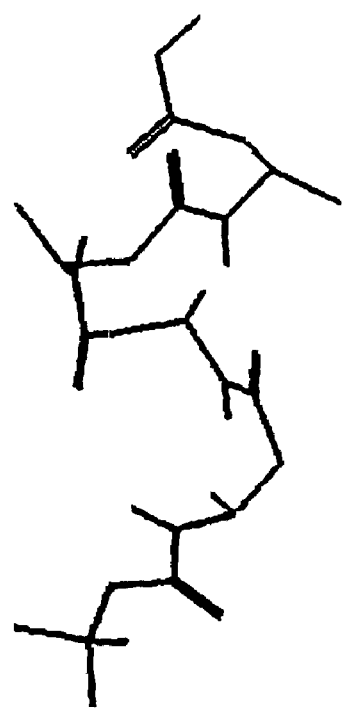
FIG. 6 represents Circular Dichroism (CD) plot for 23 in MeOH and its simulated model, where sugar is replaced with methyl for clarity and clear visualization.
Figure 6:
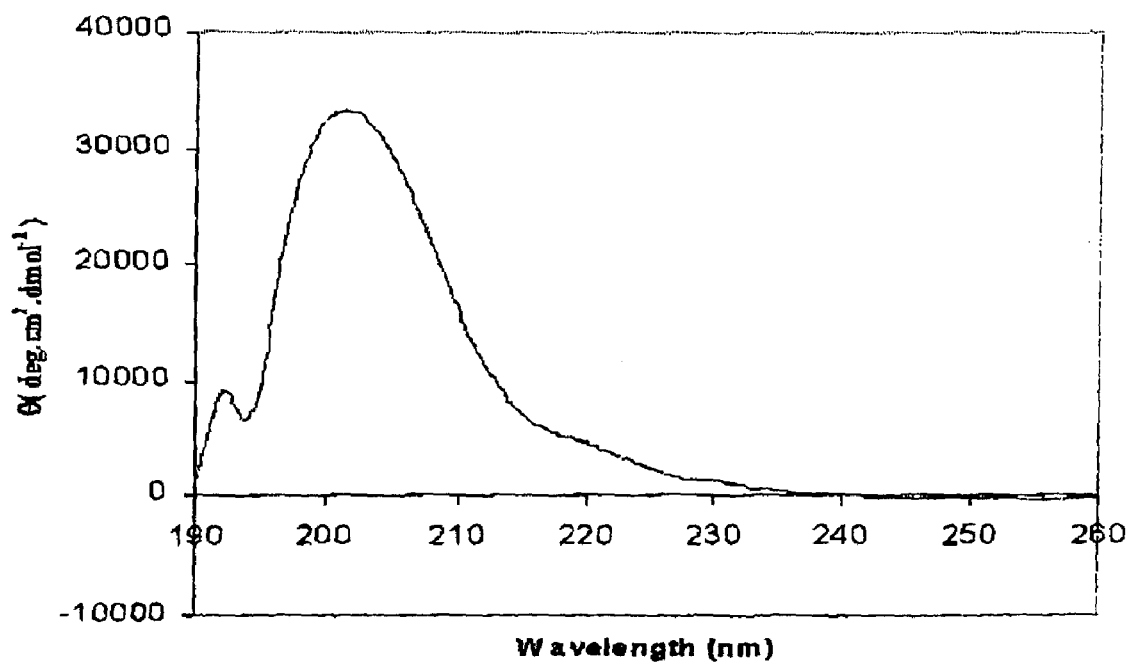
Figure 7:
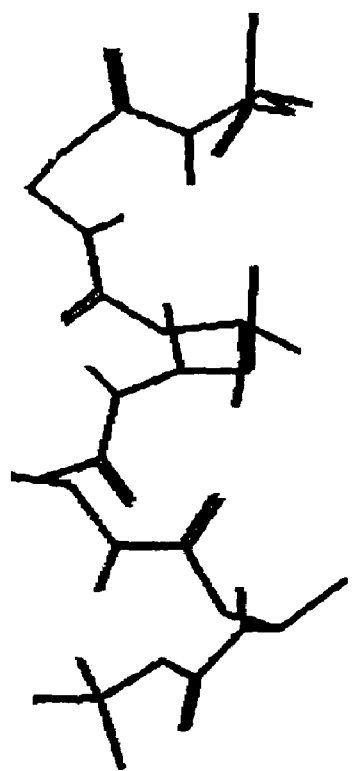
FIG. 7 represents Circular Dichroism (CD) plot for 26 in MeOH and its simulated model, where sugar is replaced with methyl for clarity and clear visualization.
Figure 7:
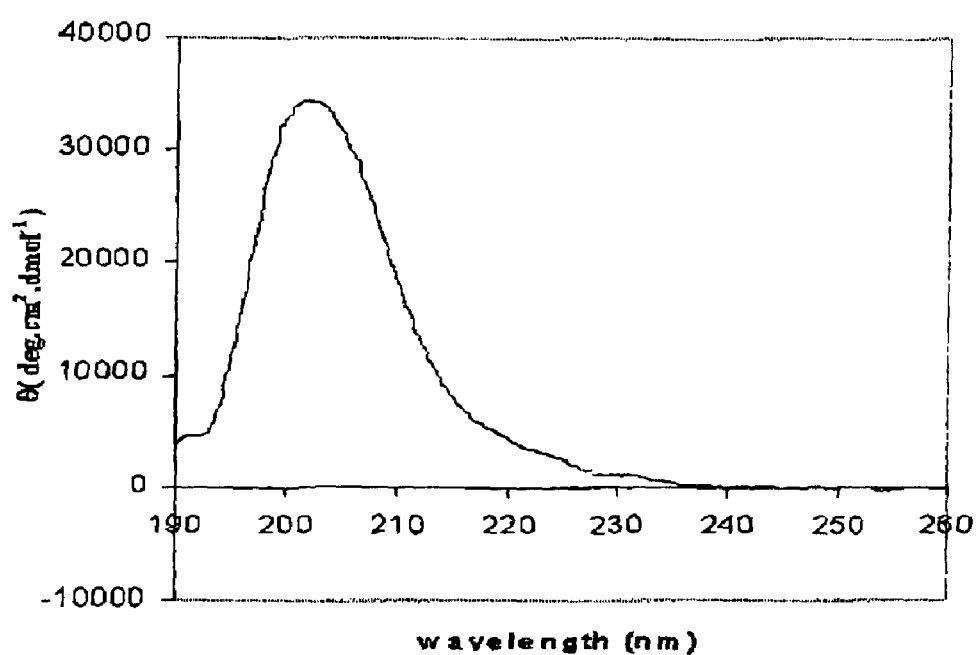
Figure 8:
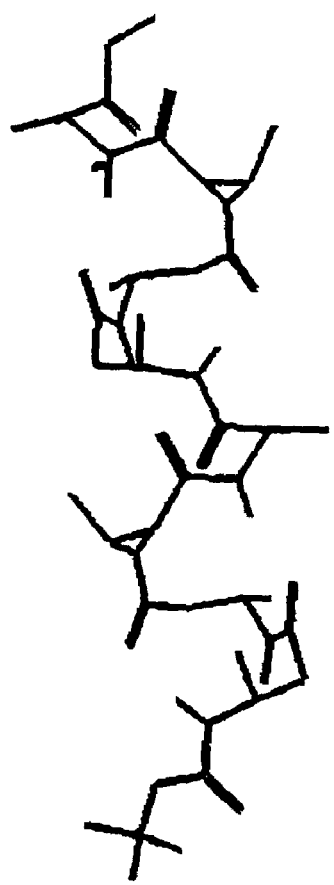
FIG. 8 represents Circular Dichroism (CD) plot for 27 in MeOH and its simulated model, where sugar is replaced with methyl for clarity and clear visualization.
Figure 8:
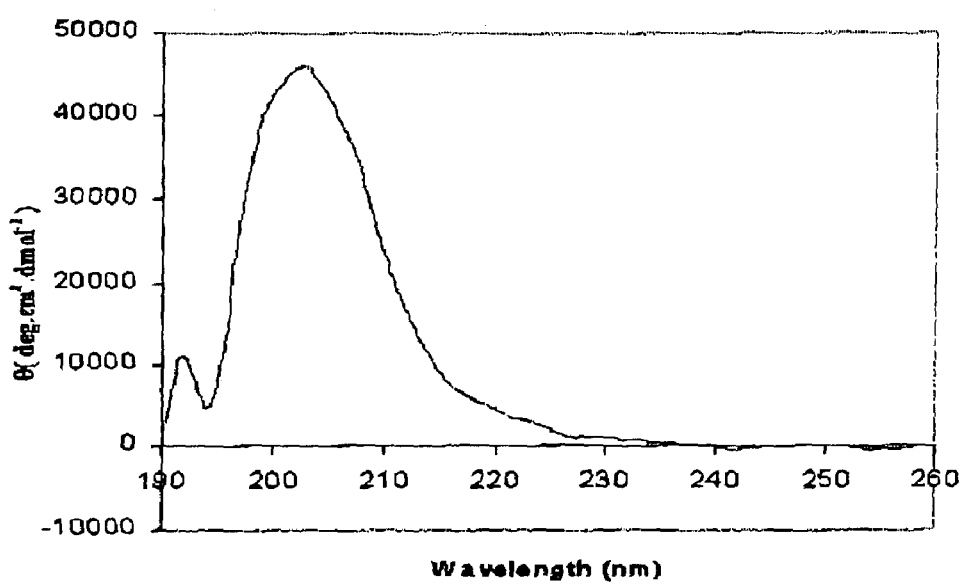
Figure 9:
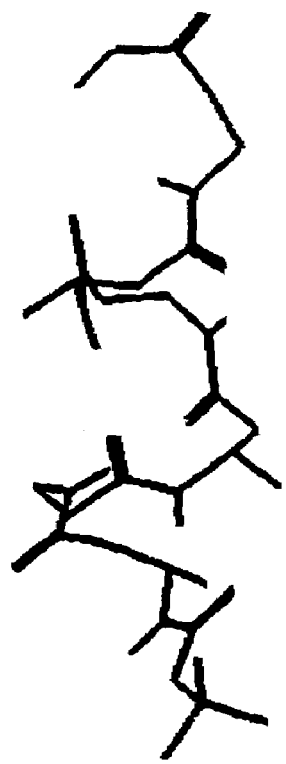
FIG. 9 represents Circular Dicbroism (CD) plot for 52 in MeOH and its simulated model, where sugar is replaced with methyl for clarity and clear visualization.
Figure 9:
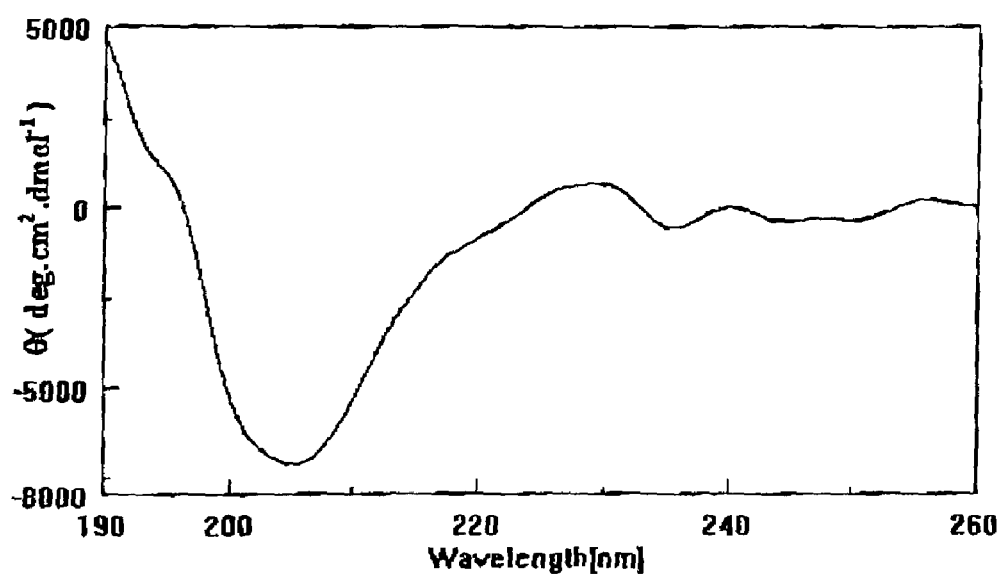

Helices in β-peptides: Initial molecular model studies indicated that oligomers of β-amino acid (β-peptides) are well suited for adoption of compact secondary structures stabilized by intramolecular hydrogen bonds. FIG. 6 shows the hydrogen bonds that define the helices obtained for a tetrapeptide. These are referred to as 10/12/10 helices, (10, 12, 10 refer to the number of bonds between the hydrogen bonding atoms) nomenclature was derived from N-terminal amide hydrogen towards the C-terminal carbonyl group. The tetrapeptide in FIG. 3 has been shown to adopt a 12/10 helical structure with intertwined hydrogen bonded secondary structure. The rigidity of the structure is due to the stereochemical and electronic contributing aspects of the sugar moiety in the tetrapeptide. The incorporation of the sugar motifs in the backbone carbon of β-amino acid provide not only substantial bulkyness but also helps in assembly of very small peptides, even trimers/tetramers, display secondary structure.

Schemes 1 and 2 exemplify as preferred preparative method of the invention that provide the amino acid monomers 3 to 10. The aldehyde 1 was converted to α, β-unsaturated ester 2 example 1, part 1. Michael addition reaction on 2 with benzyl amine, dibenzyl amine and other amines of the like under basic conditions such as TBAF, DBU, DBN, Hunig's base, triethyl amine or other suitable organic bases or metal alkoxides in suitable solvents such as THF or other solvents to get the β-amino acid 3 (Tetrahedron: Asymm. (2002) 13, 21–24). See example 1, part 2 method A, for exemplary reaction conditions. The compound thus reported in the invention is a single enantiomer. For generation of 4 a related approach as reported was adopted, for instance (J. Org. Chem. 2001, 16, 1065) to get the mixture of 3 and 4, according to the conditions exemplified in example 1, part 2 method B.

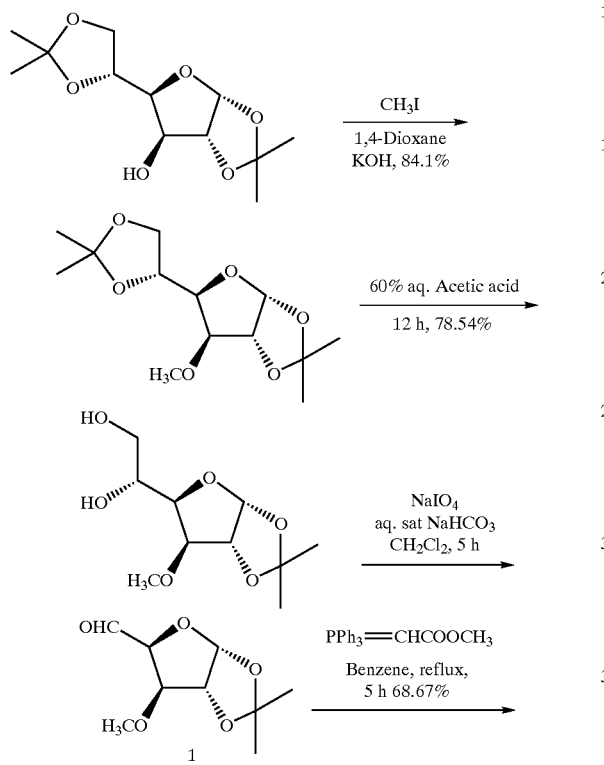

-continued

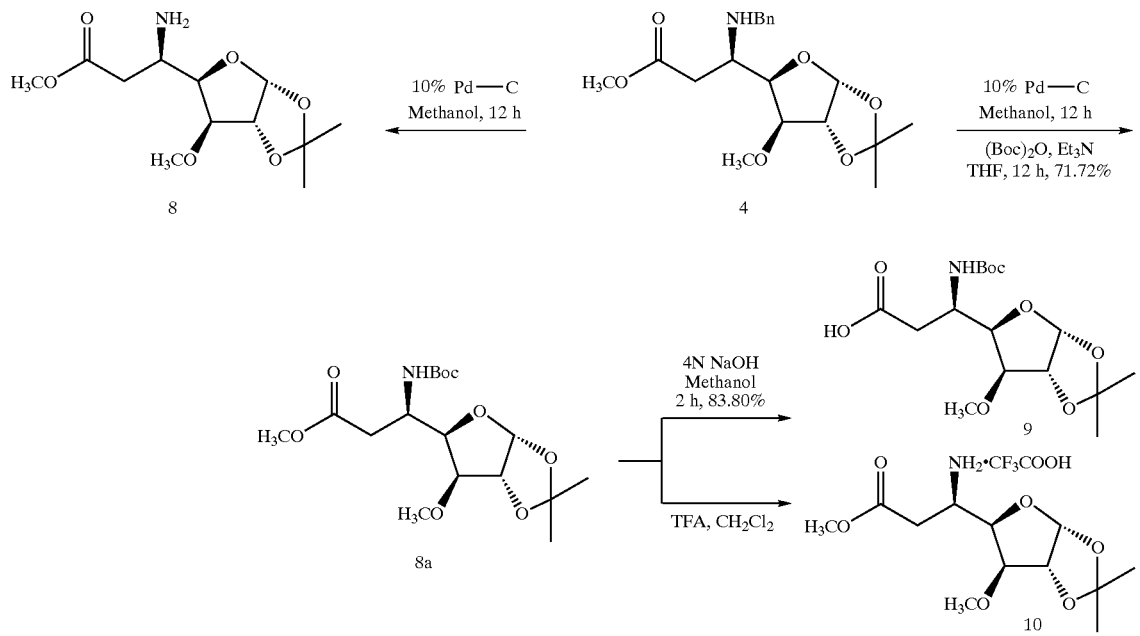

The amino acids represented by the formula 3 and 4 are subjected to hydrogenolysis in presence of Pd—C in suitable solvents such as methanol under hydrogen atmosphere to give 5 and 8 respectively as exemplified in example 1, part 3 and part 5 respectively, which were used as such for further reactions, As exemplified in example 1, part 3 and part 7, 3 and 4 are subjected to catalytic hydrogenation and subsequently with out isolation exposed to (Boc)$_2$O under basic conditions like triethyl amine in suitable solvents like THF or any other preferential solvents to result in 5a and 8a, under the conditions exemplified in example 1, part 4 and part 8 respectively. Compounds 5a and 8a further on hydrolysis under basic conditions with the use of a base like NaOH, LiOH with a suitable normality in preferred solvents like MeOH or otherwise to result in 6 and 9 as exemplified in example 1, part 5 and part 9 respectively for the detailed experimental description. Likewise compounds 5a and 8a were exposed to acids like TFA and the like in solvents for eg; CH$_2$Cl$_2$ and the like to provide compounds of formula 7 and 10 respectively as exemplified in example, part 6 and part 10 respectively, Synthesis of Peptides Using (S)-Amino Acids Scheme 3 exemplifies a preferred preparative method of the invention that provides compounds of formula 11, 14, 17, 18 and 19 representing di, tetra, hexa, octa and tri C-linked carbo β-peptides. Thus in scheme 3, the monomers 5 and 6 are coupled by conventional reagents such as dicyclohexyl carbodiimide/N-hydroxy succinimide (DCC/HoBt) or 1-ethyl-3-(3'-dimethyl amino prepyl) carbodiimide hydrochloride/N-hydroxy benztriazole (EDCI/HOBt) in solvent phase coupling procedures (see, example Bodanszky, M-; Bodanszky, A. The practice of peptide synthesis; Springer Verlag; New York, 1984) in suitable solvents such as CH$_2$Cl$_2$ to result in a dideptide 11. For exemplary reaction conditions for the preparation of 11 see example 2, part 1.

Dipeptide 11 was treated with an organic acid like TFA and the like in suitable solvents for eg; CH$_2$Cl$_2$ and the like to provide salt 12 as exemplified in example, 2, part 2. Similarly 11 was also subjected to base induced hydrolysis in presence of suitable base like NaOH and the like in acceptable solvents like MeOH to finish an unprotected acid 13. For detailed experimental discussion see example 2, part 3. Further synthesis of a tetrapeptide was achieved upon coupling of 12 and 13 in presence of conventional reagents like EDCI/HOBt/DIPEA in suitable solvents for eg; Cl$_2$Cl$_2$ to yield 14 as exemplified in example 2, part 4. Tetrapeptide 14 was subsequently converted to free acid 15 under basic hydrolysis conditions with conventional reagents like NaOH in methanol. See example 2, part 5. Also 14 was further exposed to TFA in CH$_2$Cl$_2$ to deblock the Boc protecting group and the same was isolated as TFA salt 16, as exemplified in example 2, part 6.

Scheme 3

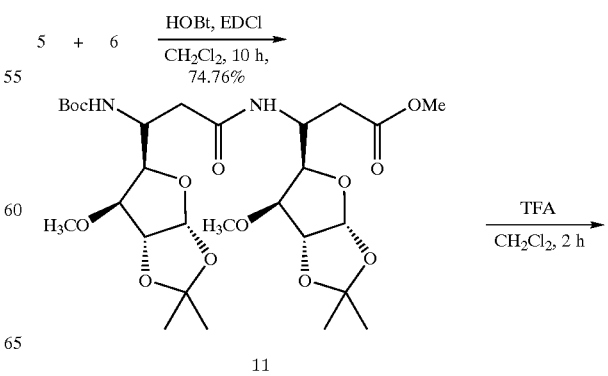

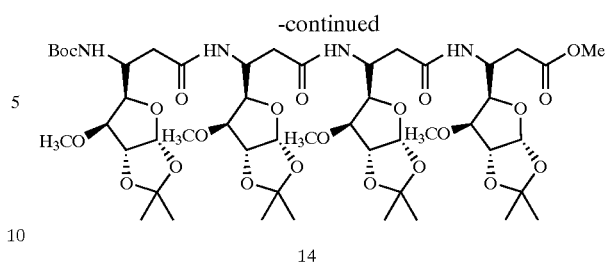

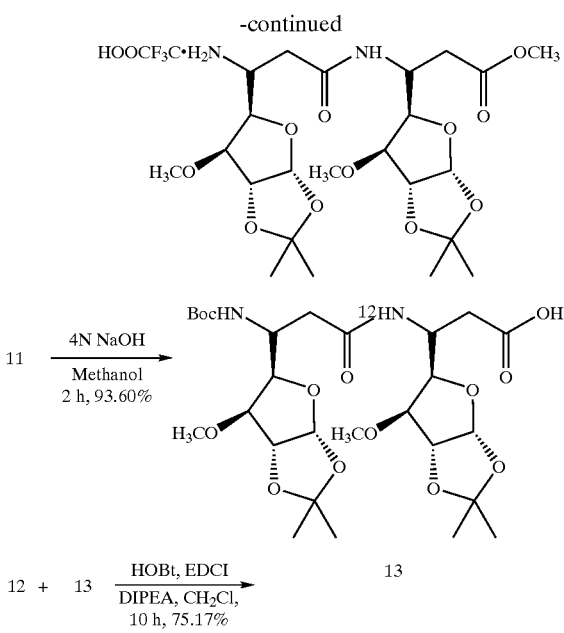

Further preparative methods of other oligomers is depicted in Scheme 3. For eg; coupling of 15 with 12 under the above standard reaction conditions (EDCI/HOBt/DIPEA, CH$_2$Cl$_2$, DMF) resulted in the hexapeptide 17. For experimental conditions see example 2, part 7. Similarly coupling of 15 with 16 under the conventional peptide coupling reaction conditions as described above, with EDCI in presence of solvents like CH$_2$Cl$_2$:DMF in ratio as suitable enough for the reaction to result in the product octamer 18, as exemplified in example 2 part 8.

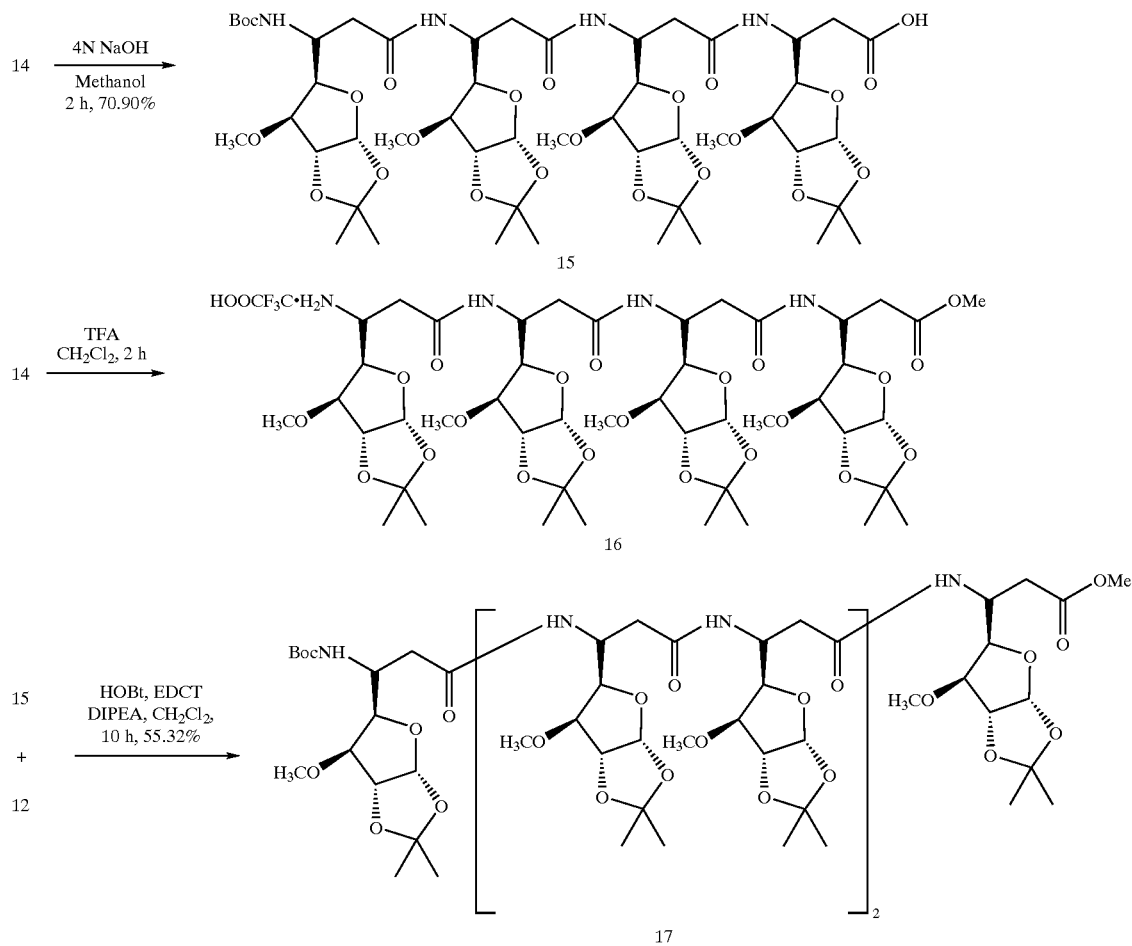

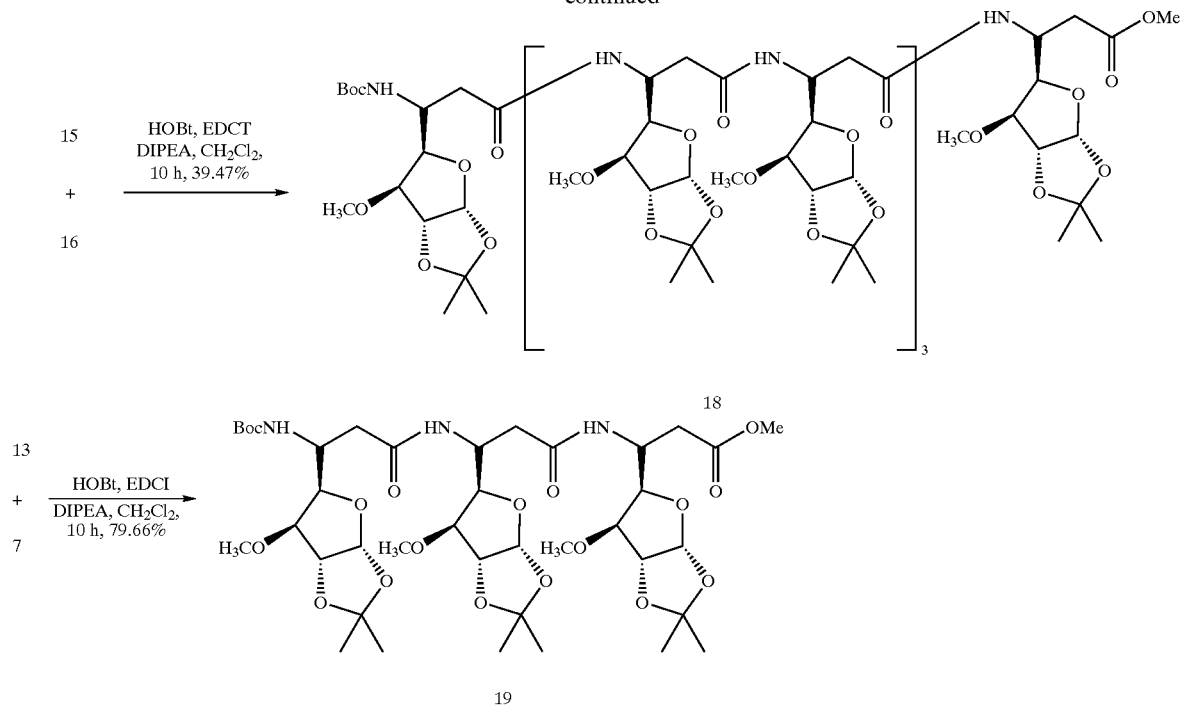

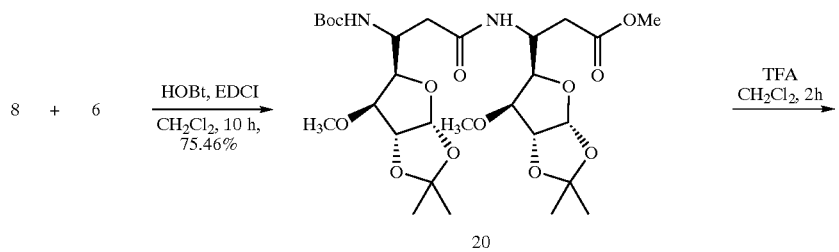

A similar preparative description was made use for the preparation of tri peptide 19 from 13 and 7, under the above said reaction conditions of EDCI/HOBt in solvents conventionally used in peptide coupling such as CH$_2$Cl$_2$, as exemplified in example 2 part 9.

Synthesis of Peptides Using S and R Amino Acids

Scheme 4 exemplifies a preferred preparative method of the invention that provides compounds of formula 20, 23, 26, 27 and 28 representing di, tetra, hexa, octa and tri C-linked carbo β-peptides. Thus in Scheme 4, the monomers 8 and 6 are coupled by conventional reagents such as dicyclohexyl carbodiimide/N-hydroxy succinimide

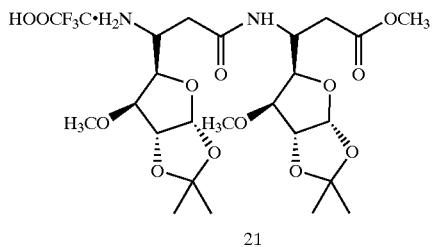

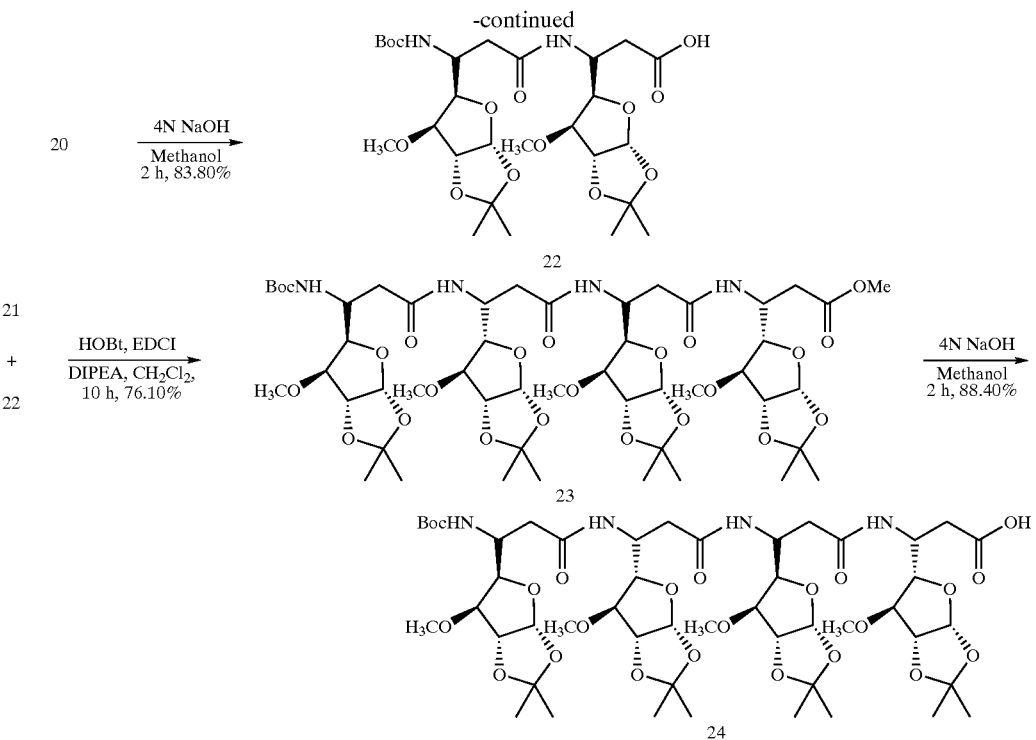

(DCC/HoBt) or 1-ethyl-3-(3'-dimethyl amino prepyl) carbodiimide hydrochloride/N-hydroxy benztriazole (EDCI/HOBt) in solvent phase coupling procedures (see, example Bodanszky, M-; Bodanszky, A. The practice of peptide synthesis; Springer Verlag; New York, 1984) in suitable solvents such as $CH_2Cl_2$ to result in a dideptide 20. For exemplary reaction conditions for the preparation of 20 see example 3, part 1.

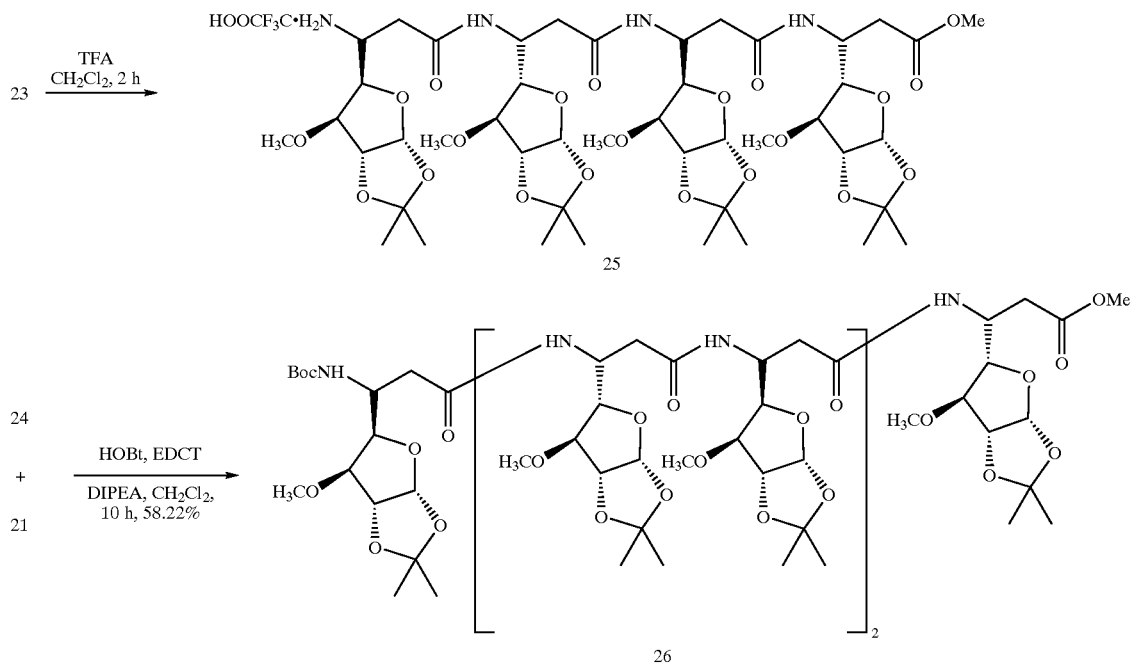

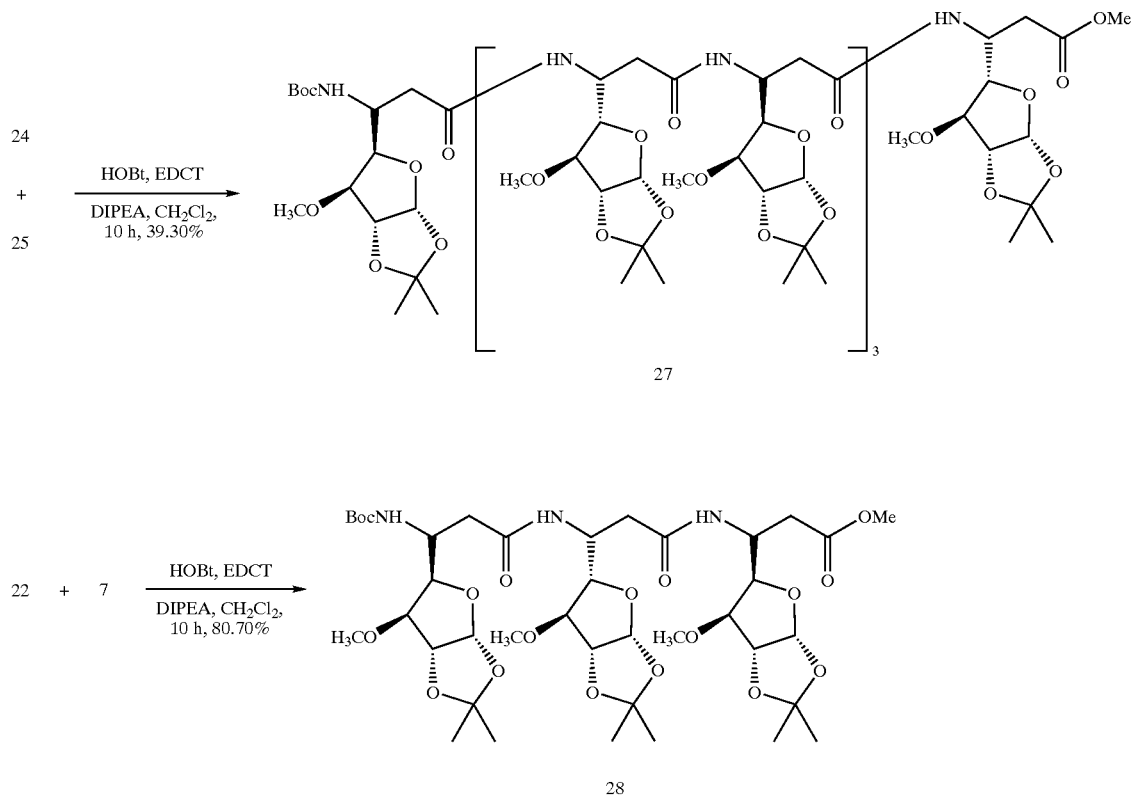

Dipeptide 20 was treated with an organic acid like TFA and the like in suitable solvents for eg; $CH_2Cl_2$ and the like to provide salt 21 as exemplified in example 3, part 2. Similarly 20 was also subjected to base induced hydrolysis in presence of suitable base like NaOH and the like in acceptable solvents like MeOH to furnish an unprotected acid 22. For detailed experimental discussion see example 3, part 3.

Further synthesis of a tetrapeptide was achieved upon coupling of 21 and 22 in presence of conventional reagents like EDCI/HOBt/DIPEA in suitable solvents for eg; $CH_2Cl_2$ to yield 23 as exemplified in example 3, part 4. Tetrapeptide 23 was subsequently converted to free acid 24 under basic hydrolysis conditions with conventional reagents like NaOH in methanol. See example 3, part 5. Also 23 was further exposed to TFA in $CH_2Cl_2$ to deblock the Boc protecting group and the same was isolated as TFA salt 25, as exemplified in example 3, part 6.

Further preparative methods of other oligomers is depicted in Scheme 4. For eg; coupling of 24 with 21 under the above standard reaction conditions (EDCI/HOBt/DIPEA, $CH_2Cl_2$, DMF) resulted in the hexapeptide 26. For experimental conditions see example 3, part 7. Similarly coupling of 24 with 25 under the conventional peptide coupling reaction conditions as described above, with EDCI in presence of solvents like $CH_2Cl_2$:DMF in ratio as suitable enough for the reaction to result in the product octamer 27, as exemplified in example 3 part 8.

A similar preparative description was made use for a the preparation of tri peptide 28 fom 22 and 7, under the above said reaction conditions of EDCI/HOBt in solvents conventionally used in peptide coupling such as $CH_2Cl_2$, as exemplified in example 3 part 9.

Synthesis of Peptides from R Amino Acids

Scheme 5 exemplifies a preferred preparative method of the invention that provides compounds of formula 29, 32 and 34 representing di, tetra and hexa C-linked carbo β-peptides. Thus in Scheme 5, the monomers 8 and 9 are coupled by conventional reagents such as dicyclohexyl carbodiimide/N-hydroxy succinimide (DCC/HoBt) or 1-ethyl-3-(3'-dimethyl amino prepyl) carbodiimide hydrochloride/N-hydroxy benztriazole (EDCI/HOBt) in solvent phase coupling procedures (see, example Bodanszky, M-; Bodanszky, A. The practice of peptide synthesis; Springer Verlag; New York 1984) in suitable solvents such as $CH_2Cl_2$ to result in a dideptide 29. For exemplary reaction conditions for the preparation of 29 see example 4, part 1.

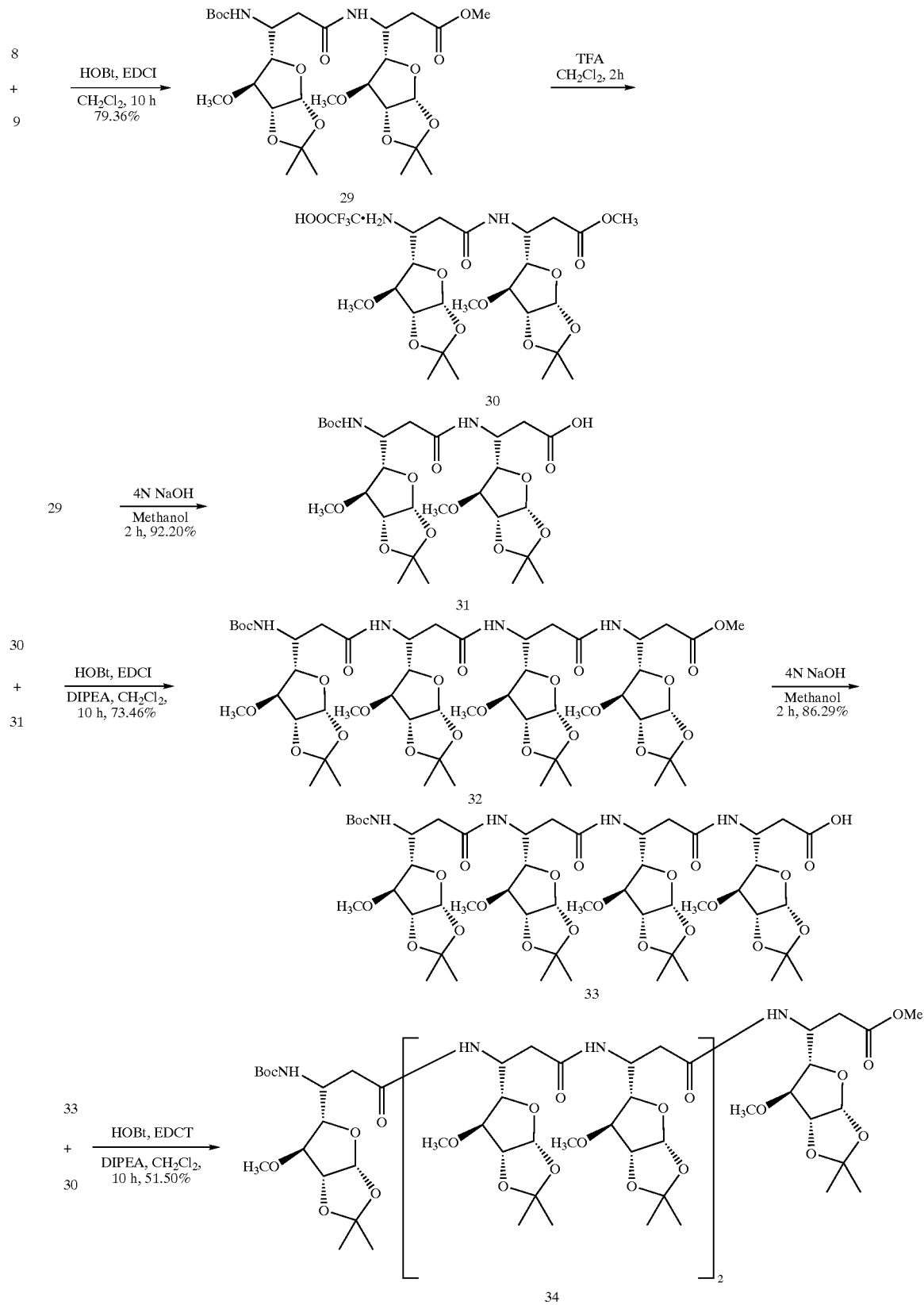

Dipeptide 29 was treated with an organic acid like TFA and the like in suitable solvents for eg; CH₂Cl₂ and the like to provide salt 30 as exemplified in example 4, part 2. Similarly 29 was also subjected to base induced hydrolysis in presence of suitable base like NaOH and the like in an acceptable solvents like MeOH to furnish an unprotected acid 31. For detailed experimental discussion see example 4, part 3. Further synthesis of a tetrapeptide was achieved upon coupling of 30 and 31 in the presence of conventional reagents like EDCI/HOBt/DIPEA in suitable solvents for eg; CH₂Cl₂ to yield 32 as exemplified in example 4, part 4. Tetrapeptide 32 was subsequently converted to free acid 33 under basic hydrolysis conditions with conventional reagents like NaOH in methanol. See example 4, part 5.

Further preparative methods of other oligomers is depicted in Scheme 5. For eg; coupling of 33 with 30 under the above standard reaction conditions (EDCI/HOBt/DIPEA, CH₂Cl₂, DMF) resulted in the hexapeptide 34. For experimental conditions see example 4, part 6.

Synthesis Peptides from R and S Amino Acids

Scheme 6 exemplifies a preferred preparative method of the invention that provides compounds of formula 35, 38, 41, 42 and 43 representing di, tetra, hexa, octa and tri C-linked carbo β-peptides. Thus in Scheme 6, the monomers 5 and 9 are coupled by conventional reagents such as dicyclohexyl carbodiimide/N-hydroxy succinimide (DCC/HoBt) or 1-ethyl-3-(3'-dimethyl amino prepyl) carbodiimide hydrochloride/N-hydroxy benztriazole (EDCI/HOBt) in solvent phase coupling procedures (see, example Bodanszky, M-; Bodanszky, A. The practice of peptide synthesis; Springer Verlag; New York, 1984) in suitable solvents such as CH₂Cl₂ to result in a dideptide 35. For exemplary reaction conditions for the preparation of 35 see example 5, part 1.

Dipeptide 35 was treated with an organic acid like TFA and the like in suitable solvents for eg; CH₂Cl₂ and the like to provide salt 36 as exemplified in example 5, part 2. Similarly 35 was also subjected to base induced hydrolysis in presence of suitable base like NaOH and the like in an acceptable solvents like MeOH to furnish an unprotected acid 37. For detailed experimental discussion see example 5, part 3.

Further synthesis of a tetrapeptide was achieved upon coupling of 36 and 37 in presence of conventional reagents like EDCI/HOBt/DIPEA in suitable solvents for eg;

Scheme 6

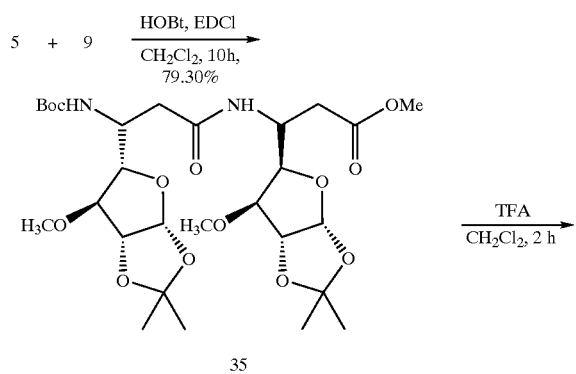

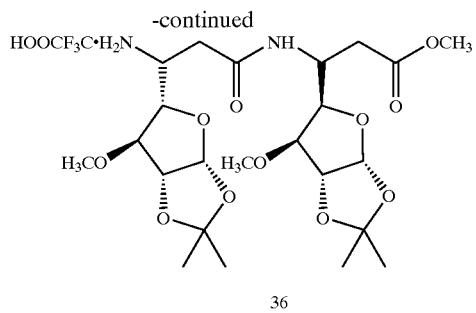

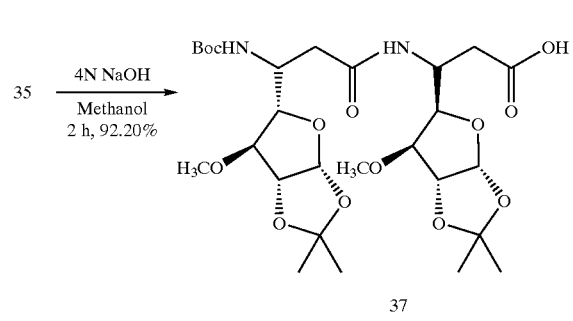

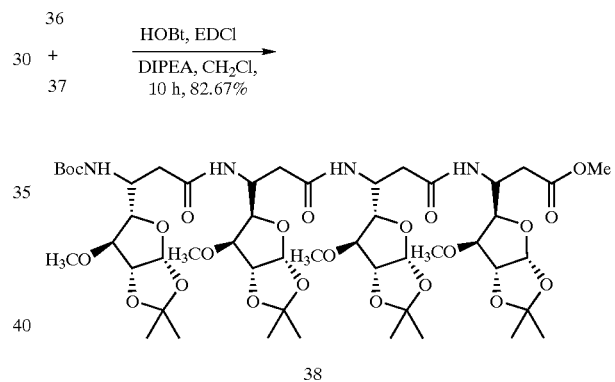

CH₂Cl₂ to yield 38 as exemplified in example 5, part 4. Tetrapeptide 38 was subsequently converted to free acid 39 under basic hydrolysis conditions with conventional reagents like NaOH in methanol. See example 5, part 5. Also 38 was further exposed to TFA in CH₂Cl₂ to deblock the Boc protecting group and the same was isolated as TFA salt 40, as exemplified in example 5, part 6.

Further preparative methods of other oligomers is depicted in Scheme 6. For eg; coupling of 40 with 36 under the above standard reaction conditions (EDCI/HOBt/DIPEA, CH₂Cl₂, DMF) resulted in the hexapeptide 41. For experimental conditions see example 5, part 7. Similarly coupling of 39 with 40 under the conventional peptide coupling reaction conditions as described above, with EDCI in presence of solvents like CH₂Cl₂:DMF in ratio as suitable enough for the reaction to result in the product octamer 42, as exemplified in example 5 part 8. Similarly coupling of 37 with 10 under the conventional peptide coupling reaction conditions as described above, with EDCI in presence of solvent like CH₂Cl₂ resulted in the product trimer 43, as exemplified in example 5 part 9 (Scheme 6).

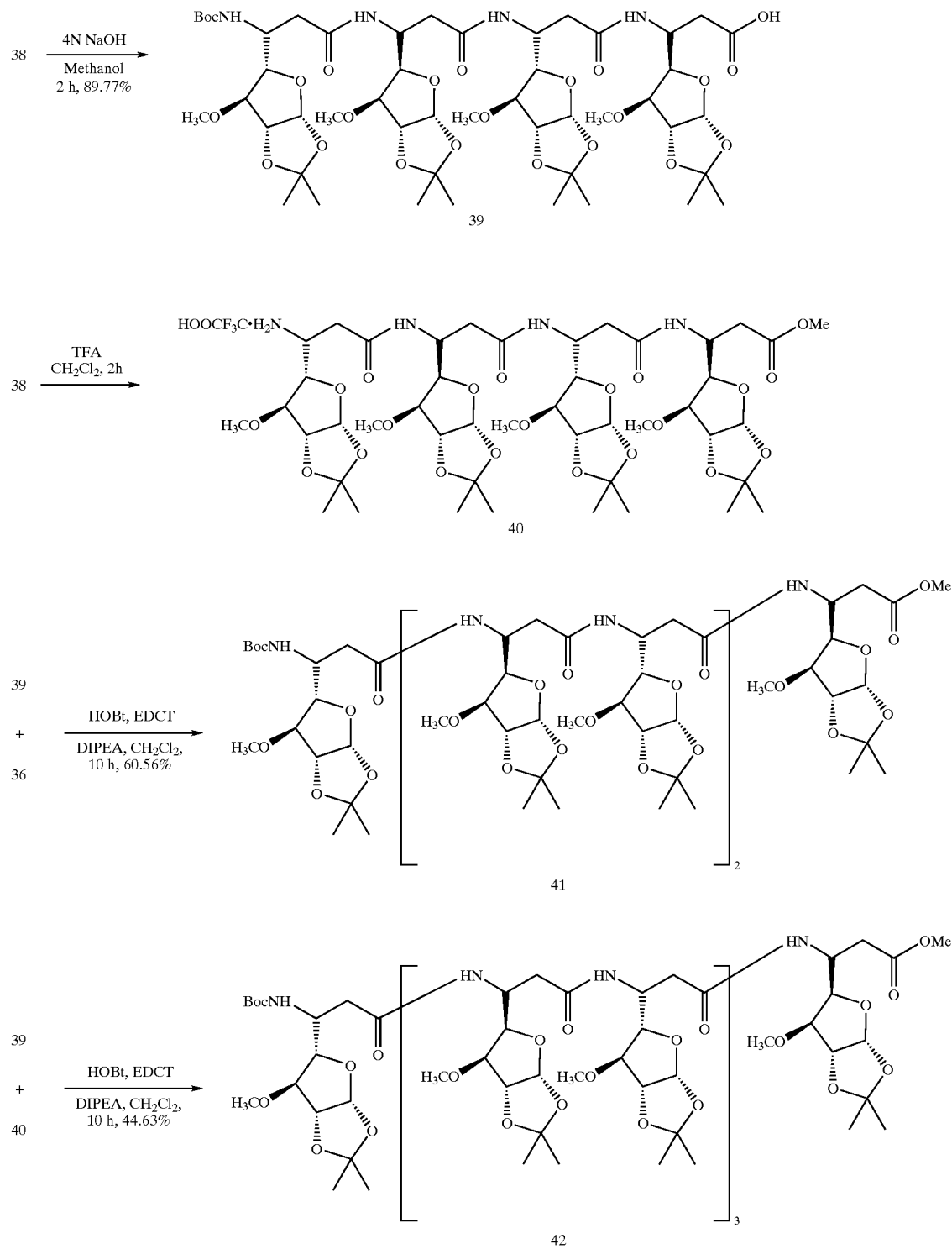

37 + 10 →(HOBt, EDCT, DIPEA, CH₂Cl₂, 10 h, 75.1%)

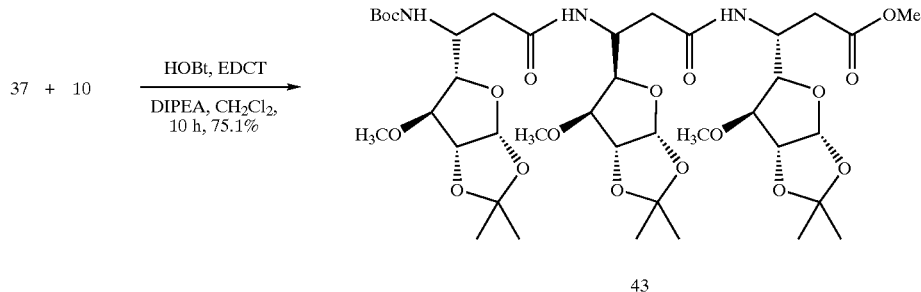

43

Further synthesis of a tetrapeptide 44 was achieved upon coupling of 22 and 36 in presence of conventional reagents like EDCI/HOBt/DIPEA in suitable solvents for eg; CH₂Cl₂ to yield 44 as exemplified in example 6, part 1 (Scheme 7). Similarly, as exemplified in example 6, part 2, tetrapeptide 45 was achieved upon coupling of 37 and 21 in presence of conventional reagents like EDCI/HOBt/DIPEA in suitable solvents for eg; CH₂Cl₂ to yield 45.

reaction conditions for the preparation of 47 see example 7, part 1.

Dipeptide 47 was treated with an organic acid like TFA and the like in suitable solvents for eg; CH₂Cl₂ and the like to provide salt 48 as exemplified in example 7, part 2. Similarly 47 was also subjected to base induced hydrolysis in presence of suitable base like NaOH and the like in an Scheme 7

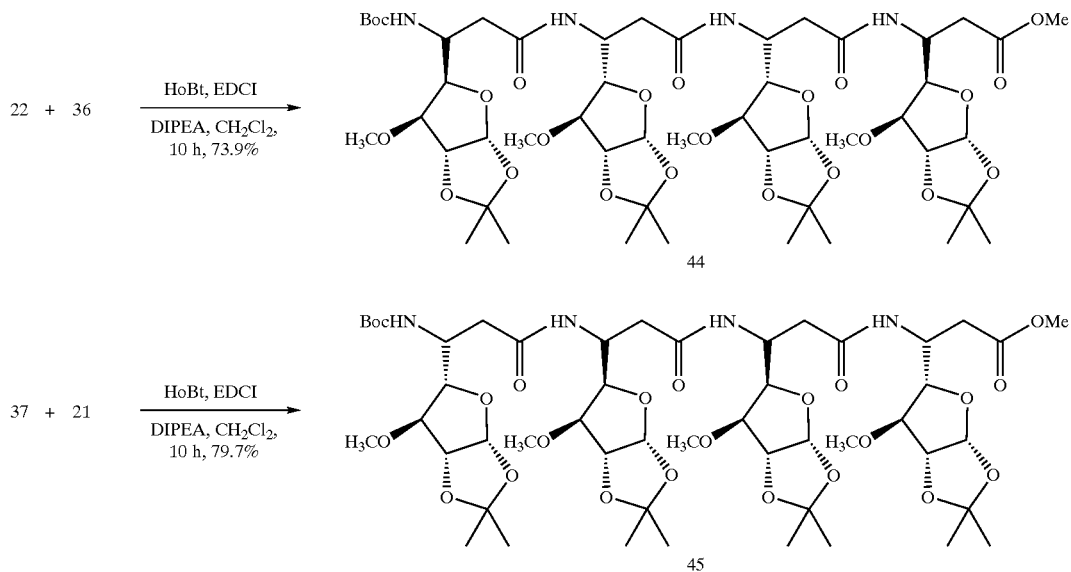

Scheme 8 exemplifies a preferred preparative method of the invention that provides compounds of formula 47, 50 arid 52 representing mixed di, tetra and hexa C-linked carbo β-peptides made from 6 and β-alanine methyl ester 46. Thus in Scheme 8, the monomers 6 and 46 are coupled by conventional reagents such as dicyclohexyl carbodiimide/ N-hydroxy succinimide (DCC/HoBt) in suitable solvents such as CH₂Cl₂ to result in a dideptide 47. For exemplary acceptable solvents like MeOH to furnish an unprotected acid 49. For detailed experimental discussion see example 7, part 3. Further synthesis of a tetrapeptide was achieved upon coupling of 48 and 49 in the presence of conventional reagents like EDCI/HOBt/DIPEA in suitable solvents for eg; CH₂Cl₂ to yield 50 as exemplified in example 7, part 4. Tetrapeptide 50 was subsequently converted to free acid 51 under basic hydrolysis conditions with conventional reagents like NaOH in methanol. See example 7, part 5.

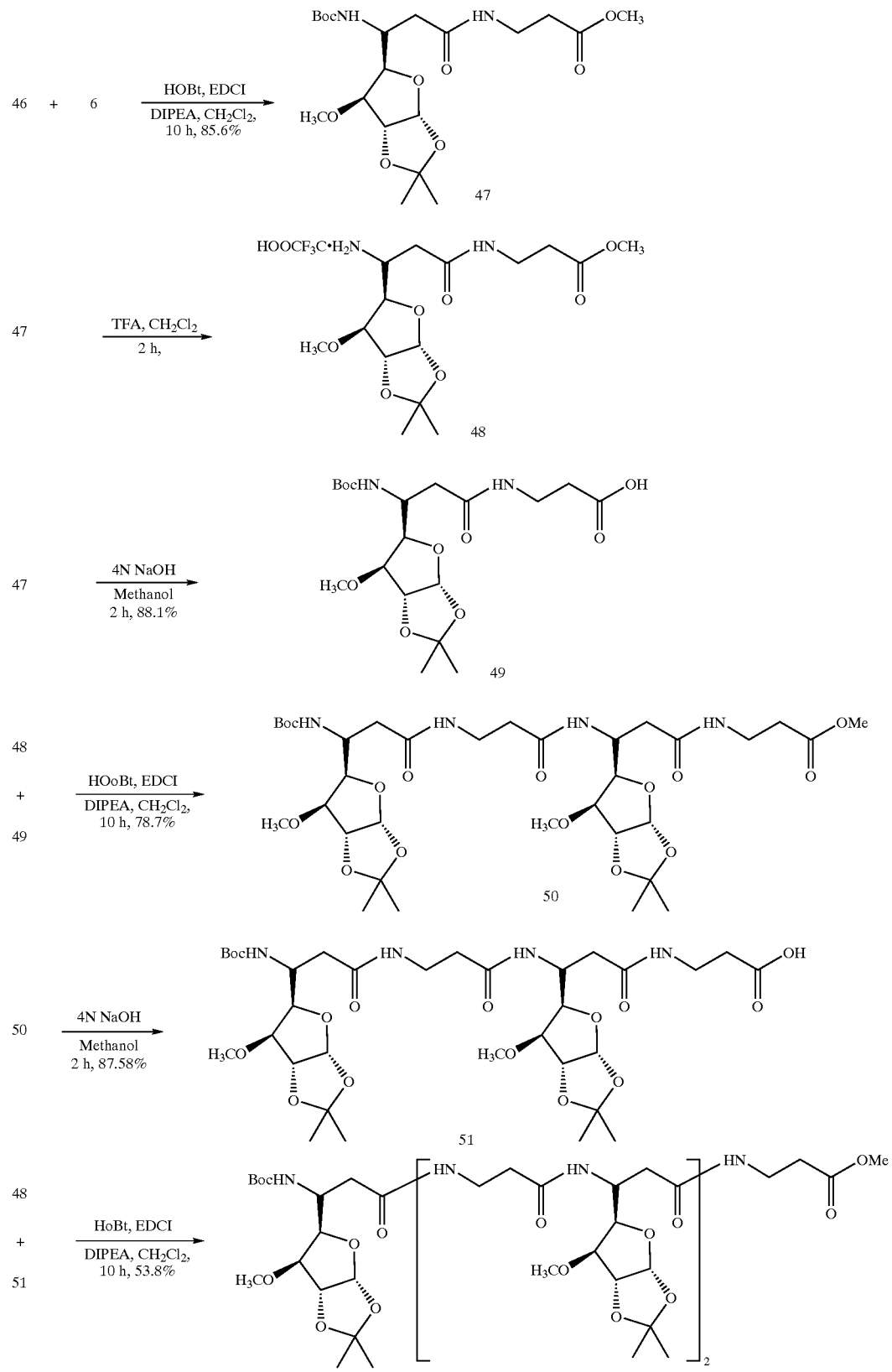
Scheme 8

Further preparative methods of other oligomers is depicted in Scheme 8. For eg; coupling of 48 with 51 under the above standard reaction conditions (EDCI/HOBt/DIPEA, $CH_2Cl_2$, DMF) resulted in the hexapeptide 52. For experimental conditions see example 7, part 6.

As exemplified in the Schemes 1–8, the synthetic protocols developed by this invention, numerous C-linked carbo β-peptide class of compounds represented by formula I can be synthesised. This new class of C-linked carbo β-peptides prepared by the method of invention are useful for numerous therapeutic applications. As exemplified in the preparative procedures, carbo β-peptide class of compounds described in here and represented by formula I can be readily prepared. As described in the proeceding secions the compounds that are prepared in the present invention are useful for numerous therapeutic applications. In need of treatment, these compounds can be administered by a variety of ways, such as orally, parentally, intravenously, subcutaneously and other routes.

Conformational Analysis

1. NMR Spectroscopy.

Molecular conformations were investigated by NMR spectroscopy. Such studies were carried out in about 2–8 mM solution in $CDCl_3$, DMSO-d6, $CD_3OH$ $CD_3OD$ or pyridine-d5. Two-dimensional (2-D) experiments like TOCSY (Cavanagh. J; Fairbrother. W. J; Palmer, N. J; Protein NMR Spectroscopy; Academic Press San Diego, 1996) and ROESY (Wuthrich, K; NMR of Proteins and Nucleic Acids, Wiley, N.Y., 1986) were obtained on VARIAN-INOVA 500 MHz spectrometer at 30° C. using standard pulse sequences, provided by VARIAN using phase sensitive (States, D. J.; Haberkoom, R. A.; Ruben, D. J, *J. Magn. Reson.* 48, 286–292, 1982) experiments. Data were processed with Varian VNMR 6.1b software. The data for these experiments were collected as 384×2048 matrix, using 8–16 scans, per $t_1$, increment. The data were zero filled and Fourier transformed as 2k×4k data matrix. Almost all the resonances in the backbone were very highly resolved in $CDCl_3$ and could be assigned with the help of TOCSY and ROESY experiments. TOCSY provided the assignments within the same residue and ROESY provided sequential assignments.

In these oligomers the N-terminal amides show NOE with intra residue $C_\alpha H$ proton alone, and donot show any inter residue NH/CαH NOE like other amides. This assignment has further been supported from the NOE between the amide and Boc group. Also the $C_\alpha$ protons at the C-terminal residue has been identified from the presence of NOE only with the self-amide NH.

Information on Hydrogen Bonding a) Solvent Titraton Studies

In non-polar solvents, titration with a polar solvent is used to assess stability of the structure. Intra-molecularly H-bonded amide proton chemical shifts in $CDCl_3$ do not change much when a polar hydrogen bond promoting solvents like DMSO-d6 is added upto 33% v/v. Amide protons, which are not intramolecularly hydrogen bonded, form hydrogen bond with DMSO-d6 and their resonances show large shifts towards downfield.

b) Amide Proton Exchange

Amide proton exchange is usually used for getting information on intramolecular hydrogen bonding in peptides, which permits to assess conformational stability of peptides. Presence of intramolecular hydrogen bonds results in reduced rate of NH/ND exchange. The amide protons of the peptide, which are forming intramolecular hydrogen bonding exchanges very slowly in $CD_3OD$ solution, even upto 2–3 days, where as non-hydrogen bonded amides can exchange very fast, sometimes even with in few minutes.

c) Variable Temperature Experiments.

In DMSO-d6, temperature coefficients of the amide proton chemical shift ($\Delta\delta/\Delta T$ in ppb/° K) is used as a signature of intra-molecular hydrogen bond. By varying the temperature the amides chemical shifts show small magnitude of temperature coefficients, when they participate in intramolecular hydrogen bonds. Those amides, which are not taking part in hydrogen bonding, show large magnitude of temperature coefficients.

2. Circular Dichroism Spectroscopy:

The circular dichroism (CD) data in the UV region was obtained on JASCO-510 and JASCO-715 instrument at room temperature (nominally 20° C.). The ellipticities are reported as mean residue molar ellipticity, which is obtained by normalizing for the total number of amide chromophores present in the oligomer.

3. Molecular Dynamics/Mechanics Studies

Restrained molecular dynamics data was used to generate 20 low energy conformation. The back bone heavy atoms superimposed rather well (RMSD<A°). However the C terminal did show fraying. The side chains did show a larger degree of freedom.

Results and Discussions:

Tetrapeptide-23, Hexapeptide-26 and Octapeptide-27

Solvent titration studies by adding upto 33% v/v DMSO-d6 in $CDCl_3$ show that apart from the second residue amide [NH (2)] all the amide protons are hydrogen bonded in both the peptides as they show very small (<0.6 ppm) change in their chemical shifts. This is further supported by a very large range for the amide chemical shifts (about 3 ppm for 23, 26 and 27) as well as their very low field shifts (δNH for two amides in 26, four amides in 26 and six amides in 27 arm above 7.0 ppm). The $C_\alpha H$ protons also show a very big chemical shift dispersion of about 0.7, 0.8 and 0.75 ppm respectively for 23, 26 and 27. The presence of $^3J_{C\alpha H-C\beta H}$ of about 5 Hz or below and 10 Hz and above very clearly demonstrates that the θ are taking only the g/t conformations. The molecules take primarily a single value of θ=60°, which is further supported by strong inter residue NOE of $NH/C_\alpha H_{(pro-R)}$, $C_\beta H/C_\alpha H_{(pro-S)}$.

The ROESY spectra show very distinctive NOE's corresponding to the 10/12/10 helices. Specially noteworthy are the medium backbone NOE between $C_\beta H(2)$ with NH (4) and $C_\alpha H_{(pro-R)}$ (4) NOE's in 23, qualifying the 12-membered hydrogen bond. Where as in 23 and 26 several of these NOE propagate along the helix. For 26 strong $C_\beta H$ (2)/NH (4) and $C_\beta H$ (2)/$C_\alpha H_{(pro-R)}$ (4) as well as $C_\beta H(4)$/NH (6) and $C_\beta H(4)/C_\alpha H_{(pro-R)}$ (6) NOE's are seen. For 27 in addition to the NOE's mentioned for 1 and 2, we observe $C_\beta H$ (6)/NH (8) and $C_\beta H(6)/C_\alpha H_{(pro-R)}$ (8) NOE peaks. In addition, characteristic weak NOE due to 10-membered hydrogen bonds of the helix between NH (1)/NH (2), NH (3)/NH (4), NH (5)/NH (6) and NH (7)/NH (8) are observed for 27. Because of the smaller size of 26 only NH (1)/NH (2), NH (3)/NH (4) and NH (5)/NH (6) and for 23 NH (1)/NH (2) and NH (3)/NH (4) inter residue NOE's are observed. In 23, 26 and 27 despite the fact that Boc amide is the first residue, it participates in H-bonding and thus confirms their remarkable stability. In short α-helices the ends are frayed in solution. These chirality-controlled oligomers show that the sugar containing β-aminoacids lead to very well defined helices even for peptides containing only four residues.

The orientation of sugar rings with respect to the backbone is well characterized. Excluding residue 2 (R(2)), $^3J_{C\beta H-C4H}$ is large ($\cong$10 Hz ), corresponding to dihedral angle $C_\beta H-C_\beta-C_4-C_4H$ ($\chi_1$) of about 180°. Such an orientation is further supported by NOE's of NH/C$_4$H and NH/C$_\alpha$H$_{(pro-R)}$. It leaves the sugar ring planes alternately pointing in opposite direction (opposite to the sense of the screw axis of the helix). The methoxy groups of the odd residues point towards the C terminal, where as those for the even residues, excluding the second residue, points towards the N terminal. For residue 2 (R (2)), the $^3J_{C\beta H-C4H}$=6.0, 5.8 and 6.2 Hz for 23, 26 and 27. This indicates a predominance of conformation with torsion angle |C$_\beta$H—C$_\beta$—C$_4$—C$_4$H|=60°. The presence of strong NOE of C$_4$H/C$_\alpha$H$_{(pro-S)}$ and medium NOEs of C$_4$H/C$_\alpha$H$_{(pro-S)}$, C$_3$H/ C$_\alpha$H$_{(pro-R)}$ and C$_3$H/C$_\alpha$H$_{(pro-S)}$ enabled us to fix this angle as –60°.

The couplings for sugar zing are all very small. The vicinal coupling constants $^3J_{C1H-C2H}\cong 3$ Hz, $^3J_{C2H-C3H}\cong 0$ Hz and $^3J_{C3H-C4H}\cong 4$ Hz correspond to a sugar pucker of $^3T_2$. Strong NOE between Me$_{(pro-R)}$/C$_1$H and Me$_{(pro-R)}$/C$_2$H as well as weak Me$_{(pro-S)}$/C$_4$H NOE show that the isopropylidene ring exists in envelop conformation. These observations are also in conformity with the structure of the sugar unit in several other molecules with C—C glycosidic linkages.

The data in DMSO-d6 was also well understood and almost all the NOE's discussed above were obtained. Though the chemical shift dispersion was not as much as in CDCl$_3$ and also some of the couplings indicate little more flexibility in the structure. However, the 10/12/10 helix is very well preserved.

Tripeptide-43, Tetrapeptide-38, Hexapeptide-41 and Octapeptide-42

The solvent titration studies in CDCl$_3$ and variable temperature studies in DMSO-d6 very clearly show that for 43 and 38 amide protons of residue S(2) and R(3) are hydrogen bonded. For 41 the presence of four hydrogen bonds for amide protons, corresponding to S(2), R(3), S(4) and R(5) is observed and for 42 the presence of six hydrogen bonds for amide protons S(2), R(3), S(4), R(5), S(6)is observed. The large amide chemical shifts range (e.g., about 3.57 ppm for 7) and low field shifts of several of them ($\delta$ NH up to 8.92 ppm for 7) further support the presence of large number of hydrogen bonds in this family of molecules. The C$_\alpha$H protons also show very large dispersion of 0.52, 0.93, 1.08 and 0.92 ppm for 43, 38, 41 and 42 respectively, additionally confirming a well defined structure for them. Very large (>10 Hz) and very small (often <5 Hz) $^3J_{C\alpha H-C\beta H}$ values very clearly show that molecule takes primarily a predominant single conformation with θ=60°. This is ether supported by strong inter residue NOE between NH/C$_\alpha$H$_{(Pro-R)}$, C$_\beta$H/ C$_\alpha$H$_{(Pro-S)}$.

The ROESY spectra show characteristic NOE cross peaks corresponding to the presence of 12/10 helices in 43, 38 and 12/10/12/10 helix in 41 and 12/10/12/10/12/10 helix in 42. Strong strength of NOE's of C$_\beta$H (1)/NH (3) and C$_\beta$H (1)/C$_\alpha$H$_{(pro-R)}$ (3) and weak NH (2)/NH (3) NOE, in addition to presence of two hydrogen bonded amides shows the presence of 12/10 helices in 43 and 38. For 41 in addition to above NOE's, strong intensity NOE's C$_\beta$H(3)/NH (5) and C$_\beta$H (3)/C$_\alpha$H$_{(pro-S)}$ (5) and weak intensity NH (4)/NH (5) are observed. The above NOE's and participation of NH (2), NH (3), NH (4) and NH (5) in hydrogen bonding confirms the presence of intertwined 12/10/12/10 helix for 41. For 42 along with the above mentioned NOE's seen in 4, 5 and 6 also strong intensity NOE's C$_\beta$H(5)/NH (7) and C$_\beta$H (3)/ C$_\alpha$H$_{(pro-S)}$ (7) and weak intensity NH (6)/NH (7) are observed. The above NOE's and participation of NH (2), NH (3), NH (4), NH (5), NH (6), NH (7) in hydrogen bonding confirms the presence of intertwined 12/10/12/10/12/10 helix for 42. Leaving apart the first residue the sugar ring orientation with respect to the backbone also seems to be reasonably well defined. The $^3J_{C\beta H-C4H}$ of about 10 Hz and the additional presence of NH/H4 and NH/C$\alpha$H$_{(pro-R)}$ NOE's is in conformity of $\chi_1$ in the vicinity of 180° for these residues. For the first residue the $^3J_{C\beta H-C4H}$ is small, being 7.3, 7.2, 6.0 and 6.2 Hz for 43, 38, 41 and 42. Averaging due to multiple rotamers may be a plausible cause for this. The $\chi_1$ of about 180° makes the sugar rings plane alternately pointing in opposite direction. Thus for 41 the methoxy group at residue 3 and 5 point along the C terminus of the helix axis, where as the ones at 2, 4 and 6 point along the helix axis towards the N terminus. Presence of about 2.7 residues per turn causes sugar rings of every fourth residue to be in each others proximity but slightly displaced by about 40°.

In all these molecules the sugar pucker is very well defined. The coupling between protons in the ring are: $^3J_{C1H-C2H}\cong 3$ Hz, $^3J_{C2H-C3H}\cong 0$ Hz and $^3J_{C3H-C4H}\cong 4$ Hz. These couplings correspond to a $^3T_2$ sugar pucker. Strong NOE, Me$_{(Pro-R)}$/C$_1$H and Me$_{(Pro-R)}$/C$_2$H as well and weak Me$_{(Pro-S)}$/C$_4$H NOE show that the isopropilidine ring predominantly takes an envelop conformation. The observations are consistence with the structure of such a sugar units in other molecules with C—C glycocidic linkages.

The data in DMSO-d6 for 43, 38 and 41 was also well understood and almost all the NOE's discussed above were obtained. Though the chemical shift dispersion was not as much as in CDCl3 and also some of the couplings indicate little more flexibility in the structure. However, the 12/10/12 helix is very well preserved.

Tetrapeptide-14 and Hexapeptide-17

No characteristic information on a well-defined structure was obtained. In CDCl$_3$ amide protons appeared below δ<7 ppm and solvent titration studies did not show their participation in hydrogen bond. In CD$_3$OD, amide protons exchanged very quickly and most of them could not be detected after 12 hours. The consideration of steric and torsional energies (Wu et al.) does not support regular 14- or 10/12 helix for these oligomers Tetrapeptide-32, Hexapeptide-34

In CDCl$_3$ due to severe overlap in the C$_\alpha$H and C$_\beta$H region, most of the specific assignments could not be made. Several of the amide resonances appear at low field (δ>7.5 ppm) and solvent titration studies indicate that many of the amide protons are participating in hydrogen bonding. Since the amide protons are isolated the 3JNH$_{\beta H}$ coupling could be obtained. The overlap of resonances in other solvents was more severe. In CD$_3$OD amide proton exchange was fast indicating absence of any structure.

The following examples are given by way of illustration and therefore should not be construed to limit the scope of the present invention.

Experimental

General: melting points are uncorrected. CH$_2$Cl$_2$ was freshly distilled from CaH$_2$ under N$_2$. DMF was distilled under reduced pressure from nindrydrin and stored over 4 A molecular sieves. Triethyl amine was distilled from CaH$_2$ before use. Other solvents and reagents were used as obtained from commercial suppliers. For Boc removal, 10% TFA in CH$_2$Cl$_2$ (checkup) was used. Column chromatography was carried out by using 60 to 120 mesh silica gel. Routine $^1$H-NMR spectra were obtained on a INOVA-500 MHz and 800 MHZ spectrometers and are referenced to residual protonated NMR solvents. Routine $^{13}$C-NMR spectra were recorded at 125 MHz and are referenced to the NMR solvents. High-resolution electron impact mass spectrometry (or HRMS-FAB) V G Autospec Mass Spectrometer at 5 or 7 K resolution using perfluoro kerosene as an internal standard. IR spectra were recorded on and reported in wavenumbers (cms$^{-1}$).

General Procedures (GP)

GP-1: Debenzylation of Amino Ester

Benzyl protected amino acid ester (1.0 mmol) was dissolved in methanol (0.5 mL), treated with 10% Pd—C (0.1 gm for 1.0 g) and stirred at room temperature under hydrogen atmosphere for 12 h. After completion of the reaction (TLC analysis), the reaction mixture was filtered and filtrate evaporated. The amine was used as such for further reactions without purification.

GP-2: Boc Protection of Amino Esters

Free amine ester (1.0 mmol) was dissolved in THF (5 mL) and cooled to 0° C. (Boc)$_2$O (1.0 mmol) in THF (5 mL) was added slowly for 15 min. The reaction mixture was allowed to warm to room temperature and stirred for 12 h. THF was evaporated and purified the residue by column chromatography (Silica gel, 15% EtOAc—pet ether) to give pure Boc protected amino acid ester.

GP-3: Hydrolysis of the Amino Acid Ester/Peptide Ester

A solution of the ester (1.0 mmol) in MeOH (4 mL) was treated with 4N NaOH (4 mL) at room temperature. After 2 h, methanol was removed and adjusted to pH 2–3 with aq. 1N HCl and extracted with EtOAc. The organic layer was dried (Na$_2$SO$_4$) and evaporated to give acid.

GP-4: Boc Deprotection of Amino Acid/Peptide Ester

A stirred solution of the amino acid ester or peptide ester (0.1 g) in dry CH$_2$Cl$_2$ (0.9 mL) was treated at 0° C. under nitrogen atmosphere with CF$_3$COOH (0.1 mL) at room temperature and stirred for 2 h. It was evaporated and the residue dried under high vacuum. The salts were used as such without further purification or characterization.

GP-5: Preparation of Dipeptides from Monomers

Boc amino acid (1.0 mmol) dissolved in dry. CH$_2$Cl$_2$ (3.5 mL) was sequentially treated with HOBt (1.2 mmol) and EDCI (1.2 mmol) at 0° C. After 15 min, free amine ester (1.0 mmol) in dry CH$_2$Cl$_2$ (2.5 mL) was added to the reaction mixture. The reaction mixture was allowed to reach room temperature and stirred further for 10 h. It was diluted with CHCl$_3$, washed with 1N HCl, water, and aq. saturated. NaHCO$_3$ solution and aq. NaCl solution. The organic layer was dried (Na$_2$SO$_4$) and evaporated to give the dipeptides.

GP-6: Preparation of Tripeptides

Boc protected dipeptide acid (1.0 mmol) dissolved in dry CH$_2$Cl$_2$ (6 mL) was treated with HOBt (1.2 mmol) and EDCI (1.2 mmol) at 0° C. After 15 min, free amine ester (1.0 mmol; obtained by treatment of amine salt (1.0 mmol) with DIPEA (1.5 mmol)) in dry CH$_2$Cl$_2$ (2.5 mL) was added. It was allowed to reach room temperature and stirred for 10 h. The reaction mixture was diluted with CHCl$_3$, washed with 1N HCl, water, aq. sat. NaHCO$_3$ solution and NaCl solution. The organic layer was dried Na$_2$SO$_4$) and evaporated to give tripeptide.

GP-7: Preparation of Tetra Peptides from Dipeptides

Dipeptide acid (1.0 mmol) dissolved in dry CH$_2$Cl$_2$ (6 mL) was treated with HOBt (1.2 mmol) and EDCI (1.2 mmol) at 0° C. and treated with dipeptide amine in dry CH$_2$Cl$_2$ (6.5 mL) as described in GP-6 to give tetrapeptide.

GP-8: Preparation of Hexa Peptides

Tetra peptide acid (1.0 mmol) dissolved in dry CH$_2$Cl$_2$: dry DMF (4:1) (10 mL) was treated with HOBt (1.2 mmol) and EDCI (1.2 mmol) at 0° C. After 15 min., dipeptide amine (1.0 mmol) in dry CH$_2$Cl$_2$ (6 mL) was added and worked up as described in GP-6 to give hexapeptides.

GP-9: Preparation of Octa Peptides

Tetrapeptide acid (1.0 mmol) dissolved in dry CH$_2$Cl$_2$: dry DMF (4:1) (10 mL) was treated with HOBt (1.2 mmol) and EDCI (1.2 mmol) at 0° C. After 15 min. tetra peptide amine (1.0 mmol) in dry CH$_2$Cl$_2$ (12 mL) was added and work up as described in GP-6 gave octapeptide.

EXAMPLE-1

Part 1: Unsaturated Ester (Scheme 1; 2)

Aldehyde 1 (1.95 g, 9.65 mmol) in benzene (10 mL) was added to a stirred solution of (methoxy carbonyl methylene) triphenylphosphine (4.84 g, 14.48 mmol) in benzene (10 mL) at reflux and stirring was continued for 5 h at same temperature. After reaction benzene was removed and crude directly loaded on a flash chromatography column with 10% EtOAc in pet.ether to give 2 (1.71 g, 88.7%) as syrup, $[\alpha]_D$=−90.8 (c 1.87, CHCl$_3$), IR (Neat): 2989, 2942, 1725, 1440, 1379, 1260, 1200, 1080, 1020, 875 cm$^{-1}$; $^1$H-NMR (500 MHz, CDCl$_3$) δ 6.96 (dd, J=4.8, 15.8 Hz, 1H, T-C$_5$H), 6.33 (dd, J=6.9, 11.7 Hz, 1H, C—C$_5$H), 6.18 (dd, J=1.7, 15.8 Hz, 1H, T-C$_6$H), 5.97 (d, J=3.8 Hz, 1H, C—C$_1$H), 5.96 (d, J=3.8 Hz, 1H, T-C$_1$H), 5.95 (dd, J=1.7, 11.7 Hz, 1H, C—C$_6$H), 5.64 (ddd, J=1.7, 3.2, 6.9 Hz, 1H, C—C$_4$H), 4.80 (ddd, J=1.7, 3.2, 4.8 Hz, 1H, T-C$_4$H), 4.62 (d, J=3.8 Hz, 1H, T-C$_2$H), 4.61 (d, J=3.8 Hz, 1H, C—C$_2$H), 4.05 (d, J=3.2 Hz, 1H, C—C$_3$H), 3.78 (d, J=3.2 Hz, 1H, T-C$_3$H), 3.74 (s, 3H, T-COOMe), 3.74 (s, 3H, C—COOMe), 3.38 (s, 3H, T-OMe), 3.35 (s, 3H, C—OMe), 1.53 (s, 3H, C-Me), 1.51 (s, 3H, T-Me), 1.34 (s, 6H, C&T-Me).

Method A

To a stirred solution of 2 (0.86 g, 3.33 mmol) in THF benzylamine (0.36 mL, 3.33 mmol) and DBU (0.50 mL, 3.33 mmol) were added and stirred at room temperature for 8 h.THF was removed and reaction mixture was directly loaded on chromatography column with 15% EtOAc in pet. ether to give 3 (0.72 g, 59.21%) as a syrup.

Method B

A stirred solution of 2 (4.0 g, 15.5 mmol) and benzylamine (4.22 mL, 38.76 mmol) was stirred at room temperature. After 12 h the reaction mixture was directly loaded on a chromatography column with 10% EtOAc in pet. ether to give 4 (1.25 g, 22.1%) as a syrup and 15% EtOAc in pet. ether to give 3 (2.6 g, 45.9%) as a syrup.

Part 2: Benzyl Protected (S) Amino Acid Ester (Scheme 1; 3)

$[\alpha]_D$=−31.078 (c 1.0, CHCl$_3$), IR (Neat): 3370, 2980, 2918, 1718, 1449, 1368, 1158, 1072, 1013 cm$^{-1}$; $^1$H-NMR (500 MHz, CDCl$_3$) δ 7.32 (m, 2H, Ar—H), 7.29 (m, 2H, Ar—H), 7.22 (m, 1H, Ar—H), 5.91 (d, J=3.8 Hz, 1H, $C_1$H), 4.59 (d, J=3.9 Hz, 1H, $C_2$H), 4.23 (dd, J=3.2, 8.7 Hz, 1H, $C_4$H), 3.86 (abq, J=12.9 Hz, 2H, Ar—$CH_2$), 3.73 (d, J=3.2 Hz, 1H, $C_3$H), 3.69 (s, 3H, —COOMe), 3.41 (dt, J=5.6, 8.7 Hz, 1H, $C_\beta$H), 3.37 (s, 3H, —OMe), 2.57 (dd, J=5.6, 14.9 Hz, 1H, $C_\alpha$H'), 2.46 (dd, J=5.6, 14.9 Hz, 1H, $C_\alpha$H), 1.48 (s, 3H, Me), 1.32 (s, 3H, Me). FAB MS: 366 ($M^+$+H)

Part 2: Benzylprotected (R) Amino Acid Ester (Scheme 1; 4)

$[\alpha]_D$=−35.148 (c 1.0, $CHCl_3$), IR (Neat): 3340, 2983, 2935, 1729, 1455, 1381, 1162, 1074, 1017 $cm^{-1}$; $^1$H-NMR (500 MHz, $CDCl_3$) δ 7.32 (m, 2H, Ar—H), 7.29 (m, 2H, Ar—H), 7.22 (m, 1H, Ar—H), 5.87 (d, J=3.8 Hz, 1H, $C_1$H), 4.57 (d, J=3.9 Hz, 1H, $C_2$H), 4.12 (dd, J=3.0, 8.9 Hz, 1H, $C_4$H), 3.83 (abq, J=14 Hz, 2H, Ar—$CH_2$), 3.83 (d, J=3.0 Hz, 1H, $C_3$H), 3.66 (s, 3H, —COOMe), 3.44 (ddd, J=4.2, 7.2, 8.9 Hz, 1H, $C_\beta$H), 3.39 (s, 3H, —OMe), 2.80 (dd, J=4.2, 15.6 Hz, 1H, $C_\alpha$H'), 2.57 (dd, J=7.2, 15.6 Hz, 1H, $C_\alpha$H), 1.48 (s, 3H, Me), 1.32 (s, 3H, Me). FAB MS: 366 ($M^+$+H)

Part 3: Debenzylation of (S) Amino Acid Ester (Scheme 2; 5)

Debenzylation of 3 (0.82 g, 2.24 mmol) with 10% Pd—C (0.082 g) in methanol (2.5 mL) was performed according to GP-1 to obtain amine 5, which was used as such for further reactions without purification.

Part 4: Debenzylation and Boc Protection of (S) Amino Acid Ester (Scheme 2; 5a)

Debenzylation of 3 (0.82 g, 2.24 mmol) was performed according to GP-1 to obtain amine 5, which was treated with $Boc_2O$ (0.48 mL, 2.07 mmol) as per GP-2 and purified by column chromatography (60–120 mesh Silica-gel, 15% EtOAc-pet. ether) to give 5a (0.61 mg, 72%), $[\alpha]_D$=−26.91 (c 1.1, $CHCl_3$), IR (Neat): 3385, 2980, 2938, 1725, 1705, 1502, 1308, 1161, 1071, 1013 $cm^{-1}$; $^1$H-NMR (500 MHz, $CDCl_3$) δ 5.91 (d, J=3.8 Hz, 1H, $C_1$H), 5.09 (bs, 1H, S—NH), 4.57 (d, J=3.8 Hz, 1H, $C_2$H), 4.30 (m, 1H, $C_\beta$H), 4.298 (m, 1H, $C_4$H), 3.68 (d, J=3.1 Hz, 1H, $C_3$H), 3.68 (s, 3H, —COOMe), 3.373 (s, 3H, —OMe), 2.71 (dd, J=3.2, 14.6 Hz, 1H, $C_\alpha$H'), 2.67 (dd, J=7.9, 14.6 Hz, 1H, $C_\alpha$H), 1.48 (s, 3H, Me), 1.43 (s, 9H, -Boc), 1.31 (s, 3H, Me). FAB MS: 376 ($M^+$+H)

Part 5: Ester Hydrolysis of (S) Amino Acid Ester (Scheme 2; 6)

Ester 5a (0.60 g, 1.60 mmol) on hydrolysis with 4N NaOH (6.5 mL) in methanol (6.5 mL) was performed according to GP-3 to give 6 (0.49 g, 85%) as a syrup, $[\alpha]_D$=−43.46 (c 1.0, $CHCl_3$), IR (Neat): 3353, 2980, 2925, 1710, 1504, 1313, 1161, 1067, 1012 $cm^{-1}$; $^1$H-NMR (500 MHz, DMSO-d6) δ 6.68 (d, J=8.0 Hz, 1H, S—NH), 5.76 (d, J=3.8 Hz, 1H, $C_1$H), 4.64 (d, J=3.8 Hz, 1H, $C_2$H), 4.02 (m, 1H, $C_\beta$H), 4.02 (m, 1H, $C_4$H), 3.58 (d, J=3.1 Hz, 1H, $C_3$H), 3.29 (s, 3H, OMe), 2.29 (dd, J=3.2, 14.6 Hz, 1H, $C_\alpha$H'), 2.23 (dd, J=7.9, 14.6 Hz, 1H, $C_\alpha$H), 1.37 (s, 3H, Me), 1.34 (s, 9H, -Boc), 1.23 (s, 3H, Me). FAB MS: 384 ($M^+$+Na)

Part 6: Boc Deprotection of (S) Amino Acid Ester (Scheme 2; 7)

Boc deprotection of 5a (0.207 g, 0.554 mmol) with TFA (0.20 mL) in $CH_2Cl_2$ (2.0 mL) was performed according to GP-4 to obtain amine salt 7, which was used as such for further reactions without purification.

Part 7: Debenzylation of (R) Amino Acid Ester (Scheme 2; 8)

Debenzylation of 4 (1.330 g, 3.64 mmol) with 10% Pd—C (0.130 g) in methanol (3.5 mL) was performed according to GP-1 to obtain amine 8, which was used as such for further reactions without purification.

Part 8: Debenzylation and Boc Protection of (R) Amino Acid Ester (Scheme 2; 8a)

Debenzylation of 4 (1.330 g, 3.64 mmol) was performed according to GP-1 to obtain amine 8, which on treatment with $Boc_2O$ (0.835 mL, 3.64 mmol) as per GP-2 and purification by column chromatography (60–120 mesh Silica-gel, 15% EtOAc-pet. ether) to give 8a (0.98 g, 72%), $[\alpha]_D$=−25.616 (c 0.48, $CHCl_3$), IR (Neat): 3374, 2979, 2923, 1718, 1499, 1361, 1170, 1080, 1016 $cm^{-1}$; $^1$H-NMR (500 MHz, $CDCl_3$) δ 5.87 (d, J=3.9 Hz, 1H, $C_1$H), 5.28 (d, J=6.9 Hz, 1H, R—NH), 4.54 (d, J=3.9 Hz, 1H, $C_2$H), 4.36 (dddd, J=7.7, 6.9, 6.1, 5.0 Hz, 1H, $C_\beta$H), 4.28 (dd, J=7.7, 3.4 Hz, 1H, $C_4$H), 3.71 (d, J=3.4 Hz, 1H, $C_3$H), 3.68 (s, 3H, COOMe), 3.40 (s, 3H, OMe), 2.71 (dd, J=6.1, 15.6 Hz, 1H, $C_\alpha$H'), 2.66 (dd, J=5.0, 15.6 Hz, 1H, $C_\alpha$H), 1.47 (s, 3H, Me), 1.43 (s, 9H, -Boc), 1.31 (s, 3H, Me). FAB MS: 376 ($M^+$+H)

Part 9: Ester Hydrolysis of (R) Amino Acid Ester (Scheme 2; 9)

Hydrolysis of ester 8a (0.980 g, 2.61 mmol) with 4N NaOH (10.5 mL) in methanol (10.5 mL) was performed according to GP-3 to give 9 (0.815 g, 84%) as a white solid, M.p. 124–127° C.; $[\alpha]_D$=−22.540 (c 0.55, $CHCl_3$), IR (KBr): 3324, 2983, 2929, 1708, 1643, 1410, 1262, 1160, 1076, 1018 $cm^{-1}$; $^1$H-NMR (500 MHz, $CDCl_3$) δ 5.88 (d, J=3.8 Hz, 1H, $C_1$H), 5.33 (d, J=9.4 Hz, 1H, R—NH), 4.55 (d, J=3.8 Hz, 1H, $C_2$H), 4.37 (dddd, J=9.4, 7.6, 5.6, 4.9 Hz, 1H, $C_\beta$H), 4.32 (dd, J=7.6, 2.6 Hz, 1H, $C_4$H), 3.73 (d, J=2.6 Hz, 1H, $C_3$H), 3.41 (s, 3H, OMe), 2.77 (dd, J=5.6, 16.2 Hz, 1H, $C_\alpha$H), 2.72 (dd, J=4.9, 16.2 Hz, 1H, $C_\alpha$H'), 1.48 (s, 3H, Me), 1.44 (s, 9H, -Boc), 1.32 (s, 3H, Me). FAB MS: 362 ($M^+$+H).

Part 10: Boc Deprotection of (R) Amino Acid Ester (Scheme 2; 10)

Boc deprotection of 8a (0.275 g, 0.73 mmol) with TFA (0.28 mL) in $CH_2Cl_2$ (2.5 mL) was performed according to GP-4 to obtain salt 10.

EXAMPLE-2

Part 1: Preparation of Dipeptide (Scheme 3; 11)

Acid 6 (0.426 g, 1.18 mmol) was treated with HOBt (0.19 g, 1.45 mmol), EDCI (0.27 g, 1.45 mmol) and 5 (prepared by debenzylation of 3 (0.432 g 1.18 mmol) with 10% Pd—C (43 mg) according to GP-1) according to GP-5 and purified by column chromatography (60–120 mesh Silica-gel, 50% EtOAc-pet ether) to give 11 (0.545 g, 75%) as a white solid, M.p. 75–78° C.; $[\alpha]_D$=−48.21 (c 0.5, $CHCl_3$), IR (KBr): 3365, 2985, 2941, 1741, 1686, 1520, 1365, 1164, 1075, 1012 $cm^{-1}$; $^1$H-NMR (500 MHz, $CDCl_3$) δ 6.36 (d, J=8.2 Hz, 1H, $S_2$—NH), 5.99 (d, J=3.9 Hz, 1H, $C_1$H), 5.91 (d, J=3.9 Hz, 1H, $C_1$H), 5.60 (d, J=8.1 Hz, 1H, $S_1$—NH), 4.60 (m, 1H, $C_\beta$H), 4.59 (d, J=3.9 Hz, 1H, $C_2$H), 4.58 (d, J=3.9 Hz, 1H, $C_2$H), 4.35 (m, 1H, $C_4$H), 4.21 (m, 1H, $C_\beta$H), 4.21 (m, 1H, $C_4$H), 3.82 (d, J=3.3 Hz, 1H, $C_3$H), 3.75 (d, J=3.3 Hz, 1H, $C_3$H), 3.68 (s, 3H, —COOMe), 3.41 (s, 3H, —OMe), 3.38 (s, 3H, OMe), 2.68 (dd, 1H, J=7.3, 15.6 Hz, $C_\alpha$H'), 2.61 (dd, J=5.3, 15.6 Hz, 1H, $C_\alpha$H), 2.44 (dd, J=4.7, 14.1 Hz, 1H, C$\alpha$H'), 2.36 (dd, J=4.1, 14.1 Hz, $C_\alpha$H), 1.48 (s, 3H, Me), 1.46 (s, 3H, Me), 1.44 (s, 9H, -Boc), 1.32 (s, 3H, Me), 1.30 (s, 3H, Me). FAB MS: 619.2 ($M^+$+H)

Part 2: Boc Deprotectin of Dipeptide (Scheme 3; 12)

Boc deprotection of 11 (0.67 g, 1.08 mmol) with TFA (0.7 mL) in $CH_2Cl_2$ (7 mL) was performed according to GP-4 to give the amine salt 12.

Part 3: Ester Hydrolysis of Dipeptide (Scheme 3; 13)

Hydrolysis of ester 11 (0.40 g, 0.65 mmol) with 4N NaOH (2.5 mL) in methanol (2.5 mL) was performed according to GP-3 to give 13 (0.365 g, 94%) as a solid, M.p. 64–66° C.; [α]$_D$=−54.22 (c 0.7, CHCl$_3$), IR (KBr): 3365, 2986, 2940, 1723, 1678, 1519, 1368, 1166, 1074, 1015 cm$^{-1}$; $^1$H-NMR (500 MHz, DMSO-d6) δ 7.79 (d, J=8.7 Hz, 1H, S$_2$—NH), 6.26 (d, J=8.1 Hz, 1H, S$_1$—NH), 5.78 (d, J=3.9 Hz, 1H, C$_1$H), 5.75 (d, J=3.9 Hz, 1H, C$_1$H), 4.63 (d, J=3.9 Hz, 1H, C$_2$H), 4.61 (d, J=3.9 Hz, 1H, C$_2$H), 4.3 (m, 1H, C$_β$H), 4.19 (m, 1H, C$_4$H), 4.04 (m, 1H, C$_4$H), 3.96 (m, 1H, C$_β$H), 3.63 (d, J=3.3 Hz, 1H, C$_3$H), 3.59 (d, J=3.3 Hz, 1H, C$_3$H), 3.30 (s, 3H, OMe), 3.29 (s, 3H, OMe), 2.34 (m, 2H, C$_α$H',H), 2.21(m, 2H, C$_α$H',H), 1.48 (s, 3H, Me), 1.46 (s, 3H, Me), 1.44 (s, 9H, -Boc), 1.32 (s, 3H, Me), 1.30 (s, 3H, Me). FAB MS: 605 (M$^+$+H)

Part 4: Preparation of Tetrapeptide (Scheme 3; 14)

Acid 12 (0.655 g, 1.08 mmol) was treated with HOBt (0.176 g, 1.30 mmol), EDCI (0.25 g, 1.30 mmol), 13 (prepared by Boc deprotection of 11 (0.67 g, 1.08 mmol) with TFA (0.7 mL) in CH$_2$Cl$_2$ (7 mL) according to GP-4) and DIPEA (0.45 mL, 1.63 mmol) according to GP-7 and purified by column chromatography (60–120 mesh Silica-gel, 2.0% Methanol-CHCl$_3$) to give 14 (0.9 g, 75%) as a white solid, M.p. 124–126° C.; [α]$_D$=−36.79 (c 0.25, CHCl$_3$), IR (KBr): 3372, 3392.5, 2982, 2933, 1671, 1530, 1369.5, 1169, 1070, 1012 cm$^{-1}$; $^1$H-NMR (500 MHz, CDCl$_3$) δ 6.81 (d, J=7.9 Hz, 1H, S$_4$—NH), 6.79 (d, J=7.9 Hz, 1H, S$_3$—NH), 6.57 (d, J=7.9 Hz, 1H, S$_2$—NH), 5.92 (d, J=3.9 Hz, 1H, C$_1$H), 5.895 (d, J=3.9 Hz, 1H, C$_1$H), 5.89 (d, J=3.9 Hz, 1H, C$_1$H), 5.88 (d, J=3.9 Hz, 1H, C$_1$H), 5.58 (d, J=6.1 Hz, 1H, S$_1$—NH), 4.59 (m, 1H, C$_β$H), 4.57 (d, J=3.9 Hz, 1H, C$_2$H), 4.57 (d, J=3.9 Hz, 1H, C$_2$H), 4.56 (d, J=3.9 Hz, 1H, C$_2$H), 4.56 (d, J=3.9 Hz, 1H, C$_2$H), 4.59 (m, 1H, C$_β$H), 4.53 (m, 1H, C$_β$H), 4.36 (m, 1H, C$_4$H), 4.32 (m, 1H, C$_4$H), 4.29 (m, 1H, C$_4$H), 4.25 (m, 1H, C$_β$H), 4.25 (m, 1H, C$_4$H), 3.86 (d, J=3.1 Hz, 1H, C$_3$H), 3.80 (d, J=2.9 Hz, 1H, C$_3$H), 3.78 (d, J=3.0 Hz, 1H, C$_3$H), 3.68 (s, 3H, —COOMe), 3.67 (d, J=3.1 Hz, 1H, C$_3$H), 3.40 (s, 3H, OMe), 3.39 (s, 3H, OMe), 3.38 (s, 3H, OMe), 3.37 (s, 3H, OMe), 2.67 (dd, J=5.8, 15.6 Hz, 1H, C$_α$H'), 2.59 (dd, J=5.8, 15.6 Hz, 1H, C$_α$H), 2.46 (m, 2H, C$_α$H,H'), 2.43 (m, 2H, C$_α$H,H'), 2.42 (m, 2H, C$_α$H,H'), 1.47 (s, 3H, Me), 1.465 (s, 3H, Me),1.46 (s, 6H, 2-Me), 1.43 (s, 9H, -Boc), 1.31 (s, 3H, Me), 1.302 (s, 3H, Me), 1.30 (s, 6H, 2-Me). FAB MS: 1105.1 (M$^+$+H)

Part 5: Ester Hydrolysis of Tetrapeptide (Scheme 3; 15)

Hydrolysis of ester 14 (0.6 g, 0.54 mmol) with 4N NaOH (2 mL) in methanol (2 mL) was performed according to GP-3 to give 15 (0.42 g, 71%) as a solid, M.p. 141–143° C.; [α]$_D$=−45.72 (c 0.6, CHCl$_3$), IR (KBr): 3397, 2986, 2937.5, 1656, 1527, 1378, 1167, 1080, 1021 cm$^{-1}$; $^1$H-NMR (500 MHz, DMSO-d6) δ 7.88 (d, J=7.9 Hz, 1H, S$_4$—NH), 7.55 (d, J=7.9 Hz, 1H, S$_3$—NH), 7.44 (d, J=7.9 Hz, 1H, S$_2$—NH), 6.25 (d, J=6.1 Hz, 1H, S$_1$—NH), 5.77 (d, J=3.9 Hz, 1H, C$_1$H), 5.76 (d, J=3.9 Hz, 1H, C$_1$H), 5.75 (d, J=3.9 Hz, 1H, C$_1$H), 5.75 (d, J=3.9 Hz, 1H, C$_1$H), 4.65 (d, J=3.9 Hz, 1H, C$_2$H), 4.62 (d, J=3.9 Hz, 1H, C$_2$H), 4.61 (d, J=3.9 Hz, 1H, C$_2$H), 4.60 (d, J=3.9 Hz, 1H, C$_2$H), 4.32 (m, 1H, C$_β$H), 4.31 (m, 1H, C$_β$H), 4.29 (m, 1H, C$_β$H), 4.21 (m, 1H, C$_4$H), 4.16 (m, 1H, C$_4$H), 4.12 (m, 1H, C$_4$H), 4.06 (m, 1H, C$_4$H), 3.98 (m, 1H, C$_β$H),3.69 (d, J=3.1 Hz, 1H, C$_3$H), 3.67 (d, J=2.9 Hz, 1H, C$_3$H), 3.63 (d, J=3.0 Hz, 1H, C$_3$H), 3.62 (s,1H, C$_3$H), 3.30 (s, 6H, OMe), 3.294 (s, 3H, OMe), 3.29 (s, 3H, OMe), 2.35 (m,1H, C$_α$H'), 2.29 (m,1H, C$_α$H), 2.25(m, 2H, C$_α$H,H'), 2.26 (m, 1H, C$_α$H'), 2.23 (m, 1H, C$_α$H), 2.20 (m, 1H, C$_α$H'), 2.17 (m, 1H, C$_α$H'), 1.38 (s, 3H, Me), 1.37 (s, 3H, Me),1.36 (s, 3H, Me), 1.35 (s, 9H, -Boc), 1.35 (s, 3H, Me), 1.24 (s, 3H, Me), 1.232 (s, 3H, Me), 1.224 (s, 6H, 2-Me). FAB MS: 1113.2 (M$^+$+Na)

Part 6: Boc Deprotectin of Tetrapeptide (Scheme 3; 16)

Boc deprotection of 14 (0.101 g, 0.092 mmol) with TFA (0.1 mL) in CH$_2$Cl$_2$ (1.0 mL) according to GP-4 gave 16.

Part 7: Preparation of Hexapeptide (Scheme 3; 17)

Acid 15 (0.15 g, 0.138 mmol) was treated with HOBt (0.023 g, 0.165 mmol), EDCI (0.032 g, 0.165 mmol), 12 (prepared by Boc deprotection of 14 (0.085 g, 0.138 mmol) with TFA (0.1 mL) in CH$_2$Cl$_2$ (1 mL) as described in GP-4) and DIPEA (0.04 mL, 0.207) according to GP-8 and purified by column chromatography (60–120 mesh Silica gel, 2.5% Methanol-CHCl$_3$) to give 17 (0.122 g, 56%) as a white solid, M.p. 140–142° C.; [α]$_D$=−30.46 (c 0.6, CHCl$_3$), IR (KBr): 3377, 2987.5, 2938, 1664, 1528, 1376, 1217, 1166, 1080, 1022 cm$^{-1}$; $^1$H-NMR (500 MHz, CDCl$_3$) δ 6.92 (d, J=7.9 Hz, 1H, S$_5$—NH), 6.86 (d, J=7.9 Hz, 1H, S$_6$—NH), 6.85 (d, J=7.9 Hz, 1H, S$_4$—NH), 6.71 (d, J=7.9 Hz, 1H, S$_3$—NH), 6.58(d, J=7.9 Hz, 1H, S$_2$—NH), 5.92 (d, J=3.9 Hz, 1H, C$_1$H), 5.895 (d, J=3.9 Hz, 1H, C$_1$H), 5.89 (d, J=3.9 Hz, 1H, C$_1$H), 5.89 (d, J=3.9 Hz, 1H, C$_1$H), 5.88 (d, J=3.9 Hz, 1H, C$_1$H), 5.64 (d, J=6.1 Hz, 1H, S$_1$—NH), 4.59 (m, 1H, C$_β$H), 4.55 (m, 1H, C$_β$H), 4.57 (d, J=3.9 Hz, 1H, C$_2$H), 4.57 (d, J=3.9 Hz, 1H, C$_2$H), 4.56 (d, J=3.9 Hz, 1H, C$_2$H), 4.56 (d, J=3.9 Hz, 1H, C$_2$H), 4.54 (m,1H, C$_β$H), 4.53 (m, 1H, C$_β$H), 4.50 (m,1H, C$_β$H), 4.38 (m, 1H, C$_4$H), 4.33 (m, 1H, C$_4$H), 4.32 (m, 1H, C$_4$H), 4.31 (m, 1H, C$_4$H), 4.30 (m, 1H, C$_4$H), 4.25 (m, 1H, C$_β$H), 4.25 (m, 1H, C$_4$H), 3.86 (d, J=3.1 Hz, 1H, C$_3$H), 3.82 (d, J=2.9 Hz, 1H, C$_3$H), 3.79 (d, J=2.9, 2H, 2-C$_3$H), 3.77 (d, J=3.0 Hz, 1H, C$_3$H), 3.68 (s, 3H, —COOMe), 3.67 (d, J=3.1, 1H, C$_3$H), 3.40 (s, 6H, 2-OMe), 3.39 (s, 3H, OMe), 3.38 (s, 6H, 2-OMe), 3.37 (s, 3H, OMe), 2.67 (dd, J=5.8, 15.6 Hz, 1H, C$_α$H'), 2.59 (dd, J=5.8, 15.6 Hz, 1H, C$_α$H), 2.46 (m, 2H, C$_α$H,H'), 2.43 (m, 2H, C$_α$H,H'), 2.42 (m, 2H, C$_α$H,H'), 1.474 (s, 3H, Me), 1.465 (s, 3H, Me),1.46 (s, 3H, Me), 1.43 (s, 9H, -Boc), 1.31 (s, 3H, Me), 1.302 (s, 3H, Me), 1.30 (s, 3H, Me). FAB MS: 1592.6 (M$^+$+H)

Part 8: Preparation of Octapeptide (Scheme 3; 18)

Acid 15 (0.10 g, 0.092 mmol) was treated with HOBt (0.015 g, 0.11 mmol), EDCI (0.02 g, 0.11 mmol), 16 (prepared by Boc deprotection of 14 (0.101 g, 0.092 mmol) with TFA (0.1 mL) in CH$_2$Cl$_2$ (1.0 mL) according to GP-4) and DIPEA (0.024 mL, 0.14) according to GP-9 and purified by column chromatography (60–120 mesh Silica-gel, 3.0% Methanol-CHCl$_3$) to give 18 (0.075 g, 39%) as a white solid, M.p. 156–159° C.; [α]$_D$=−25.58 (c 0.45, CHCl$_3$), IR (KBr): 3378, 2992, 2932, 1667, 1564, 1370, 1156, 1068, 1011 cm$^{-1}$; FAB MS: 2078.2 (M$^+$+H)

Part 9: Preparation of Tripeptide (Scheme 3; 19)

Acid 13 (0.335 g, 0.554 mmol) was treated with HOBt (0.090 g, 0.665 mmol), EDCI (0.127 g, 0.665 mmol), 7 prepared by Boc deprotection of 5a (0.208 g, 0.554 mmol) with TFA (0.2 mL) in CH$_2$Cl$_2$ (2.0 mL) according to GP-4) and DIPEA (0.15 mL, 0.831 mmol) according to GP-6 and purified by column chromatography (60–120 mesh Silica-gel, 75% EtOAc-pet. ether) to give 19 (0.380 g, 80%) as a white solid, M.p. 95–98° C.; [α]$_D$=−39.52 (c 0.5, CHCl$_3$), IR (KBr): 3397, 2994, 2935, 1740, 1677, 1521, 1371, 1161, 1074, 1014 cm$^{-1}$; $^1$H-NMR (500 MHz, CDCl3) δ 6.56 (d, J=8.1 Hz, 1H, S$_2$—NH), 6.56 (d, J=8.1 Hz, 1H, S$_3$—NH), 5.92 (d, J=3.9 Hz, 1H, C$_1$H), 5.91 (d, J=3.9 Hz, 1H, C$_1$H), 5.91 (d, J=3.9 Hz, 1H, C$_1$H), 5.58 (d, J=8.1 Hz, 1H, S$_1$—NH), 4.60 (m, 1H, C$_β$H), 4.57 (d, J=3.9 Hz, 1H, C$_2$H), 4.56 (d, J=3.9 Hz, 1H, C$_2$H), 4.55 (d, J=3.9 Hz, 1H, C$_2$H), 4.55 (m, 1H, C$_β$H), 4.37 (m, 1H, C$_4$H), 4.35 (m, 1H, C$_4$H), 4.25 (m, 1H, C$_β$H), 4.25 (m, 1H, C$_4$H), 3.85 (d, J=3.3 Hz, 1H, C$_3$H), 3.79 (d, J=3.3 Hz, 1H, C$_3$H), 3.75 (d, J=3.3 Hz, 1H, C$_3$H), 3.68 (s, 3H, —COOMe), 3.40 (s, 3H, OMe), 3.39 (s, 3H, OMe), 3.38 (s, 3H, OMe), 2.67 (m, 1H, C$_α$H'), 2.58 (m, 1H, C$_α$H), 2.46 (m, 1H, C$_α$H'), 2.41 (m, 1H, C$_α$H',H), 2.38 (m,1H, C$_α$H),1.49 (s, 3H, Me), 1.47 (s, 3H, Me), 1.47 (s, 3H, Me), 1.43 (s, 9H, -Boc), 1.32 (s, 3H, Me), 1.30 (s, 3H, 2-Me). FAB MS: 884 (M$^+$+Na)

EXAMPLE-3

Part 1: Preparation of Dipeptide (Scheme 4; 20)

Acid 6 (1.2 g, 3.32 mmol) was treated with HOBt (0.54 g, 4 mmol), EDCI (0.765 g, 4 mmol) and 8 (prepared by debenzylation of 4 (1.21 g 3.32 mmol) with 10% Pd—C (0.12 g) according to GP-1) according to GP-5 and purified by column chromatography (60–120 mesh Silica-gel, 50% EtOAc-pet ether) to give 20 (1.55 g, 76%) as a white solid, M.p. 73–76° C.; $[\alpha]_D = -37.414$ (c 0.46, CHCl$_3$), IR (KBr): 3391, 2975, 2934, 1740, 1690, 1648, 1528, 1372, 1170, 1074, 1015 cm$^{-1}$; $^1$H-NMR (500 MHz, CDCl$_3$) δ 6.70 (d, J=8.9 Hz, 1H, R$_2$—NH), 5.92 (d, J=3.8 Hz, 1H, C$_1$H), 5.89 (d, J=3.8 Hz, 1H, C$_1$H), 5.23 (d, J=7.5 Hz, 1H, S$_1$—NH), 4.7 (dddd, J=8.9, 7.7, 6.3, 5.3 Hz, 1H, C$_\beta$H), 4.57 (d, J=3.8 Hz, 1H, C$_2$H), 4.54 (d, J=3.8 Hz, 1H, C$_2$H), 4.31 (dd, J=7.7, 3.2 Hz, 1H, C$_4$H), 4.29 (dd, J=6.5, 3.2 Hz, 1H, C$_4$H), 4.16 (dddd, J=7.5, 6.5, 5.6, 5.4 Hz, 1H, C$_\beta$H), 3.75 (d, J=3.2 Hz, 1H, C$_3$H), 3.73 (d, J=3.2 Hz, 1H, C$_3$H), 3.68 (s, 3H, COOMe), 3.41 (s, 3H, OMe), 3.37 (s, 3H, OMe), 2.69 (dd, J=6.3, 15.9 Hz, 1H, C$_\alpha$H'), 2.62 (dd, J=5.3, 15.9 Hz, 1H, C$_\alpha$H), 2.52 (dd, J=5.4, 14.9 Hz, C$_\alpha$H), 2.41 (dd, J=5.6, 14.9 Hz, C$_\alpha$H), 1.48 (s, 3H, Me), 1.47 (s, 3H, Me), 1.43 (s, 9H, -Boc), 1.314 (s, 3H, Me), 1.31 (s, 3H, Me). FAB MS: 619.3 (M$^+$+H)

Part 2: Boc Deprotectin of Dipetide (Scheme 4; 21)

Boc deprotection of 20 (0.42 g, 0.68 mmol) with TFA (0.4 mL) in CH$_2$Cl$_2$ (4 mL) was performed according to GP-4 to give the amine salt 21.

Part 3: Ester Hydrolysis of Dipeptide (Scheme 4; 22)

Hydrolysis of ester 20 (1.05 g, 1.7 mmol) with 4N NaOH (6.7 mL) in methanol (6.7 mL) was performed accorxling to GP-3 to give 22 (0.86 g, 84%) as a solid, M.p. 107–109° C.; $[\alpha]_D = -38.709$ (c 0.41, CHCl$_3$), IR (KBr): 3374, 2980, 2939.5, 1705, 1662, 1529, 1370.5, 1161, 1079, 1011 cm$^{-1}$; $^1$H-NMR (500 MHz, CDCl$_3$) δ 7.02 (d, J=8.5 Hz, 1H, R$_2$—NH), 5.90 (d, J=3.8 Hz, 1H, C$_1$H), 5.89 (d, J=3.8 Hz, 1H, C$_1$H), 5.27 (d, J=7.7 Hz, 1H, S$_1$—NH), 4.67 (m, 1H, C$_\beta$H), 4.58 (d, J=3.8 Hz, 1H, C$_2$H), 4.55 (d, J=3.8 Hz, 1H, C$_2$H), 4.34 (dd, J=6.6, 3.1 Hz, 1H, C$_4$H), 4.28 (dd, J=8.0, 3.1 Hz, 1H, C$_4$H), 4.16 (dddd, J=8.0, 7.7, 6.2, 5.2 Hz, 1H, C$_\beta$H), 3.78 (d, J=3.1 Hz, 1H, C$_3$H), 3.73 (d, J=3.1 Hz, 1H, C$_3$H), 3.41(s, 3H, OMe), 3.38 (s, 3H, OMe), 2.71 (m, 2H, C$_\alpha$H, C$_\alpha$H'), 2.53 (dd, J= 5.2, 14.9 Hz, 1H, C$_\alpha$H'), 2.43 (dd, J=6.2, 14.9 Hz, C$_\alpha$H), 1.48 (s, 3H, Me), 1.47 (s, 3H, Me), 1.43 (s, 9H, -Boc), 1.31 (s, 6H, Me). FAB MS: 605.2 (M$^+$+H)

Part 4: Preparation of Tetrapeptide (Scheme 4; 23)

Acid 22 (0.41 g, 0.68 mmol) was treated with HOBt (0.11 g, 0.82 mmol), EDCI (0.16 g, 0.82 mmol), 21 (prepared by Boc deprotection of 20 (0.42 g, 0.68 mmol) with TFA (0.4 mL) in CH$_2$Cl$_2$ (4 mL) according to GP-4) and DIPEA (0.18 mL, 1.02 mmol) according to GP-7 and purified by column chromatography (60–120 mesh Silica-gel, 1.5% Methanol-CHCl$_3$) to give 23 (0.57 g, 76%) as a white solid, M.p. 124–127° C.; $[\alpha]_D = -15.18$ (c 0.3, CHCl$_3$), IR (KBr): 3366, 3286, 2987, 2936, 1718, 1655, 1541, 1374, 1211, 1166, 1081, 1021 cm$^{-1}$; $^1$H-NMR (500 MHz, CDCl$_3$) δ 8.16 (d, J=8.2 Hz, 1H, R$_4$—NH), 7.06 (d, J=9.1 Hz, 1H, S$_3$—NH), 6.76 (d, J=10.0 Hz, 1H, R$_2$—NH), 5.91 (d, J=8.9 Hz, 1H, S$_1$—NH), 5.89 (d, J=4.0 Hz, 1H, C$_1$H), 5.88 (d, J=3.7 Hz, 1H, C$_1$H), 5.87 (d, J=3.7 Hz, 1H, C$_1$H), 5.87 (d, J=3.7 Hz, 1H, C$_1$H), 4.84 (M, 1H, C$_\beta$H), 4.63 (m, 1H, C$_\beta$H), 4.57 (d, J=4.0 Hz, 1H, C$_2$H), 4.55 (d, J=3.7 Hz, 1H, C$_2$H), 4.53 (d, J=3.7 Hz, 1H, C$_2$H), 4.51 (d, J=4.0 Hz, 1H, C$_2$H), 4.41 (m, 1H, C$_\beta$H), 4.36 (dd, J=3.8, 8.8 Hz, 1H, C$_4$H), 4.29 (dd, J=3.1, 9.9 Hz, 1H, C$_4$H), 4.14 (m, 1H, C$_\beta$H), 4.13 (dd, J=2.8, 9.4 Hz, 1H, C$_4$H), 4.11 (dd, J=3.4, 6.2 Hz, 1H, C$_4$H), 4.09 (d, J=3.1 Hz, 1H, C$_3$H), 3.80 (d, J=2.9 Hz, 1H, C$_3$H), 3.78 (d, J=3.4 Hz, 1H, C$_3$H), 3.73 (d, J=3.4 Hz, 1H, C$_3$H), 3.66 (s, 3H, —COOMe), 3.41 (s, 3H, OMe), 3.37 (s, 3H, OMe), 3.37 (s, 3H, OMe), 3.36 (s, 3H, OMe), 2.83 (dd, J=3.2, 12.9 Hz, 1H, C$_\alpha$H), 2.66 (dd, J=2.3, 12.7 Hz, 1H, C$_\alpha$H), 2.51 (dd, J=9.7, 12.9 Hz, 1H, C$_\alpha$H), 2.44 (dd, J=5.3, 13.0 Hz, 1H, C$_\alpha$H), 2.43 (dd, J=4.1, 12.8 Hz, 1H, C$_\alpha$H'), 2.41 (dd, J=5.2, 12.8 Hz, 1H, C$_\alpha$H'), 2.18 (dd, J=3.6, 13.0 Hz, 1H, C$_\alpha$H'), 2.13 (dd, J=10.9, 12.7 Hz, 1H, C$_\alpha$H'), 1.49 (s, 3H, Me), 1.44 (s, 3H, Me), 1.44 (s, 9H, Boc), 1.43 (s, 3H, Me), 1.30 (s, 3H, Me), 1.30 (s, 3H, Me), 1.30 (s, 3H, Me), 1.29 (s, 3H, Me), 1.26 (s, 3H, Me). FAB MS: 1105.3 (M$^+$+H)

Part 5: Ester Hydrolysis of Tetrapeptide (Scheme 4; 24)

Hydrolysis of ester 23 (0.35 g, 0.32 mmol) with 4N NaOH (1.2 mL) in methanol (1.2 mL) was performed according to GP-3 to give 24 (0.30 g, 88%) as a solid, M.p. 139–142° C.; $[\alpha]_D = -33.552$ (c 0.4, CHCl$_3$), IR (KBr): 3344, 2988, 2938, 1718.5, 1663, 1527, 1376, 1217, 1166, 1081, 1020 cm$^{-1}$; $^1$H-NMR (500 MHz, CDCl$_3$) δ 7.65 (d, J=8.2 Hz, 1H, R$_4$—NH), 7.23 (d, J=9.1 Hz, 1H, S$_3$—NH), 6.99 (d, J=10.0 Hz, 1H, R$_2$—NH), 5.90 (d, J=3.9 Hz, 1H, C$_1$H), 5.89 (d, J=4.0 Hz, 1H, C$_1$H), 5.88 (d, J=3.7 Hz, 1H, C$_1$H), 5.87 (d, J=3.7 Hz, 1H, C$_1$H), 5.64 (d, J=9.5 Hz, 1H, S$_1$—NH), 4.70 (m, 1H, C$_\beta$H), 4.69 (m, 1H, C$_\beta$H), 4.59 (d, J=4.0 Hz, 1H, C$_2$H), 4.56 (d, J=3.7 Hz, 1H, C$_2$H), 4.55 (d, J=3.7 Hz, 1H, C$_2$H), 4.54 (d, J=4.0 Hz, 1H, C$_2$H), 4.45 (m, 1H, C$_\beta$H), 4.35 (dd, J=3.8, 8.8 Hz, 1H, C$_4$H), 4.31 (dd, J=3.1, 9.9 Hz, 1H, C$_4$H), 4.29 (dd, J=3.1, 9.9 Hz, 1H, C$_4$H), 4.26 (dd, J=2.8, 9.4 Hz, 1H, C$_4$H), 4.17 (m, 1H, C$_\beta$H), 3.97 (d, J=3.1 Hz, 1H, C$_3$H), 3.85 (d, J=2.9 Hz, 1H, C$_3$H), 3.79 (d, J=3.4 Hz, 1H, C$_3$H), 3.75 (d, J=3.4 Hz, 1H, C$_3$H), 3.41 (s, 3H, OMe), 3.39 (s, 3H, OMe), 3.38 (s, 3H, OMe), 3.36 (s, 3H, OMe), 2.81 (dd, J=3.2, 12.9 Hz, 1H, C$_\alpha$H), 2.62 (dd, J=2.3, 12.7 Hz, 1H, C$_\alpha$H), 2.52 (dd, J=9.7, 12.9 Hz, 1H, C$_\alpha$H'), 2.51 (dd, J=5.3, 13.0 Hz, 1H, C$_\alpha$H), 2.48 (dd, J=4.1, 12.8 Hz, 1H, C$_\alpha$H), 2.46 (dd, J=5.2, 12.8 Hz, 1H, C$_\alpha$H'), 2.36 (dd, J=3.6, 13.0 Hz, 1H, C$_\alpha$H'), 2.28 (dd, J=3.6, 13.0 Hz, 1H, C$_\alpha$H), 1.49 (s, 3H, Me), 1.486 (s, 3H, Me), 1.48 (s, 3H, Me), 1.46 (s, 3H, Me), 1.44 (s, 9H, Boc), 1.31 (s, 6H, 2×Me); 1.302 (s, 3H, Me), 1.30 (s, 3H, Me). FAB MS: 1113.2 (M$^+$+Na)

Part 6: Boc Deprotectin of Tetrapetide (Scheme 4; 25)

Boc deprotection of 24 (0.16 g, 0.14 mmol) with TFA (0.15 mL) in CH$_2$Cl$_2$ (1.5 mL) according to GP-4 gave 25.

Part 7: Preparation of Hexapeptide (Scheme 4; 26)

Acid 24 (0.1 g, 0.09 mmol) was treated with HOBt (0.015 g, 0.11 mmol), EDCI (0.022 g, 0.11 mmol), 21 (prepared by Boc deprotection of 20 (0.057 g, 0.09 mmol) with TFA (0.1 mL) in CH$_2$Cl$_2$ (1 mL) as described in GP-4) and DIPEA (0.03 mL, 0.14 mmol) according to GP-8 and purified by column chromatography (60–120 mesh Silica gel, 2.0% Methanol-CHCl$_3$) to give 26 (0.085 g, 58%) as a white solid, M.p. 114–116° C.; $[\alpha]_D = +7.59$ (c 0.35, CHCl$_3$), IR (KBr): 3381, 2986, 2934, 1716, 1651, 1557.5, 1374, 1166, 1081, 1022 cm$^{-1}$; $^1$H-NMR (500 MHz, CDCl$_3$) δ 8.75 (d, J=9.6 Hz, 1H, R$_4$—NH), 8.62 (d, J=9.6 Hz, 1H, R$_6$—NH) 7.69 (d, J=9.9 Hz, 1H, S$_3$—NH), 7.30 (d, J=8.7 Hz, 1H, S$_5$—NH), 6.71 (d, J=10.2 Hz, 1H, R$_2$—NH), 6.10 (d, J=7.3 Hz, 1H, S$_1$—NH), 5.94 (d, J=3.8 Hz, 1H, C$_1$H), 5.89 (d, J=3.7 Hz, 1H, C$_1$H), 5.88 (d, J=4.0 Hz, 1H, C$_1$H), 5.87 (d, J=3.7 Hz, 1H, C$_1$H), 5.79 (d, J=3.8 Hz, 1H, C$_1$H), 5.78 (d, J=3.8 Hz, 1H, C$_1$H), 5.10 (m, 1H, C$_\beta$H), 4.70 (m, 1H, C$_\beta$H), 4.60 (m, 1H, C$_\beta$H), 4.59 (d, J=3.7 Hz, 1H, C$_2$H), 4.55 (d, J=4.0 Hz, 1H, C$_2$H), 4.53 (d, J=3.8 Hz, 1H, C$_2$H), 4.53 (d, J=3.7 Hz, 1H, C$_2$H), 4.50 (d, J=3.8 Hz, 1H, C$_2$H), 4.49 (d, J=3.8 Hz, 1H, C$_2$H), 4.41 (m, 1H, C$_\beta$H), 4.35 (dd, J=3.2, 10.2 Hz, 1H, C$_4$H), 4.33 (dd, J=3.2, 10.7 Hz, 1H, C$_4$H), 4.27 (dd, J=2.9, 9.0 Hz, 1H, C$_4$H), 4.24 (m, 1H, C$_\beta$H), 4.18 (dd, J=2.8, 10.0 Hz, 1H, C$_4$H), 4.15 (m, 1H, C$_\beta$H), 4.13 (d, J=3.2 Hz, 1H, C$_3$H), 4.13 (dd, J=3.2, 4.6 Hz, 1H, C$_4$H), 4.12 (d, J=3.2 Hz, 1H, C$_3$H), 4.07 (dd, J=3.0, 9.8 Hz, 1H, C$_4$H), 3.78 (d, J=2.9 Hz, 1H, C$_3$H), 3.77 (d, J=2.8 Hz, 1H, C$_3$H), 3.70 (d, J=3.2, 1H, C$_3$H), 3.68 (d, J=3.0, 1H, C$_3$H), 3.64 (s, 3H, —COOMe), 3.40 (s, 3H, OMe), 3.39 (s, 3H, OMe), 3.38 (s, 3H, OMe), 3.36 (s, 3H, OMe), 3.35 (s, 3H, OMe), 3.32 (s, 3H, OMe), 2.83 (dd, J=2.6, 12.9 Hz, 1H, C$_\alpha$H'), 2.77 (dd, J=3.0, 12.4 Hz, 1H, C$_\alpha$H'), 2.76 (dd, J=2.0, 12.4 Hz, 1H, C$_\alpha$H'), 2.55 (dd, J=12.3, 12.4 Hz, 1H, C$_\alpha$H), 2.45 (dd, J=5.0, 14.1 Hz, 1H, C$_\alpha$H), 2.43 (dd, J=*, 13.1 1H, C$_\alpha$H), 2.42 (dd, J=5.0, 12.7 Hz, 1H, C$_\alpha$H), 2.34 (dd, J=4.1, 14.1 Hz, 1H, C$_\alpha$H'), 2.28 (dd, J=12.3, 12.9 Hz, 1H, C$_\alpha$H), 2.19 (dd, J=2.6, 13.1 Hz, 1H, C$_\alpha$H'), 2.07 (dd, J=2.8, 12.7 Hz, 1H, C$_\alpha$H'), 2.02 (dd, J=12.1, 12.4 Hz, 1H, C$_\alpha$H), 1.47 (s, 3H, Me), 1.45(s, 9H, Boc), 1.45 (s, 3H, Me), 1.45 (s, 3H, Me), 1.45 (s, 3H, Me), 1.43 (s, 3H, Me), 1.43 (s, 3H, Me), 1.37 (s, 3H, Me), 1.29 (s, 3H, Me), 1.28 (s, 3H, Me), 1.28 (s, 3H, Me), 1.28 (s, 3H, Me), 1.26 (s, 3H, Me). FAB MS: 1592.6 (M$^+$+H)

Part 8: Preparation of Octapeptide (Scheme 4; 27)

Acid 24 (0.15 g, 0.14 mmol) was treated with HOBt (0.022 g, 0.17 mmol), EDCI (0.032 g, 0.17 mmol), 25 (prepared by Boc deprotection of 23 (0.16 g, 0.14 mmol) with TFA (0.16 mL) in CH$_2$Cl$_2$ (1.5 mL) according to GP-4) and DIPEA (0.04 mL, 0.20 mmol) according to GP-9 and purified by column chromatography (60–120 mesh Silica-gel, 2.5% Methanol-CHCl$_3$) to give 27 (0.112 g, 39%) as a white solid, M.p. 166–169° C.; [α]$_D$=+4.851 (c 0.35, CHCl$_3$), IR (KBr): 3383, 2986, 2935, 1718, 1649, 1539, 1376.5, 1166, 1081, 1022 cm$^{-1}$; $^1$H-NMR (500 MHz, CDCl$_3$) δ 9.00 (d, J=9.7 Hz, 1H, R$_6$—NH), 8.692 (d, J=9.7 Hz, 1H, R$_4$—NH), 8.616 (d, J=9.7 Hz, 1H, R$_8$—NH), 8.124 (d, J=9.1 Hz, 1H, S$_5$—NH), 7.75 (d, J=9.7 Hz, 1H, S$_3$—NH), 7.16 (d, J=8.7 Hz, 1H, S$_7$—NH), 6.66 (d, J=9.7 Hz, 1H, R$_2$—NH), 6.18 (d, J=8.7 Hz, 1H, S$_1$—NH), 5.94 (d, J=3.8 Hz, 1H, C$_1$H), 5.89 (d, J=3.7 Hz, 1H, C$_1$H), 5.88 (d, J=4.0 Hz, 1H, C$_1$H), 5.87 (d, J=3.7 Hz, 1H, C$_1$H), 5.86 (d, J=3.7 Hz, 1H, C$_1$H), 5.85 (d, J=3.7 Hz, 1H, C$_1$H), 5.81 (d, J=3.8 Hz, 1H, C$_1$H), 5.79 (d, J=3.8 Hz, 1H, C$_1$H), 5.06 (m, 1H, C$_\beta$H), 4.73 (m, 1H, C$_\beta$H), 4.72 (m, 1H, C$_\beta$H), 4.56 (d, J=3.7 Hz, 1H, C$_2$H), 4.55 (m, 1H, C$_\beta$H), 4.55 (d, J=3.7 Hz, 1H, C$_2$H), 4.555 (d, J=4.0 Hz, 1H, C$_2$H), 4.555 (d, J=3.8 Hz, 1H, C$_2$H), 4.52 (d, J=3.7 Hz, 1H, C$_2$H), 4.52 (d, J=3.8 Hz, 1H, C$_2$H), 4.51 (d, J=3.8 Hz, 1H, C$_2$H), 4.51 (d, J=3.8 Hz, 1H, C$_2$H), 4.39 (m, 1H, C$_\beta$H), 4.35 (dd, J=3.2, 10.2 Hz, 1H, C$_4$H), 4.33 (m, 1H, C$_\beta$H), 4.30 (dd, J=3.2, 10.7 Hz, 1H, C$_4$H), 4.32 (dd, J=3.0, 9.5 Hz, 1H, C$_4$H), 4.31 (dd, J=3.1, 10.5 Hz, 1H, C$_4$H), 4.27 (m, 1H, C$_\beta$H), 4.17 (d, J=3.1 Hz, 1H, C$_3$H), 4.15 (dd, J=2.9 , 10.2 Hz, 1H, C$_4$H), 4.14 (m, 1H, C$_\beta$H), 4.14 (dd, J=3.0, 9.7 Hz, 1H, C$_4$H), 4.13 (dd, J=3.1, 6.5 Hz, 1H, C$_4$H), 4.17 (d, J=3.2 Hz, 1H, C$_3$H), 4.11 (d, J=3.1 Hz, 1H, C$_3$H), 4.10 (d, J=3.1 Hz, 1H, C$_3$H), 4.06 (dd, J=3.1, 11.9 Hz, 1H, C$_4$H), 3.81 (d, J=3.2 Hz, 1H, C$_3$H), 3.723 (d, J=3.0 Hz, 1H, C$_3$H), 3.72 (d, J=2.9 Hz, 1H, C$_3$H), 3.69 (d, J=3.1 Hz, 1H, C$_3$H), 3.65 (d, J=3.1 Hz, 3H, C$_3$H), 3.65 (s, 3H, —COOMe), 3.40 (s, 3H, OMe), 3.39 (s, 3H, OMe), 3.37 (s, 3H, OMe), 3.366 (s, 6H, 2-OMe), 3.344 (s, 3H, OMe), 3.34 (s, 3H, OMe), 3.32 (s, 3H, OMe), 2.93(dd, J=2.2, 12.8 Hz, 1H, C$_\alpha$H'), 2.8 (dd, J=1.7, 12.8 Hz, 1H, C$_\alpha$H'), 2.768 (dd, J=2.7, 12.9 Hz, 1H, C$_\alpha$H'), 2.74 (dd, J=2.3, 12.8 Hz, 1H, C$_\alpha$H'), 2.6 (dd, J=2.4, 12.9 Hz, 1H, C$_\alpha$H'), 2.49 (dd, J=2.4, 12.7 Hz, 1H, C$_\alpha$H'), 2.47 (dd, J=2.7, 12.8 Hz, 1H, C$_\alpha$H), 2.45 (dd, J=4.3, 13.8 Hz, 1H, C$_\alpha$H), 2.44 (dd, J=5.4, 12.8 Hz, 1H, C$_\alpha$H), 2.4 (dd, J=5.7, 12.8 Hz, 1H, C$_\alpha$H), 2.33 (dd, J=5.3, 13.8 Hz, 1H, C$_\alpha$H'), 2.26 (dd, J=2.3, 12.8 Hz, 1H, C$_\alpha$H), 2.18 (dd, J=2.3, 12.8 Hz, 1H, C$_\alpha$H), 2.13 (dd, J=2.4, 12.8 Hz, 1H, C$_\alpha$H'), 2.08 (dd, J=4.3, 12.7 Hz, 1H, C$_\alpha$H'), 2.01 (dd, J=11.7, 12.8 Hz, 1H, C$_\alpha$H), 1.47 (s, 6H, 2-Me), 1.45(s, 9H, Boc), 1.42 (s, 3H, Me), 1.41 (s, 3H, Me), 1.36 (s, 6H, 2-Me), 1.30 (s, 6H, 2-Me), 1.284 (s, 3H, Me), 1.28 (s, 6H, 2-Me), 1.25 (s, 3H, Me), 1.26 (s, 6H, 2-Me). FAB MS: 2078.8 (M$^+$+H)

Part 9: Preparation of Tripeptide (Scheme 4; 28)

Acid 22 (0.4 g, 0.66 mmol) was treated with HOBt (0.107 g, 0.8 mmol), EDCI (0.152 g, 0.8 mmol), 7 (prepared by Boc deprotection of 5a (0.248 g, 0.66 mmol) with TFA (0.25 mL) in CH$_2$Cl$_2$ (2.5 mL) according to GP-4) and DIPEA (0.17 mL, 0.99 mmol) according to GP-6 and purified by column chromatography (60–120 mesh Silica-gel, 70% EtOAc-pet. ether) to give 28 (0.46 g, 81%) as a white solid, M.p. 92–95° C.; [α]$_D$=−41.06 (c 0.4, CHCl$_3$), IR (KBr): 3396, 2985, 2933, 1725, 1669, 1534, 1380, 1169, 1074.5, 1004 cm$^{-1}$; $^1$H-NMR (500 MHz, CDCl$_3$) δ 7.035 (d, J=8.3 Hz, 1H, S$_3$—NH), 7.033 (d, J=8.3 Hz, 1H, R$_2$—NH), 5.91 (d, J=3.8 Hz, 1H, C$_1$H), 5.90 (d, J=3.8 Hz, 1H, C$_1$H), 5.89 (d, J=3.8 Hz, 1H, C$_1$H), 5.42 (d, J=8.2 Hz, 1H, S$_1$—NH), 4.64 (m, 1H, C$_\beta$H), 4.55 (d, J=3.8 Hz, 1H, C$_2$H), 4.54 (d, J=3.8 Hz, 1H, C$_2$H), 4.53 (m, 1H, C$_\beta$H), 4.51 (d, J=3.8 Hz, 1H, C$_2$H), 4.43 (dd, J=3.2, 7.6 Hz, 1H, C$_4$H), 4.28 (dd, J=3.2, 7.5 Hz, 1H, C$_4$H), 4.24 (m,1H, C$_\beta$H), 4.24 (dd, J=3.2, 6.8 Hz, 1H, C$_4$H), 3.75 (d, J=3.1 Hz, 1H, C$_3$H), 3.70 (d, J=3.3 Hz, 1H, C$_3$H), 3.68 (s, 3H, —COOMe), 3.67 (d, J=3.2 Hz, 1H, C$_3$H), 3.39 (s, 3H, OMe), 3.37 (s, 3H, OMe), 3.36 (s, 3H, OMe), 2.67 (dd, J=5.1, 15.2 Hz, 1H, C$_\alpha$H'), 2.63 (dd, J=6.7, 15.2 Hz, 1H, C$_\alpha$H), 2.52 (m, 1H, C$_\alpha$H), 2.52 (m, 1H, C$_\alpha$H'), 2.44 (m, 1H, C$_\alpha$H), 2.37 (m, 1H, C$_\alpha$H), 1.49 (s, 3H, Me), 1.47 (s, 6H, 2×Me), 1.43 (s, 9H, -Boc), 1.313 (s, 3H, Me), 1.309 (s, 3H, Me), 1.307 (s, 3H, Me). FAB MS: 884.3 (M$^+$+Na)

EXAMPLE-4

Part 1: Preparation of Dipeptide (Scheme 5; 29)

Acid 9 (0.81 g, 2.24 mmol) was treated with HOBt (0.36 g, 2.7 mmol), EDCI (0.52 g, 2.7 mmol) and 8 (prepared by debenzylation of 4 (0.82 g 2.24 mmol) with 10% Pd—C (0.08 g) according to GP-1) according to GP-5 and purified by column chromatography (60–120 mesh Silica-gel, 50% EtOAc-pet ether) to give 29 (1.1 g, 79%) as a white solid, M.p. 74–77° C.; [α]$_D$=−39.3 (c 0.5, CHCl$_3$), IR (KBr): 3408, 2994, 2939.5, 1718, 1500, 1370, 1161, 1067, 1011 cm$^{-1}$; $^1$H-NMR (500 MHz, CDCl$_3$) δ 6.69 (d, J=8.6 Hz, 1H, R$_2$—NH), 5.88 (d, J=3.9 Hz, 1H, C$_1$H), 5.84 (d, J=3.8 Hz, 1H, C$_1$H), 5.8 (d, J=9.4 Hz, 1H, R$_1$—NH), 4.65 (dddd, J=8.6, 7.3, 5.9, 5.6 Hz, 1H, C$_\beta$H), 4.54 (d, J=3.9 Hz, 1H, C$_2$H), 4.53 (d, J=3.9 Hz, 1H, C$_2$H), 4.33 (dd, J=3.1, 7.3 Hz, 1H, C$_4$H), 4.31 (m, 1H, C$_\beta$H), 4.17 (m, 1H, C$_4$H), 3.73 (d, J=3.1, 1H, C$_3$H), 3.68 (s, 3H, —COOMe), 3.67 (d, J=2.8, C$_3$H), 3.41 (s, 3H, OMe), 3.40 (s, 3H, OMe), 2.75 (dd, J=5.9, 15.6 Hz, 1H, C$_\alpha$H), 2.61 (dd, J=5.6, 15.6 Hz, 1H, C$_\alpha$H'), 2.54 (dd, J=4.5, 14.8 Hz, C$_\alpha$H), 2.46 (dd, J=4.5, 14.8 Hz, 1H, C$_\alpha$H'), 1.47 (s, 3H, Me), 1.46 (s, 3H, Me), 1.43 (s, 9H, -Boc), 1.31 (s, 3H, Me), 1.29 (s, 3H, Me). FAB MS: 619.3 (M$^+$+H)

Part 2: Boc Deprotectin of Dipeptide (Scheme 5; 30)

Boc deprotection of 29 (0.36 g, 0.58 mmol) with TFA (0.3 mL) in CH$_2$Cl$_2$ (3.5 mL) was performed according to GP-4 to give the amine salt 30.

Part 3: Ester Hydrolysis of Dipeptide (Scheme 5; 31)

Hydrolysis of ester 29 (0.5 g, 0.81 mmol) with 4N NaOH (3.2 mL) in methanol (3.2 mL) was performed according to GP-3 to give 31 (0.45 g, 92%) as a solid, M.p. 114–116° C.; [α]$_D$=−27.822 (c 0.5, CHCl$_3$); IR (KBr): 3392, 2991, 2939, 1721, 1515, 1383, 1257, 1167, 1063, 1014 cm$^{-1}$; $^1$H-NMR (500 MHz, CDCl$_3$) δ 6.55 (d, J=8.6 Hz, 1H, R$_2$—NH), 5.99 (d, J=9.6 Hz, 1H, R$_1$—NH), 5.88 (d, J=3.9 Hz, 1H, C$_1$H), 5.84 (d, J=3.8 Hz, 1H, C$_1$H), 4.77 (dddd, J=8.7, 7.3, 5.9, 5.6 Hz, 1H, C$_\beta$H), 4.54 (d, J=3.9 Hz, 1H, C$_2$H), 4.53 (d, J=3.9

Hz, 1H, C$_2$H), 4.35 (m, 1H, C$_\beta$H), 4.26 (dd, J=3.4, 5.8 Hz, 1H, C$_4$H), 4.16 (m, 1H, C$_4$H), 3.76 (d, J=3.1 Hz, 1H, C$_3$H), 3.66 (d, J=2.8 Hz, C$_3$H), 3.41 (s, 3H, OMe), 3.40 (s, 3H, OMe), 2.75 (dd, J=5.9, 15.6 Hz, 1H, C$_\alpha$H), 2.61 (dd, J=5.6, 15.6 Hz, 1H, C$_\alpha$H'), 2.54 (dd, J=4.5, 14.8 Hz, C$_\alpha$H), 2.46 (dd, J=4.5, 14.8 Hz, 1H, C$_\alpha$H'), 1.47 (s, 3H, Me), 1.46 (s, 3H, Me), 1.43 (s, 9H, -Boc), 1.31 (s, 3H, Me), 1.29 (s, 3H, Me). FAB MS: 605.2 (M$^+$+H)

Part 4: Preparation of Tetrapeptide (Scheme 5; 32)

Acid 31 (0.35 g, 0.58 mmol) was treated with HOBt (0.94 g, 0.69 mmol), EDCI (0.13 g, 0.69 mmol), 30 (prepared by Boc deprotection of 29 (0.36 g, 0.58 mmol) with TFA (0.3 mL) in CH$_2$Cl$_2$ (3.5 mL) according to GP-4) and DIPEA (0.12 mL, 0.87 mmol) according to GP-7 and purified by column chromatography (60–120 mesh Silica-gel, 2.0% Methanol-CHCl$_3$) to give 32 (0.47 g, 73.5%) as a white solid, M.p. 195–197° C.; [α]$_D$=−28.98 (c 0.5, CHCl$_3$), IR (KBr): 3394, 3352, 2987, 2935, 1724, 1674, 1526, 1373, 1218, 1166, 1082, 1020 cm$^{-1}$; $^1$H-NMR (500 MHz, CDCl$_3$) δ 7.21 (d, J=7.9 Hz, 1H, R$_3$—NH), 7.11 (d, J=7.9 Hz, 1H, R$_2$—NH), 7.00 (d, J=7.9 Hz, 1H, R$_4$—NH), 5.87 (d, J=3.9 Hz, 1H, C$_1$H), 5.86 (d, J=3.9 Hz, 1H, C$_1$H), 5.86 (d, J=3.9 Hz, 1H, C$_1$H), 5.85 (d, J=3.9 Hz, 1H, C$_1$H), 5.82 (d, J=6.1 Hz, 1H, R$_1$—NH), 4.53 (d, J=3.9 Hz, 1H, C$_2$H), 4.525 (d, J=3.9 Hz, 1H, C$_2$H), 4.52 (d, J=3.9 Hz, 1H, C$_2$H), 4.51 (d, J=3.9 Hz, 1H, C$_2$H), 4.61 (m, 1H, C$_\beta$H), 4.51 (m, 1H, C$_\beta$H), 4.49 (m, 1H, C$_\beta$H), 4.34 (m, 1H, C$_4$H), 4.32 (m, 1H, C$_4$H), 4.30 (m, 1H, C$_\beta$H), 4.30 (m, 1H, C$_4$H), 4.25 (m, 1H, C$_4$H), 3.73 (d, J=3.1 Hz, 1H, C$_3$H), 3.71 (d, J=2.9 Hz, 1H, C$_3$H), 3.70 (d, J=3.0 Hz, 1H, C$_3$H), 3.70 (d, J=3.1 Hz, 1H, C$_3$H), 3.68 (s, 3H, —COOMe), 3.4 (s,3H,—OMe), 3.394 (s, 3H, OMe), 3.392 (s, 3H, OMe), 3.388 (s, 3H, OMe), 2.75 (dd, J=5.8, 15.6 Hz, 1H, C$_\alpha$H'), 2.67 (dd, J=4.2, 15.6 Hz, 1H, C$_\alpha$H), 2.57 (m, 1H, C$_\alpha$H'), 2.54 (m, 1H, C$_\alpha$H'), 2.51 (m, 2H, C$_\alpha$H,H',), 2.49 (m, 1H, C$_\alpha$H'), 2.48 (m, 1H, C$_\alpha$H), 1.462 (s, 6H, 2-Me), 1.46 (s, 3H, Me),1.45 (s, 3H, Me), 1.43 (s, 9H, -Boc), 1.305 (s, 3H, Me), 1.295 (s, 3H, Me), 1.29 (s, 6H, 2-Me). FAB MS: 1105.3 (M$^+$+H)

Part 5: Ester Hydrolysis of Tetrapeptide (Scheme 5; 33)

Hydrolysis of ester 32 (0.2 g, 0.18 mmol) with 4N NaOH (0.7 mL) in methanol (0.7 mL) was performed according to GP-3 to give 33 (0.17 g, 86%) as a solid, M.p. 202–205° C.; [α]$_D$=−27.32 (c 0.51, CHCl$_3$), IR (KBr): 3348, 3010, 2940, 1678, 1647, 1527, 1380, 1166, 1075, 1018 cm$^{-1}$; $^1$H-NMR (500 MHz, CDCl$_3$) δ 7.21 (d, J=7.9 Hz, 1H, R$_3$—NH), 7.11 (d, J=7.9 Hz, 1H, R$_2$—NH), 7.00 (d, J=7.9 Hz, 1H, R$_4$—NH), 5.92(d, J=3.9 Hz, 1H, C$_1$H), 5.895 (d, J=3.9 Hz, 1H, C$_1$H), 5.89 (d, J=3.9 Hz, 1H, C$_1$H), 5.88 (d, J=3.9 Hz, 1H, C$_1$H), 5.82 (d, J=6.1 Hz, 1H, R$_1$—NH), 4.59 (m, 1H, C$_\beta$H), 4.57 (d, J=3.9 Hz, 1H, C$_2$H), 4.57 (d, J=3.9 Hz, 1H, C$_2$H), 4.56 (d, J=3.9 Hz, 1H, C$_2$H), 4.56(d, J=3.9 Hz, 1H, C$_2$H), 4.61 (m, 1H, C$_\beta$H), 4.51 (m, 1H, C$_\beta$H), 4.49 (m, 1H, C$_\beta$H), 4.34 (m, 1H, C$_4$H), 4.32 (m, 1H, C$_4$H), 4.30 (m, 1H, C$_\beta$H), 4.30 (m, 1H, C$_4$H), 4.25 (m, 1H, C$_4$H), 3.73 (d, J=3.1 Hz, 1H, C$_3$H), 3.71 (d, J=2.9 Hz, 1H, C$_3$H), 3.70 (d, J=3.0 Hz, 1H, C$_3$H), 3.70 (d, J=3.1 Hz, 1H, C$_3$H), 3.394 (s, 3H, OMe), 3.392 (s, 3H, OMe), 3.388 (s, 3H, OMe), 3.34 (s, 3H, OMe), 2.73 (dd, J=5.8, 15.6 Hz, 1H, C$_\alpha$H'), 2.67 (dd, J=5.8, 15.6 Hz, 1H, C$_\alpha$H), 2.57 (m, 1H, C$_\alpha$H'), 2.54 (m, 1H, C$_\alpha$H'), 2.51 (m, 2H, C$_\alpha$H,H',), 2.49 (m, 1H, C$_\alpha$H'), 2.48 (m, 1H, C$_\alpha$H), 1.462 (s, 6H, 2-Me), 1.46 (s, 3H, Me),1.45 (s, 3H, Me), 1.43 (s, 9H, -Boc), 1.305 (s, 3H, Me), 1.295 (s, 3H, Me), 1.29 (s, 6H, 2-Me).

Part 6: Preparation of Hexapeptide (Scheme 5; 34)

Acid 33 (0.125 g, 0.115 mmol) was treated with HOBt (0.019 g, 0.14 mmol), EDCI (0.027 g, 0.14 mmol), 30 prepared by Boc deprotection of 29 (0.071 g, 0.115 mmol) with TFA (0.7 mL) in CH$_2$Cl$_2$ (1 mL) as described in GP-4) and DIPEA (0.03 mL, 0.17 mmol) according to GP-8 and purified by column chromatography (60–120 mesh Silica gel, 2.5% Methanol-CHCl$_3$) to give 34 (0.094 g, 51.5%) as a white solid, M.p. 224–227° C.; [α]$_D$=−32.723 (c 0.75, CHCl$_3$), IR (KBr): 3348, 2988, 2935, 1724, 1651, 1525, 1373, 1217.5, 1166, 1082, 1020 cm$^{-1}$; $^1$H-NMR (500 MHz, CDCl$_3$) δ 7.56 (d, J=8.9 Hz, 1H, R$_4$—NH), 7.54 (d, J=8.9 Hz, 1H, R$_2$—NH), 7.34 (d, J=8.9 Hz, 1H, R$_5$—NH), 7.18 (d, J=9.1 Hz, 1H, R$_3$—NH), 7.08 (d, J=9.2 Hz, 1H, R$_6$—NH), 5.92 (d, J=3.9 Hz, 1H, C$_1$H), 5.78 (d, J=3.9 Hz, 1H, C$_1$H), 5.89 (d, J=3.9 Hz, 1H, C$_1$H), 5.88 (d, J=3.9 Hz, 1H, C$_1$H), 5.78 (d, J=9.3 Hz, 1H, R$_1$—NH), 4.60 (m, 1H, C$_\beta$H), 4.47 (m, 1H, C$_\beta$H), 4.46 (m,1H, C$_\beta$H), 4.40 (m, 1H, C$_\beta$H), 4.39 (m, 1H, C$_\beta$H), 4.56(d, J=3.9 Hz, 1H, C$_2$H), 4.51 (d, J=3.9 Hz, 1H, C$_2$H), 4.49 (d, J=3.8 Hz, 1H, C$_2$H), 4.34 (m, 1H, C$_4$H), 4.33 (m, 1H, C$_4$H), 4.33 (m,1H, C$_\beta$H), 4.32 (m, 1H, C$_4$H),4.31(m, 1H, C$_4$H), 3.75 (d, J=3.1 Hz, 1H, C$_3$H), 3.73 (d, J=3.1 Hz, 1H, C$_3$H), 3.69 (m, 3H, 3-H3), 3.68 (s, 3H, —COOMe), 3.70 (d, J=3.1 Hz, 1H, C$_3$H), 3.394 (s, 3H, OMe), 3.392 (s, 3H, OMe), 3.388 (s, 3H, OMe), 3.34 (s, 3H, OMe), 2.73 (dd, J=5.8, 15.6 Hz, 1H, C$_\alpha$H'), 2.67 (dd, J=5.8, 15.6 Hz, 1H, C$_\alpha$H), 2.57 (m, 1H, C$_\alpha$H'), 2.54 (m, 1H, C$_\alpha$H'), 2.51 (m, 2H, C$_\alpha$H, H'), 2.49 (m,1H, C$_\alpha$H'), 2.48 (m,1H, C$_\alpha$H), 1.462 (s, 3H, Me), 1.46 (s, 3H, Me),1.45 (s, 3H, Me), 1.43 (s, 9H, -Boc), 1.305 (s, 3H, Me), 1.295 (s, 3H, Me), 1.29 (s, 6H, 2-Me). FAB MS: 1592.3 (M$^+$+H)

EXAMPLE-5

Part 1: Preparation of Dipeptide (Scheme 6; 35)

Acid 9 (1.65 g, 4.57 mmol) was treated with HOBt (0.74 g, 5.48 mmol), EDCI (1.05 g, 5.48 mmol) and 5 (prepared by debenzylation of 3 (1.67 g 4.57 mmol) with 10% Pd—C (0.16 g) according to GP-1) according to GP-5 and purified by column chromatography (60–120 mesh Silica-gel, 50% EtOAc-pet ether) to give 35 (2.24 g, 79%) as a white solid, M.p. 157–160° C.; [α]$_D$=−40.763 (c 0.49,CHCl3), IR (KBr): 3335, 3269, 2991, 2938, 1730, 1700, 1650, 1526, 1167, 1074, 1013 cm$^{-1}$; $^1$H-NMR (500 MHz, CDCl$_3$) δ 6.48 (d, J=8.3 Hz, 1H, S$_2$—NH), 5.68 (d, J=8.7 Hz, 1H, R$_1$—NH), 5.91 (d, J=3.9 Hz, 1H, C$_1$H), 5.87 (d, J=3.9 Hz, 1H, C$_1$H), 4.59 (m, 1H, C$_\beta$H), 4.55 (d, J=3.9 Hz, 1H, C$_2$H), 4.53 (d, J=3.9Hz, 1H, C$_2$H), 4.37 (m, 1H, C$_4$H), 4.26 (m, 1H, C$_\beta$H), 4.25 (m, 1H, C$_4$H), 3.74 (d, J=3.3, 1H, C$_3$H), 3.73 (d, J=3.3, 1H, C$_3$H), 3.67 (s, 3H, —COOMe), 3.40 (s, 3H, OMe), 3.38 (s, 3H, OMe), 2.71 (dd, 1H, J=6.4, 14.6, C$_\alpha$H'), 2.62 (dd, J=5.9, 14.6, 1H, C$_\alpha$), 2.57 (dd, J=5.2, 15.3, 1H, C$_\alpha$H'), 2.50 (dd, J=4.2, 15.3, C$_\alpha$H), 1.48 (s, 3H, Me), 1.46 (s, 3H, Me), 1.43 (s, 9H, -Boc), 1.31 (s, 3H, Me), 1.30 (s, 3H, Me). FAB MS: 619.1 (M$^+$+H)

Part 2: Boc Deprotectin of Dipeptide (Scheme 6; 36)

Boc deprotection of 35 (0.92 g, 1.4 mmol) with TFA (1.4 mL) in CH$_2$Cl$_2$ (14 mL) was performed according to GP-4 to give the amine salt 36.

Part 3: Ester Hydrolysis of Dipeptide (Scheme 6; 37)

Hydrolysis of ester 35 (1.05 g, 1.7 mmol) with 4N NaOH (6.7 mL) in methanol (6.7 mL) was performed according to GP-3 to give 37 (0.96 g, 92%) as a solid, M.p. 93–95° C.; [α]$_D$=−49.569 (c 0.39, CHCl$_3$), IR (KBr): 3361.5, 2992, 2939, 1707, 1506, 1354, 1159, 1074, 1008 cm$^{-1}$; $^1$H-NMR (500 MHz, CDCl$_3$) δ 6.91 (d, J=7.0 Hz, 1H, S$_2$—NH), 5.53 (d, J=8.8 Hz, 1H, R$_1$—NH), 5.90 (d, J=3.9 Hz, 1H, C$_1$H), 5.89 (d, J=3.9 Hz, 1H, C$_1$H), 4.59 (d, J=3.9 Hz, 1H, C$_2$H), 4.55 (d, J=3.9 Hz, 1H, C$_2$H), 4.34 (m, 1H, C$_\beta$H), 4.33 (m, 1H, C$_4$H), 4.32 (m, 1H, C$_\beta$H), 4.18 (d, J=3.1, 1H, C$_4$H), 3.80 (d, J=3.1, 1H, C$_3$H), 3.75 (d, J=3.1, 1H, C$_3$H), 3.41(s, 3H, OMe), 3.38 (s, 3H, OMe), 2.64 (m, 2H, C$_\alpha$H,H'), 2.60 (dd, J= 3.8, 15.1, 1H, C$_\alpha$H'), 2.48 (dd, J=7.8, 15.1, C$_\alpha$H), 1.50 (s, 3H, Me), 1.47 (s, 3H, Me), 1.43 (s, 9H, -Boc), 1.32 (s, 3H, Me), 1.31 (s, 3H, Me). FAB MS: 605.2 (M$^+$+H)

Part 4: Preparation of Tetrapeptide (Scheme 6; 38)

Acid 37 (0.98 g, 1.5 mmol) was treated with HOBt (0.24 g, 1.8 mmol), EDCI (0.34 g, 1.8 mmol), 36 prepared by Boc deprotection of 35 (0.92 g, 1.5 mmol) with TFA (0.9 mL) in CH$_2$Cl$_2$ (9 mL) according to GP-4) and DIPEA (0.4 mL, 2.23 mmol) according to GP-7 and purified by column chromatography (60–120 mesh Silica-gel, 2% Methanol-CHCl$_3$) to give 38 (1.36 g, 82.7%) as a white solid, M.p. 126–128° C.; [α]$_D$=-2.96 (c 0.54, CHCl3), IR (KBr): 3367, 2987, 2937, 1735, 1668, 1526, 1375, 1217, 1166, 1081, 1021 cm$^{-1}$; $^1$H-NMR (500 MHz, CDCl$_3$) δ 7.89 (d, J=9.6 Hz, 1H, R$_3$—NH), 7.46 (d, J=8.5 Hz, 1H, S$_2$—NH), 6.68 (d, J=8.2 Hz, 1H, S$_4$—NH), 6.04 (d, J=3.9 Hz, 1H, C$_1$H), 5.98 (d, J=4.0 Hz, 1H, C$_1$H), 5.87 (d, J=3.9 Hz, 1H, C$_1$H), 5.86 (d, J=3.9 Hz, 1H, C$_1$H), 5.10 (d, J=10.6 Hz, 1H, R$_1$—NH), 4.72 (m, 1H, C$_\beta$H), 4.57 (d, J=3.9 Hz, 1H, C$_2$H), 4.55 (d, J=3.9 Hz, 1H, C$_2$H), 4.53 (d, J=4.0 Hz, 1H, C$_2$H), 4.51 (d, J=3.9 Hz, 1H, C$_2$H), 4.47 (m, 1H, C$_\beta$H), 4.46 (m, 1H, C$_4$H), 4.41 (m, 1H, C$_\beta$H), 4.40 (m, 1H, C$_\beta$H), 4.31 (dd, J=3.3, 9.8 Hz, 1H, C$_4$H), 4.16 (dd, J=3.2, 9.3 Hz, 1H, C$_4$H), 4.14 (d, J=3.3 Hz, 1H, C$_3$H), 3.96 (dd, J=3.2, 8.2 Hz, 1H, C$_4$H), 3.69 (d, J=3.2 Hz, 1H, C$_3$H), 3.68 (d, J=3.2 Hz, 1H, C$_3$H), 3.67 (d, J=3.2 Hz, 1H, C$_3$H), 3.67(s, 3H, —COOMe), 3.37 (s, 3H, OMe), 3.35 (s, 3H, OMe), 3.34 (s, 3H, OMe), 3.33 (s, 3H, OMe), 2.97 (dd, J=2.9, 13.0 Hz, 1H, C$_\alpha$H'), 2.77 (dd, J=4.4, 15.5 Hz, 1H, C$_\alpha$H), 2.67 (dd, J=2.8, 14.8 Hz, 1H, C$_\alpha$H'), 2.50 (dd, J=5.2, 15.5 Hz, 1H, C$_\alpha$H'), 2.47 (dd, J=10.5, 14.8 Hz, 1H, C$_\alpha$H), 2.42 (dd, J=4.7, 13.2 Hz, 1H, C$_\alpha$H), 2.18 (dd, J=2.6, 13.2 Hz, 1H, C$_\alpha$H'), 2.04 (dd, J=13.0, 13.0 Hz, 1H, C$_\alpha$H), 1.48 (s, 3H, Me), 1.47 (s, 3H, Me), 1.43 (s, 9H, Boc), 1.43 (s, 3H, Me), 1.43 (s, 3H, Me), 1.38 (s, 3H, Me), 1.30 (s, 3H, Me), 1.29 (s, 3H, Me), 1.28 (s, 3H, Me). FAB MS: 1105.4 (M$^+$+H)

Part 5: Ester Hydrolysis of Tetrapeptide (Scheme 6; 39)

Hydrolysis of ester 38 (1.05 g, 0.95 mmol) with 4N NaOH (4 mL) in methanol (4 mL) was performed according to GP-3 to give 39 (0.93 g, 90%) as a solid, M.p. 144–147° C.; [α]$_D$=+8.3868 (c 0.57, CHCl$_3$), IR (KBr): 3324, 2983, 2929, 1685, 1659, 1531, 1375, 1215, 1164, 1070, 1012 cm$^{-1}$; $^1$H-NMR (500 MHz, CDCl$_3$) δ 8.49 (d, J=9.5 Hz, 1H, R$_3$—NH), 7.85 (d, J=Hz, 1H, S$_2$—NH), 6.35 (d, J=9.3 Hz, 1H S$_4$—NH), 5.91(d, J=3.9 Hz, 1H, C$_1$H), 5.90(d, J=3.9 Hz, 1H, C$_1$H), 5.89 (d, J=3.9 Hz, 1H, C$_1$H), 5.87 (d, J=3.9 Hz, 1H, C$_1$H), 5.34 (d, J=10.3 Hz, 1H, R$_1$—NH), 4.59 (d, J=3.9 Hz, 1H, C$_2$H), 4.55 (d, J=3.9 Hz, 1H, C$_2$H), 4.49 (m, 1H, C$_\beta$H), 4.47 (m, 1H, C$_\beta$H), 4.45(m, 1H, C$_4$H), 4.40 (m, 1H, C$_\beta$H), 4.38 (m, 1H, C$_\beta$H), 4.36 (m, 1H, C$_4$H), 4.21 (m, 1H, C$_4$H), 4.09 (m, 1H, C$_3$H), 3.95 (m, 1H, C$_4$H), 3.94 (d, J=3.1 Hz, 1H, C$_3$H), 3.69 (d, J=3.0 Hz, 1H C$_3$H), 3.65 (d, J=3.1 Hz, 1H, C$_3$H), 3.39 (s, 3H, OMe), 3.36 (s, 3H, OMe), 3.35 (s, 3H, OMe), 3.34 (s, 3H, OMe), 2.88 (m, 1H, C$_\alpha$H'), 2.81 (dd, J=*, 1H, C$_\alpha$H'), 2.70 (dd, J=*, C$_\alpha$H'), 2.42 (dd, J=, C$_\alpha$H), 2.39 (dd, J=, C$_\alpha$H), 2.37 (dd, J=, C$_\alpha$H'), 2.26 (dd, J=, C$_\alpha$H), 2.14 (dd, J=, C$_\alpha$H), 1.50 (s, 3H, Me), 1.49 (s, 3H, Me),1.44 (s, 3H, Me), 1.43 (s, 9H, -Boc), 1.37 (s, 3H, Me), 1.32 (s, 3H, Me), 1.31 (s, 6H, 2-Me), 1.29 (s, 3H, Me). FAB MS: 1091.2 (M$^+$+H)

Part 6: Boc Deprotectin of Tetrapetide (Scheme 6; 40)

Boc deprotection of 39 (0.061 g, 0.055 mmol) with TFA (0.1 mL) in CH$_2$Cl$_2$ (1 mL) according to GP-4 gave 40.

Part 7: Preparation of Hexapeptide (Scheme 6; 41)

Acid 39 (0.3 g, 0.28 mmol) was treated with HOBt (0.045 g, 0.33 mmol), EDCI (0.063 g, 0.33 mmol), 36 (prepared by Boc deprotection of 35 (0.17 g, 0.28 mmol) with TFA (0.2 mL) in CH$_2$Cl$_2$ (2 mL) as described in GP-4) and DIPEA (0.07 mL, 0.4 mmol) according to GP-8 and purified by column chromatography (60–120 mesh Silica gel, 2.5% Methanol-CHCl$_3$) to give 41 (0.265 g, 60%) as a white solid, M.p. 164–167° C.; [α]$_D$=+26.658 (c 0.29, CHCl$_3$), IR (KBr): 3291, 2987.5, 2937, 1734, 1652.5, 1542, 1376, 1217, 1165.5, 1081.5, 1021 cm$^{-1}$; $^1$H-NMR (500 MHz, CDCl$_3$) δ 8.61 (d, J=9.9 Hz, 1H, R$_3$—NH), 8.46 (d, J=9.7 Hz, 1H, R$_5$—NH) 8.23 (d, J=10.0 Hz, 1H, S$_2$—NH), 7.41 (d, J=7.3 Hz, 1H, S$_4$—NH), 6.85 (d, J=8.2 Hz, 1H, S$_6$—NH), 6.20 (d, J=3.7 Hz, 1H, C$_1$H), 6.12 (d, J=3.8 Hz, 1H, C$_1$H), 5.88 (d, J=3.6 Hz, 1H, C$_1$H), 5.87 (d, J=3.9 Hz, 1H, C$_1$H), 5.86 (d, J=4.1 Hz, 1H, C$_1$H), 5.81 (d, J=3.8 Hz, 1H, C$_1$H), 5.47 (d, J=10.6 Hz, 1H, R$_1$—NH), 4.81 (m, 1H, C$_\beta$H), 4.70 (m, 1H, C$_\beta$H), 4.61 (d, J=3.6 Hz, 1H, C$_2$H), 4.57 (d, J=3.7 Hz, 1H, C$_2$H), 4.56 (m, 1H, C$_\beta$OH), 4.56 (d, J=3.8 Hz, 1H, C$_2$H), 4.55 (d, J=4.1 Hz, 1H, C$_2$H), 4.54 (d, J=3.8 Hz, 1H, C$_2$H), 4.53 (m, 1H, C$_\beta$H), 4.47 (d, J=3.9 Hz, 1H, C$_2$H1), 4.42 (m, 1H, C$_\beta$H), 4.38 (dd, J=3.2, 9.4 Hz, 1H, C$_4$H), 4.36 (m, 1H, C$_\beta$H), 4.36 (m, 1H, C$_4$H), 4.34 (dd, J=3.1, 10.2 Hz, 1H, C$_4$H), 4.19(d, J=3.2 Hz, 1H, C$_3$H), 4.17 (dd, J=3.0, 9.7 Hz, 1H, C$_4$H), 4.17 (d, J=3.2 Hz, 1H, C$_3$H), 4.10 (dd, J=3.1, 9.9 Hz, 1H, C$_4$H), 4.06 (dd, J=3.4, 6.0 Hz, 1H, C$_4$H), 3.76 (d, J≈3.0 Hz, 1H, C$_3$H), 3.68 (d, J=3.1 Hz, 1H, C$_3$H), 3.66 (s, 3H, —COOMe), 3.67 (d, J=3.4 Hz, 1H, C$_3$H), 3.62 (d, J=3.1 Hz, 1H, C$_3$H), 3.41 (s, 3H, OMe), 3.38 (s, 3H, OMe), 3.36 (s, 3H, OMe), 3.32 (s, 3H, OMe), 3.32 (s, 3H, OMe), 3.30 (s, 3H, OMe), 3.13 (dd, J=2.1, 12.8 Hz, 1H, C$_\alpha$H'), 2.82 (dd, J=4.6, 15.4 Hz, 1H, C$_\alpha$H), 2.77 (dd, J=2.6, 12.5 Hz, 1H, C$_\alpha$H'), 2.68 (dd, J=2.4, 15.2 Hz, 1H, C$_\alpha$H'), 2.53 (dd, J=11.8, 15.2 Hz, 1H, C$_\alpha$H), 2.52 (dd, J=5.4, 12.8 Hz, 1H, C$_\alpha$H), 2.50 (dd, J=5.5, 15.4 Hz, 1H, C$_\alpha$H'), 2.29 (dd, J=5.0, 12.8 Hz, 1H, C$_\alpha$H), 2.25 (dd, J=3.2, 12.8 Hz, 1H, C$_\alpha$H'), 2.20 (t, J=12.8 Hz, 1H, C$_\alpha$H), 2.11 (t, J=12.5 Hz, 1H, C$_\alpha$H), 2.05 (dd, J=2.7, 12.8 Hz, 1H, C$_\alpha$H'), 1.50 (s, 3H, Me), 1.46 (s, 3H, Me), 1.45 (s, 3H, Me), 1.44 (s, 3H, Me), 1.42 (s, 9H, Boc), 1.36 (s, 3H, Me), 1.33 (s, 3H, Me), 1.31 (s, 3H, Me), 1.28 (s, 3H, Me), 1.28 (s, 3H, Me), 1.28 (s, 3H, Me), 1.27 (s, 3H, Me), 1.26 (s, 3H, Me). FAB MS: 1592.5 (M$^+$+H)

Part 8: Preparation of Octapeptide (Scheme 6; 42)

Acid 39 (0.06 g, 0.055 mmol) was treated with HOBt (0.009 g, 0.07 mmol), EDCI (0.013 g, 0.07 mmol), 40 (prepared by Boc deprotection of 38 (0.061 g, 0.055 mmol) with TFA (0.1 mL) in CH$_2$Cl$_2$ (1 mL) according to GP-4) and DIPEA (0.015 mL, 0.08 mmol) according to GP-9 and purified by column chromatography (60–120 mesh Silica-gel, 3% Methanol-CHCl$_3$) to give 42 (0.051 g, 45%) as a white solid, M.p. 164–167° C.; [α]$_D$=+19.581(c 0.23, CHCl$_3$), IR (KBr): 3283, 2988, 2935, 1648, 1560, 1376, 1214, 1166, 1081, 1022cm$^{-1}$; $^1$H-NMR(500 MHz, CDCl$_3$) δ 8.92 (d, J=10.1 Hz, 1H, R$_5$—NH), 8.60 (d, J=10.1 Hz, 1H, R$_3$—NH), 8.596 (d, J=10.0 Hz, 1H, R$_7$—NH), 8.29 (d, J=9.3 Hz, 1H, S$_4$—NH), 7.94 (d, J=10.2 Hz, 1H, S$_2$—NH), 7.42 (d, J=8.2 Hz, 1H, S$_6$—NH), 6.88(d, J=8.2 Hz, 1H S$_8$—NH), 6.12(d, J=3.7 Hz, 1H, C$_1$H), 6.08 (d, J=3.8 Hz, 1H, C$_1$H), 5.89 (d, J=3.6 Hz, 1H, C$_1$H), 5.89 (d, J=3.6 Hz, 1H, C$_1$H), 5.88 (d, J=3.9 Hz, 1H, C$_1$H), 5.87 (d, J=4.1 Hz, 1H, C$_1$H), 5.87 (d, J=4.1 Hz, 1H, C$_1$H), 5.82 (d, J=3.8 Hz, 1H, C$_1$H), 5.35 (d, J=8.5 Hz, 1H, R$_1$—NH), 4.77 (m, 1H, C$_\beta$H), 4.75 (m, 1H, C$_\beta$H), 4.66 (m, 1H, C$_\beta$H), 4.58 (d, J=3.8 Hz, 1H, C$_2$H), 4.57 (d, J=3.7 Hz, 1H, C$_2$H), 4.57 (d, J=3.7 Hz, 1H, C$_2$H), 4.56 (d, J=3.9 Hz, 1H, C$_2$H), 4.55 (d, J=3.8 Hz, 1H, C$_2$H), 4.55 (d, J=3.8 Hz, 1H, C$_2$H), 4.51 (m, 1H, C$_\beta$H), 4.51 (d, J=3.8 Hz, 1H, C$_2$H), 4.50 (m, 1H, C$_\beta$H), 4.44 (m, 1H, C$_\beta$H), 4.43 (d, J=3.8 Hz, 1H, C$_2$H), 4.42 (dd, J=3.2, 9.4 Hz, 1H, C$_4$H), 4.38(m, 1H, C$_\beta$H), 4.36 (m, 1H, C$_\beta$H), 4.33 (dd, J=3.1, 9.4 Hz, 1H, C$_4$H), 4.30 (dd, J=3.2, 9.7 Hz, 1H, C$_4$H), 4.22 (m, 1H, C$_4$H), 4.16 (dd, J=3.2, 9.6 Hz, 1H, C$_4$H), 4.16 (dd, J=3.1, 9.7 Hz, 1H, C$_4$H), 4.15(d, J=3.2 Hz, 1H, C$_3$H), 4.12 (d, J=3.2 Hz, 1H, C$_3$H), 4.10 (dd, J=3.1, 10.0 Hz, 1H, C$_4$H), 4.04 (dd, J=3.2, 6.7 Hz, 1H, C$_4$H), 3.73 (d, J=3.0 Hz, 1H, C$_3$H), 3.73 (d, J=3.0 Hz, 1H, C$_3$H), 3.67 (s, 3H, —COOMe), 3.66 (d, J=3.2 Hz, 1H, C$_3$H), 3.65 (d, J=3.1 Hz, 1H, C$_3$H), 3.61 (d, J=3.1 Hz, 1H, C$_3$H), 3.39 (s, 3H, OMe), 3.38 (s, 3H, OMe), 3.37 (s, 3H, OMe), 3.36 (s, 3H, OMe), 3.35 (s, 3H, OMe), 3.34(s, 3H, OMe), 3.33 (s, 3H, OMe), 3.25 (s, 3H, OMe), 2.97 (dd, J=1.5, 12.8 Hz, 1H, C$_\alpha$H'), 2.89 (dd, J=2.2, 12.8 Hz, 1H, C$_\alpha$H), 2.88 (dd, J=2.2, 12.2 Hz, 1H, C$_\alpha$H), 2.81(m,1H, C$_\alpha$H'), 2.67 (dd, J=1.9, 12.1 Hz, 1H, C$_\alpha$H'), 2.56 (dd, J=11.8, 15.2 Hz, 1H, C$_\alpha$H), 2.55 (dd, J=5.4, 12.8 Hz, 1H, C$_\alpha$H), 2.48 (dd, J=5.5, 15.4 Hz, 1H, C$_\alpha$H'), 2.42 (dd, J=5.5, 154 Hz, 1H, C$_\alpha$H), 2.36 (dd, J=5.0, 12.8 Hz, 1H, C$_\alpha$H), 2.32 (dd, J=3.2, 12.8 Hz, 1H, C$_\alpha$H'), 2.28 (t, J=12.8 Hz, 1H, C$_\alpha$H), 2.26 (t, J=12.5 Hz, 1H, C$_\alpha$H), 2.16 (dd, J=2.7, 15.4 Hz, 1H, C$_\alpha$H'), 2.09 (dd, J=2.7, 12.8 Hz, 1H, C$_\alpha$H'), 2.05 (dd, J=2.7, 12.8 Hz, 1H, C$_\alpha$H), 1.50 (s, 3H, Me), 1.46 (s, 3H, Me), 1.45 (s, 3H, Me), 1.44 (s, 3H, Me), 1.42 (s, 9H, Boc), 1.36 (s, 3H, Me), 1.33 (s, 3H, Me), 1.31 (s, 3H, Me), 1.28 (s, 3H, Me), 1.28 (s, 3H, Me), 1.28 (s, 3H, Me), 1.27 (s, 3H, Me), 1.26 (s, 3H, Me). FAB MS: 2078.4 (M$^+$+H)

Part 9: Preparation of Tripeptide (Scheme 6; 43)

Acid 37 (0.15 g, 0.25 mmol) was treated with HOBt (0.04 g, 0.3 mmol), EDCI (0.06 g, 0.3 mmol), 10 (prepared by Boc deprotection of 8a (0.094 g, 0.25 mmol) with TFA (0.1 mL) in CH$_2$Cl$_2$ (1.0 mL) according to GP-4) and DIPEA (0.06 mL, 0.37 mmol) according to GP-6 and purified by column chromatography (60–120 mesh Silica-gel, 70% EtOAc-pet. ether) to give 43 (0.16 g, 75.1%) as a white solid, M.p. 108–111° C.; [α]$_D$=−5.103 (c 0.45, CHCl$_3$), IR (KBr): 3364, 3308, 2996, 2940, 1717, 1670, 1542, 1371, 1164, 1077, 1010 cm$^{-1}$; $^1$H-NMR (500 MHz, CDCl$_3$) δ 8.08 (d, J=9.5 Hz, 1H, R$_3$—NH), 7.19 (d, J=9.6 Hz, 1H, S$_2$—NH), 5.89 (d, J=3.8 Hz, 1H, C$_1$H), 5.89 (d, J=3.8 Hz, 1H, C$_1$H), 5.85 (d, J=3.8 Hz, 1H, C$_1$H), 5.26 (d, J=10.5 Hz, 1H, R$_1$—NH), 4.69 (m, 1H, C$_\beta$H), 4.57 (d, J=3.8 Hz, 1H, C$_2$H), 4.53 (d, J=3.8 Hz, 1H, C$_2$H), 4.53 (m, 1H, C$_\beta$H), 4.52 (d, J=3.8 Hz, 1H, C$_2$H), 4.50 (m,1H, C$_\beta$H), 4.30 (dd, J=7.6, 3.2 Hz, 1H, C$_4$H), 4.17 (dd, J=7.5, 3.2 Hz, 1H, C$_4$H), 4.13 (d, J=3.1 Hz, 1H, C$_3$H), 3.99 (dd, J=6.8, 3.2 Hz, 1H, C$_4$H), 3.71 (d, J=3.3 Hz, 1H, C$_3$H), 3.70 (d, J=3.2 Hz, 1H, C$_3$H), 3.66 (s, 3H, COOMe), 3.39(s, 3H, OMe), 3.38 (s, 3H, OMe), 3.36(s,3H, OMe), 2.78 (dd, J=2.7, 12.4 Hz, 1H, C$_\alpha$H'), 2.53 (m, 2H, C$_\alpha$H,H'), 2.34 (dd, J=4.9, 13.1 Hz, 1H, C$_\alpha$H), 2.22 (dd, J=3.3, 13.1, 1H, C$_\alpha$H'), 2.16 (dd, J=12.4, 12.9 Hz, 1H, C$_\alpha$H'), 1.44 (s, 6H, 2×Me), 1.43 (s, 9H, -Boc), 1.39 (s, 3H, Me), 1.306 (s, 3H, Me), 1.298 (s, 3H, Me), 1.29 (s, 3H, Me).

EXAMPLE-6

Part 1: Preparation of Tetrapeptide (Scheme 7; 44)

Acid 22 (0.1 g, 0.165 mmol) was treated with HOBt (0.027 g, 0.2 mmol), EDCI (0.038 g, 0.2 mmol), 36 (prepared by Boc deprotection of 35 (0.105 g, 0.165 mmol) with TFA (0.1 mL) in CH$_2$Cl$_2$ (1 mL) according to GP-4) and DIPEA (0.065 mL, 0.25 mmol) according to GP-7 and purified by column chromatography (60–120 mesh Silica-gel, 2% Methanol-CHCl$_3$) to give 44 (0.135 g, 73.9%) as a white solid, M.p. 112–115° C.; [α]$_D$=−43.619 (c 0.36, CHCl$_3$), IR (KBr): 3388, 2988, 2941, 1718, 1675, 1521, 1368, 1164, 1070, 1021 cm$^{-1}$; $^1$H-NMR (500 MHz, CDCl$_3$) δ 7.24 (d, J=9.3 Hz, 1H, R2-NH), 7.07 (d, J=9.3 Hz, 1H, R3-NH), 6.95 (d, J=8.4 Hz, 1H, S4-NH), 5.88 (d, J=3.9 Hz, 1H, C$_1$H), 5.88 (d, J=4.0 Hz, 1H, C$_1$H), 5.90 (d, J=3.9 Hz, 1H, C$_1$H), 5.87 (d, J=3.9 Hz, 1H, C$_1$H), 5.54 (d, J=9.7 Hz, 1H, S1-NH), 4.64 (m, 1H, C$_\beta$H), 4.57 (d, J=3.9 Hz, 1H, C$_2$H), 4.55 (m, 1H, C$_\beta$H), 4.55 (d, J=3.9 Hz, 1H, C$_2$H), 4.53 (d, J=4.0 Hz, 1H, C$_2$H), 4.53 (d, J=3.9 Hz, 1H, C$_2$H), 4.49 (m, 1H, C$_\beta$H), 4.42 (dd, J=3.2, 8.1 Hz, 1H, C$_4$H), 4.31 (dd, J=3.3, 7.6 Hz, 1H, C$_4$H), 4.30 (dd, J=3.2, 7.8 Hz, 1H, C$_4$H), 4.24 (m, 1H, C$_\beta$H), 4.21 (dd, J=3.2, 7.9 Hz, 1H, C$_4$H), 3.74 (d, J=3.3 Hz, 1H, C$_3$H), 3.67 (d, J=3.0 Hz, 1H, C$_3$H), 3.68 (s, 3H, —COOMe), 3.67 (d, J=3.2 Hz, 1H, C$_3$H), 3.64 (d, J=3.2 Hz, 1H, C$_3$H), 3.39 (s, 3H, OMe), 3.38 (s, 3H, OMe), 3.37 (s, 3H, OMe), 3.36 (s, 3H, OMe), 2.66 (d, J=6.0 Hz, 2H, C$_\alpha$H,H'), 2.57 (dd, J=5.4, 14.5 Hz, 1H, C$_\alpha$H), 2.55 (m, 1H, C$_\alpha$H), 2.53 (m, 1H, C$_\alpha$H), 2.47 (m, 1H, C$_\alpha$H), 2.44 (dd, J=4.2, 14.5 Hz, 1H, C$_\alpha$H), 2.44 (m, 1H, C$_\alpha$H'), 1.47 (s, 3H, Me), 1.45 (s, 3H, Me), 1.446 (s, 6H, 2-Me), 1.446 (s, 3H, Me), 1.42 (s, 9H, Boc), 1.31 (s, 3H, Me), 1.30 (s, 3H, Me), 1.29 (s, 3H, Me). FAB MS: 1105.2 (M$^+$+H)

Part 2: Preparation of Tetrapeptide (Scheme 7; 45)

Acid 37 (0.07 g, 0.116 mmol) was treated with HOBt (0.02 g, 0.14 mmol), EDCI (0.027 g, 0.14 mmol), 21 (prepared by Boc deprotection of 20 (0.072 g, 0.125 mmol) with TFA (0.1 mL) in CH$_2$Cl$_2$ (1 mL) according to GP-4) and DIPEA (0.03 mL, 0.17 mmol) according to GP-7 and purified by column chromatography (60–120 mesh Silica-gel, 2% Methanol-CHCl$_3$) to give 45 (0.102 g, 79.7%) as a white solid, M.p. 118–121° C.; [α]$_D$=−26.569 (c 0.5, CHCl3), IR (KBr): 3387, 2987, 2940, 1724, 1662, 1538, 1377, 1158, 1080, 1013 cm$^{-1}$; $^1$H-NMR (500 MHz, CDCl$_3$) δ 7.29 (d, J=9.0 Hz, 1H, S3-NH), 7.05 (d, J=9.1 Hz, 1H, R4-NH), 6.84 (d, J=8.9 Hz, 1H, S2-NH), 5.90 (d, J=4.0 Hz, 1H, C$_1$H), 5.88 (d, J=3.9 Hz, 1H, C$_1$H), 5.88 (d, J=3.9 Hz, 1H, C$_1$H), 5.87 (d, J=3.9 Hz, 1H, C$_1$H), 5.63 (d, J=9.8 Hz, 1H, R1-NH), 4.65 (m, 1H, C$_\beta$H), 4.57 (d, J=3.9 Hz, 1H, C$_2$H), 4.55 (d, J=3.9 Hz, 1H, C$_2$H), 4.53 (d, J=4.0 Hz, 1H, C$_2$H), 4.53 (d, J=3.9 Hz, 1H, C$_2$H), 4.52 (m, 1H, C$_\beta$H), 4.48 (m, 1H, C$_\beta$H), 4.36 (m, 1H, C$_\beta$H), 4.34 (dd, J=3.3, 7.7 Hz, 1H, C$_4$H), 4.28 (dd, J=3.2, 7.3 Hz, 1H, C$_4$H), 4.22 (dd, J=3.2, 8.7 Hz, 1H, C$_4$H), 4.18 (dd, J=3.2, 7.6 Hz, 1H, C$_4$H), 3.95 (d, J=2.9 Hz, 1H, C$_3$H), 3.76 (d, J=3.1 Hz, 1H, C$_3$H), 3.74 (d, J=3.0 Hz, 1H, C$_3$H), 3.72 (d, J=2.8 Hz, 1H, C$_3$H), 3.68 (s, 3H, —COOMe), 3.39 (s, 3H, OMe), 3.38 (s, 3H, OMe), 3.37 (s, 3H, OMe), 3.36 (s, 3H, OMe), 2.69 (dd, J=4.8, 15.5 Hz, 1H, C$_\alpha$H'), 2.63 (dd, J=7.0, 15.5 Hz, 1H, C$_\alpha$H), 2.56 (dd, J=4.2, 14.6 Hz, 1H, C$_\alpha$H'), 2.48 (dd, J=6.5, 15 Hz, 1H, C$_\alpha$H'), 2.46 (m,1H, C$_\alpha$H), 2.40 (dd, J=4.8, 15.0 Hz, 1H, C$_\alpha$H), 2.43 (m, 1H, C$_\alpha$H'), 2.43 (m, 1H, C$_\alpha$H), 1.47 (s, 3H, Me), 1.45 (s, 3H, Me), 1.42 (s, 9H, Boc), 1.46 (s, 3H, Me), 1.46 (s, 3H, Me), 1.31 (s, 3H, Me), 1.30 (s, 3H, Me), 1.29 (s, 3H, Me), 1.29 (s, 3H, Me). FAB MS: 1105.1 (M$^+$+H)

EXAMPLE-7

Part 1: Preparation of Dipeptide (Scheme 8; 47)

Acid 6 (0.45 g, 1.25 mmol) was treated with HOBt (0.202 g, 1.5 mmol), EDCI (0.287 g, 1.5 mmol) and 46 (prepared by neutralization of β-alanine methyl ester salt (0.174 g, 4.57 mmol) with DIPEA (0.32 mL, 1.87 mmol), according to GP-5 and purified by column chromatography (60–120 mesh Silica-gel, 60% EtOAc-pet ether) to give 47 (0.475 g, 85.6%) as a white solid, M.p. 140–142° C.; [α]$_D$=−38.236 (c 0.5, CHCl3), IR (KBr): 3355, 2981, 1744.5, 1693, 1651, 1528, 1370, 1250, 1172, 1076, 1022 cm$^{-1}$; $^1$H-NMR (500 MHz, CDCl$_3$) δ 6.59 (bs, 1H, Ala-NH), 5.90 (d, J=3.9 Hz, 1H, C$_1$H), 5.13 (bs, 1H, S1-NH), 4.58 (d, J=3.9 Hz, 1H, C$_2$H), 4.27 (dd, J=7.7, 3.2, 1H, C$_4$H), 4.14 (m, 1H, C$_\beta$H), 3.73 (d, J=3.2, 1H, C$_3$H), 3.70 (s, 3H, COOMe), 3.51 (q, J=6.1 Hz, 2H, C$_\beta$H), 3.37(s, 3H, OMe), 2.54 (t, J=6.1 Hz, 2H, C$_\alpha$H,H'), 2.52 (dd, J=5.9, 14.8, 1H, C$_\alpha$H), 2.46 (dd, J=6.0, 14.8, C$_\alpha$H'), 1.48 (s,3H, Me), 1.43 (s,9H, -Boc), 1.32 (s, 3H, Me). FAB MS: 447.2 (M$^+$+H)

Part 2: Boc Deprotectin of Dipetide (Scheme 8; 48)

Boc deprotection of 47 (0.134 g, 0.30 mmol) with TFA (0.15 mL) in CH$_2$Cl$_2$ (1.5 mL) was performed according to GP-4 to give the amine salt 48.

Part 3: Ester Hydrolysis of Dipeptide (Scheme 8; 49)

Hydrolysis of ester 47 (0.225 g, 0.505 mmol) with 4N NaOH (2 mL) in methanol (2 mL) was performed according to GP-3 to give 49 (0.19 g, 88.1%) as a solid, M.p 147–149° C.; $[\alpha]_D$=–41.7555 (c 0.6, CHCl$_3$), IR (KBr): 3354, 2981, 1692, 1648, 1528, 1370, 1251, 1168, 1076, 1021 cm$^{-1}$; $^1$H-NMR (500 MHz, CDCl$_3$) δ 7.11 (bs, 1H, Ala-NH), 5.90 (d, J=3.9 Hz, 1H, C$_1$H), 5.23 (bs, 1H, S1-NH), 4.58 (d, J=3.9 Hz, 1H, C$_2$H), 4.33 (m, 1H, C$_4$H), 4.15 (m, 1H, C$_\beta$H), 3.73 (d, J=3.2, 1H, C$_3$H), 3.52 (m, 2H, C$_\beta$H), 3.37(s, 3H, OMe), 2.57 (t, J=6.1 Hz, 2H, C$_\alpha$H,H'), 2.49 (m, 2H, C$_\alpha$H,H'), 1.48 (s, 3H, Me), 1.43 (s, 9H, -Boc), 1.32 (s, 3H, Me). FAB MS: 433.2 (M$^+$+H)

Part 4: Preparation of Tetrapeptide (Scheme 8; 50)

Acid 49 (0.13 g, 0.3 mmol) was treated with HOBt (0.05 g, 0.36 mmol), EDCI (0.05 g, 0.36 mmol), 48 (prepared by Boc deprotection of 47 (0.134 g, 0.3 mmol) with TFA (0.15 mL) in CH$_2$Cl$_2$ (1.5 mL) according to GP-4) and DIPEA (0.08 mL, 0.45 mmol) according to GP-7 and purified by column chromatography (60–120 mesh Silica-gel, 3% Methanol-CHCl$_3$) to give 50 (0.18 g, 78.7%) as a white solid, M.p. 184–186° C.; $[\alpha]_D$=–64.635 (c 0.6, CHCl$_3$), IR (KBr): 3336, 2984, 2937, 1740, 1690, 1654, 1542, 1372, 1254, 1168, 1079, 1020 cm$^{-1}$; FAB MS: 761.3 (M$^+$+H)

Part 5: Ester Hydrolysis of Tetrapeptide (Scheme 8; 51)

Hydrolysis of ester 50 (0.5 g, 0.66 mmol) with 4N NaOH (2.5 mL) in methanol (2.5 mL) was performed according to GP-3 to give 51 (0.43 g, 87.6%) as a solid, M.p. 165–168° C.; IR (KBr): 3317, 2988, 2941, 1717, 1647, 1537, 1364, 1247, 1160, 1074, 1011 cm$^{-1}$;

Part 6: Preparation of Hexapeptide (Scheme 8; 52)

Acid 51 (0.2 g, 0.27 mmol) was treated with HOBt (0.04 g, 0.32 mmol), EDCI (0.06 g, 0.32 mmol), 48 (prepared by Boc deprotection of 47 (0.12 g, 0.27 mmol) with TFA (0.1 mL) in CH$_2$Cl$_2$ (1 mL) as described in GP-4) and DIPEA (0.07 mL, 0.4 mmol) according to GP-8 and purified by column chromatography (60–120 mesh Silica gel, 4% Methanol-CHCl$_3$) to give 52 (0.155 g, 53.8%) as a white solid, M.p. 220–223° C.; IR (KBr): 3301, 2978, 2932, 1656, 1547, 1368, 1173, 1081, 1025 cm$^{-1}$.

REFERENCES

Gellman et al, *J. Am. Chem. Soc.*, 116, 1054–1062 (1994)

Seabach et al, *Helv. Chim. Acta*, 79, 913–941 and 2043–2066 (1996)

Gellman et al, *J. Am. Chem. Soc.*, 118, 13071–72 (1996)

Gellman et al, *Nature*, 387, 381 (1997)

Gellman et al, U.S. Pat. No. 6,060,585

Seebach et al, *Helv. Chim. Acta*, 81, 932 (1998)

Seebach et al, *Helv. Chim. Acta*, 81, 2218–2243 (1998)

Schweizer, *Angew. Chem. Int. E.*, 41, 230–253 (2002)

Kessler et al, *Chem. Rev.*, 102, 491–514 (2002)

Kessler et al, *Chem. Eur. J.*, 8, 4366–4376 (2002)

Sharma et al, *Tetrahedron: Asymm.*, 13, 21–24, (2002)

Dhawale et al, *J. Org. Chem.*, 16, 1065, 2001

Bodanszky et al, *The practice of Peptide Synthesis*, Springer Verlag, New York, 1984

Cavanagh et al, *Protein NMR Spectroscopy*, Academic Press, San Diego, 1996

Wuthrich et al, *NMR of Proteins and Nucleic Acids*, Wiley, New York, 1986

States et al, *J. Magn. Reson.* 48, 286–292, 1982

What is claimed is:

1. A C-linked β-peptide compound of the general formula I

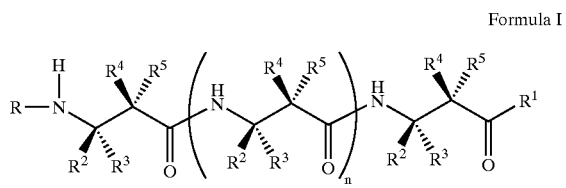

Formula I wherein n=0, 1, 2, 3 . . .

R=H, Box, Cbz, Fmoc, acetyl or a salt formed with HCl or TFA;

R$^1$=—O alkyl, —O-aralkyl, -amine, alkylamine, or aryalkyl amine;

R$^2$=R$^3$=R$^4$=R$^5$=H; or

R$^2$=sugar or hydroxy alkyl, amino alkyl, or amino thioalkyl, and R$^3$=R$^4$=R$^5$=H; or R$^3$=sugar or hydroxy alkyl, amino alkyl, or amino thioalkyl, and R$^2$=R$^4$=R$^5$=H; or R$^4$=sugar or hydroxy alkyl, amino alkyl, or amino thioalkyl, and R$^2$=R$^3$=R$^5$=H; or R$^5$=sugar or hydroxy alkyl, amino alkyl, or amino thioalkyl, and R$^2$=R$^3$=R$^4$=H; or R$^2$=R$^4$=sugar or hydroxy alkyl, amino alkyl, or amino thioalkyl, and R$^3$=R$^5$=H; or R$^3$=R$^5$=sugar or hydroxy alkyl, amino alkyl, or amino thioalkyl, and R$^2$=R$^4$=H; or R$^2$=R$^5$=sugar or hydroxy alkyl, amino alkyl, or amino thioalkyl, and R$^3$=R$^4$=H; or R$^3$=R$^4$=sugar or hydroxy alkyl, amino alkyl, or amino thioalkyl, and R$^2$=R$^5$=H; or R$^2$=R$^3$=sugar or hydroxy alkyl, amino alkyl, or amino thioalkyl, and R$^4$=R$^5$=H; or R$^4$=R$^5$=sugar or hydroxy alkyl, amino alkyl, or amino thioalkyl, and R$^2$=R$^3$=H.

2. A compound as claimed in claim 1, wherein the sugar is selected from the group consisting of a monosaccharide pentose, an L-sugar in furanoside or pyranoside form, a hexose, and a disaccharide.

3. A compound as claimed in claim 2, wherein the monosaccharide pentose is selected from the group consisting of D-xylo, D-ribo, D-lyxo and D-ara; the L-sugar is selected from the group consisting of L-xyl, L-rib, L-lyxo and L-ara, the hexose is selected from the group consisting of D and L-glc, D and L-gal, D and L-man D and L-gul, and D and L-all; and disaccharide is selected from the group consisting of lactose, maltose and cellobiose.

4. A compound as claimed in claim 1, wherein the sugar is a fully protected sugar and comprises an acetate, a benzoate, an allyl ether, an aralkyl ether, an alkylidene dioxolane derivative or a thio derivative.

5. A compound as claimed in claim 1, wherein the sugar is an unprotected sugar.

6. A compound as claimed in claim 1, wherein the sugar is a D- or L-sugar in furanoside or pyranoside form comprising a heterocyclic base selected from the group consisting of adenine, guanine, thymidine, and cytosine.

7. A compound as claimed in claim 1, wherein the sugar comprises a heterocyclic 5 or 6 member ring comprising at least one of oxygen, nitrogen and sulfur.

8. A compound as claimed in claim 1, wherein the sugar is selected from the group consisting of a deoxy sugar, an amino sugar, a natural sugar, a non-natural sugar, a rare sugar, a higher sugar and a bifunctional sugar amino acid.

9. A C-linked β-peptide compound as claimed in claim 1, wherein the compound has a structural formula shown below:

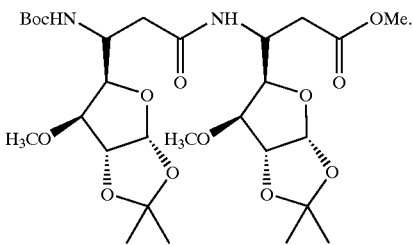

10. A C-linked β-peptide compound as claimed in claim 1, wherein the compound has a structural formula shown below:

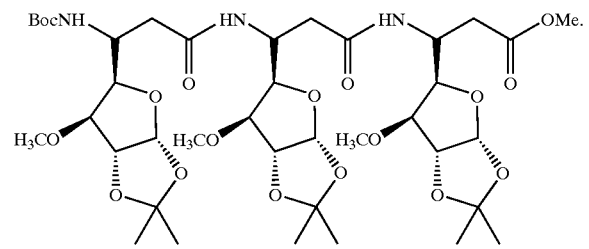

11. A C-linked β-peptide compound as claimed in claim 1, wherein the compound has a structural formula shown below:

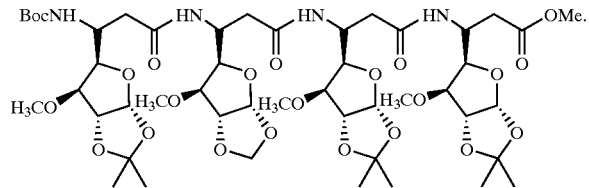

12. A C-linked β-peptide compound as claimed in claim 1, wherein the compound has a structural formula shown below:

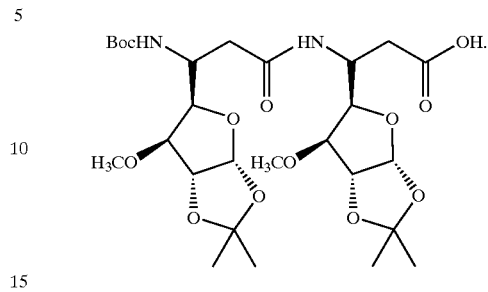

13. A C-linked β-peptide compound as claimed in claim 1, wherein the compound has a structural formula shown below:

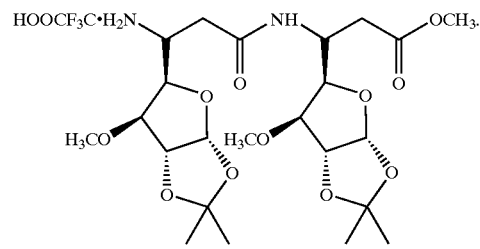

14. A C-linked β-peptide compound as claimed in claim 1, wherein the compound has a structural formula shown below:

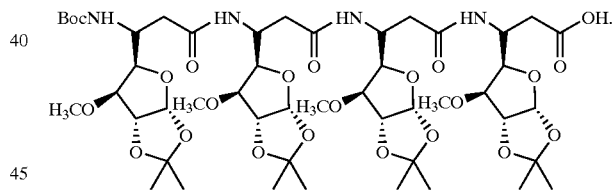

15. A C-linked β-peptide compound as claimed in claim 1, wherein the compound has a structural formula shown below:

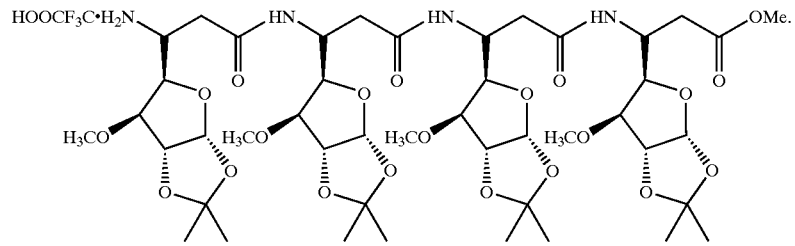

16. A C-linked β-peptide compound as claimed in claim 1, wherein the compound has a structural formula shown below:

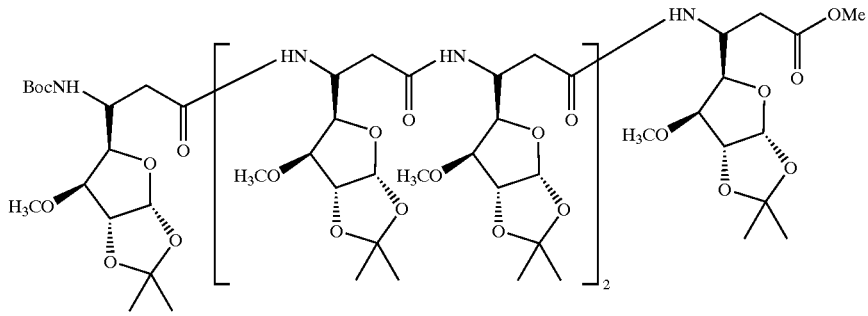

17. A C-linked β-peptide compound as claimed in claim 1, wherein the compound has a structural formula shown below:

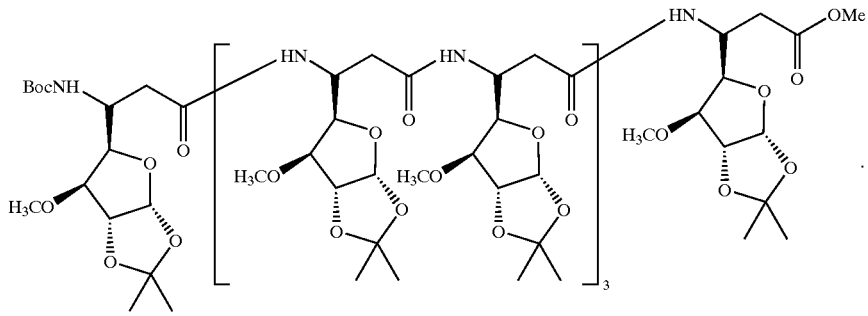

18. A C-linked β-peptide compound as claimed in claim 1, wherein the compound has a structural formula shown below:

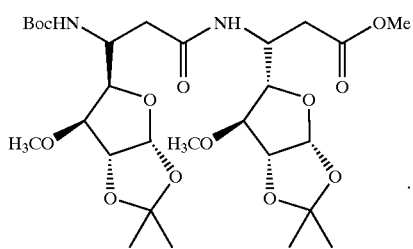

19. A C-linked β-peptide compound as claimed in claim 1, wherein the compound has a structural formula shown below:

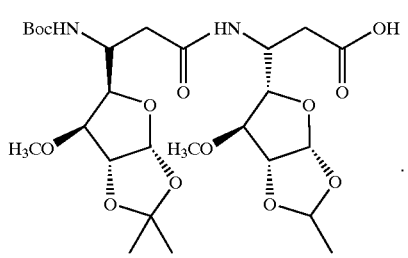

20. A C-linked β-peptide compound as claimed in claim 1, wherein the compound has a structural formula shown below:

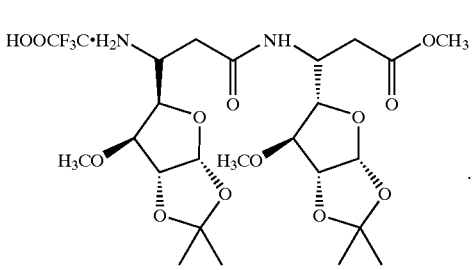

21. A C-linked β-peptide compound as claimed in claim 1, wherein the compound has a structural formula shown below:

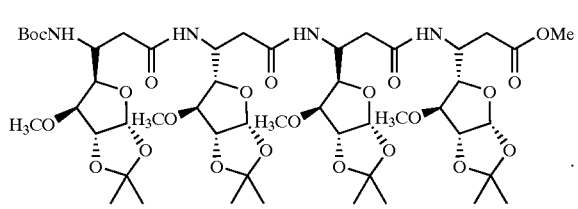

22. A C-linked β-peptide compound as claimed in claim 1, wherein the compound has a structural formula shown below:

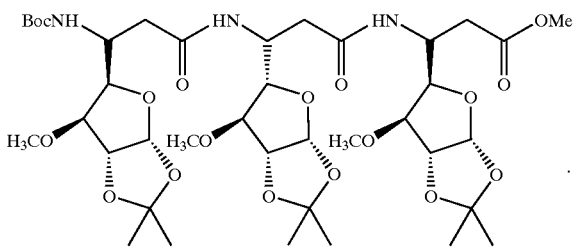

23. A C-linked β-peptide compound as claimed in claim 1, wherein the compound has a structural formula shown below:

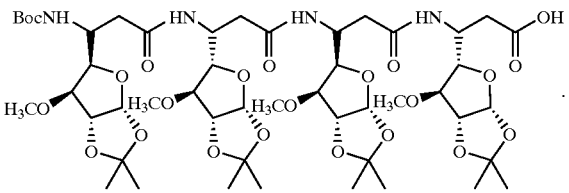

24. A C-linked β-peptide compound as claimed in claim 1, wherein the compound has a structural formula shown below:

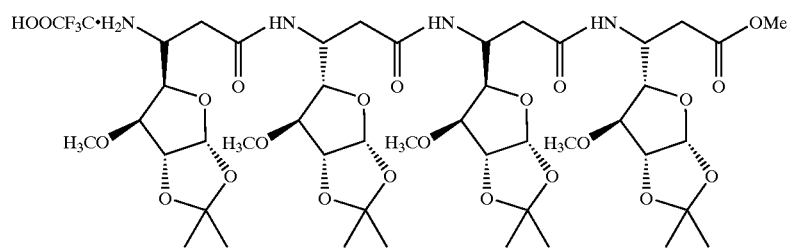

25. A C-linked β-peptide compound as claimed in claim 1, wherein the compound has a structural formula shown below:

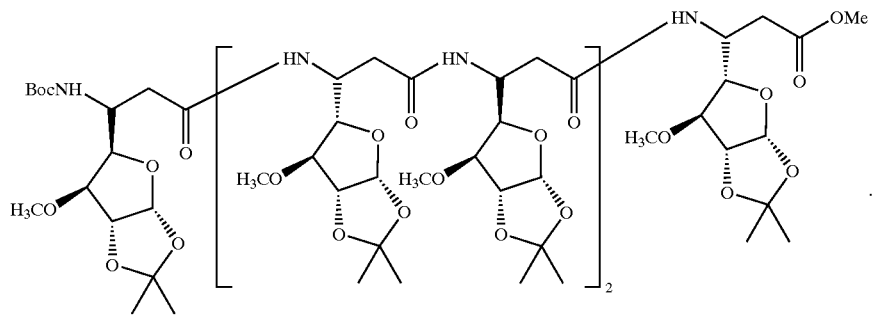

26. A C-linked β-peptide compound as claimed in claim 1, wherein the compound has a structural formula shown below:

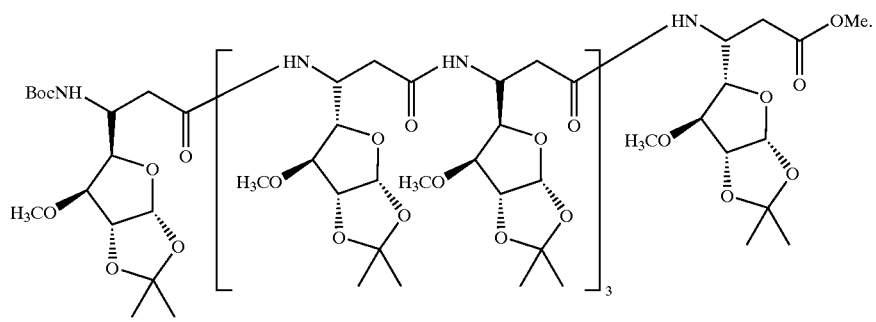

27. A C-linked β-peptide compound as claimed in claim 1, wherein the compound has a structural formula shown below:

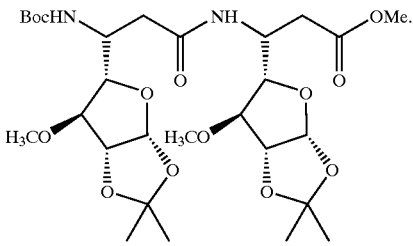

28. A C-linked β-peptide compound as claimed in claim 1, wherein the compound has a structural formula shown below:

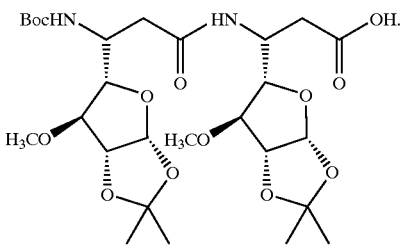

29. A C-linked β-peptide compound as claimed in claim 1, wherein the compound has a structural formula shown below:

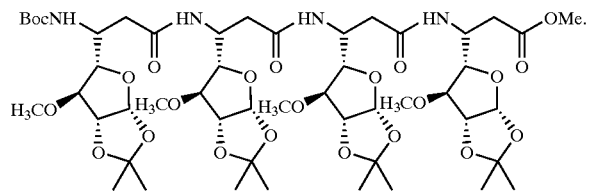

30. A C-linked β-peptide compound as claimed in claim 1, wherein the compound has a structural formula shown below:

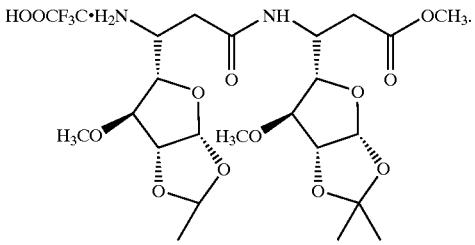

31. A C-linked β-peptide compound as claimed in claim 1, wherein the compound has a structural formula shown below:

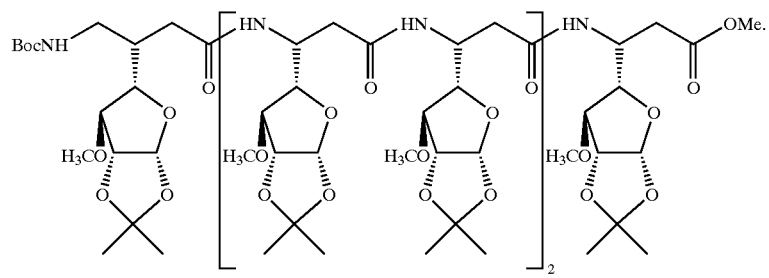

32. A C-linked β-peptide compound as claimed in claim 1, wherein the compound has a structural formula shown below:

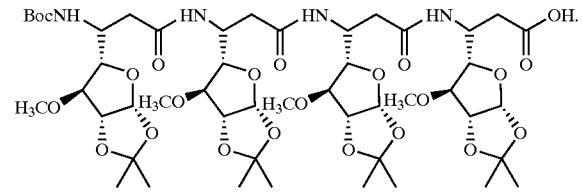

33. A C-linked β-peptide compound as claimed in claim 1, wherein the compound has a structural formula shown below:

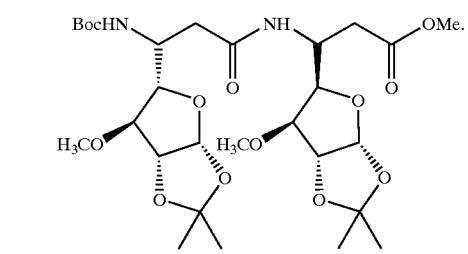

34. A C-linked β-peptide compound as claimed in claim 1, wherein the compound has a structural formula shown below:

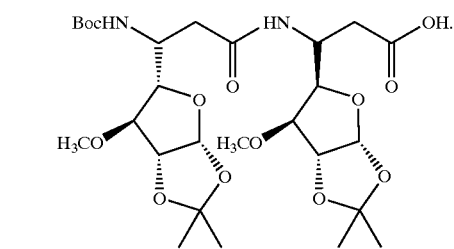

35. A C-linked β-peptide compound as claimed in claim 1, wherein the compound has a structural formula shown below:

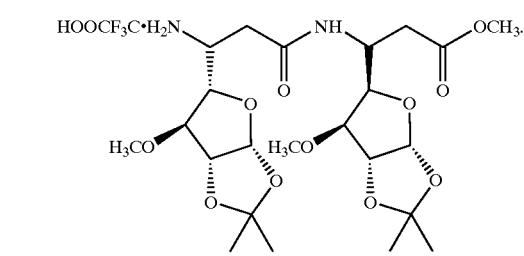

36. A C-linked β-peptide compound as claimed in claim 1, wherein the compound has a structural formula shown below:

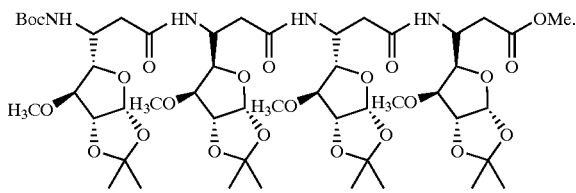

37. A C-linked β-peptide compound as claimed in claim 1, wherein the compound has a structural formula shown below:

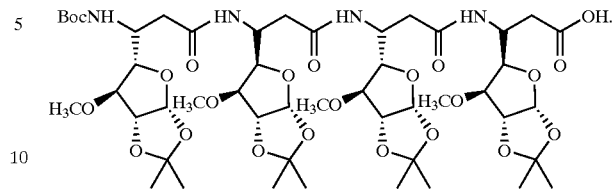

38. A C-linked β-peptide compound as claimed in claim 1, wherein the compound has a structural formula shown below:

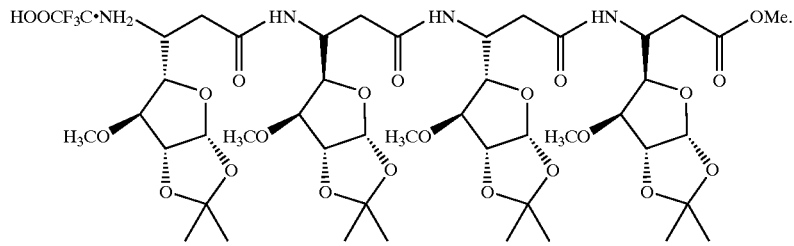

39. A C-linked β-peptide compound as claimed in claim 1, wherein the compound has a structural formula shown below:

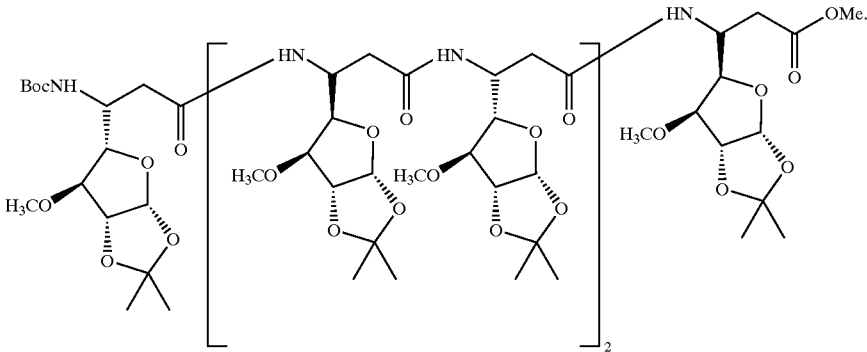

40. A C-linked β-peptide compound as claimed in claim 1, wherein the compound has a structural formula shown below:

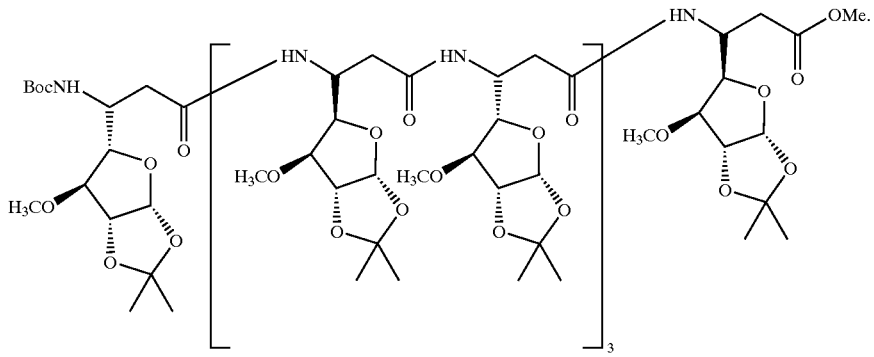

41. A C-linked β-peptide compound as claimed in claim 1, wherein the compound has a structural formula shown below:

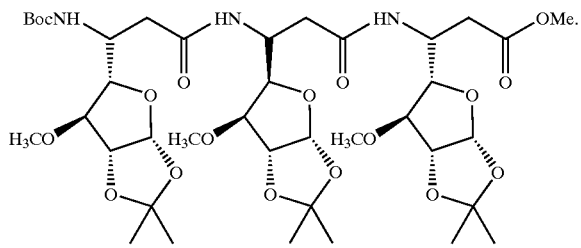

42. A C-linked β-peptide compound as claimed in claim 1, wherein the compound has a structural formula shown below:

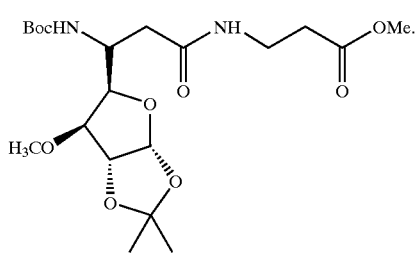

43. A C-linked β-peptide compound as claimed in claim 1, wherein the compound has a structural formula shown below: B

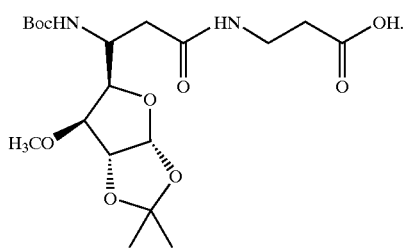

44. A C-linked β-peptide compound as claimed in claim 1, wherein the compound has a structural formula shown below:

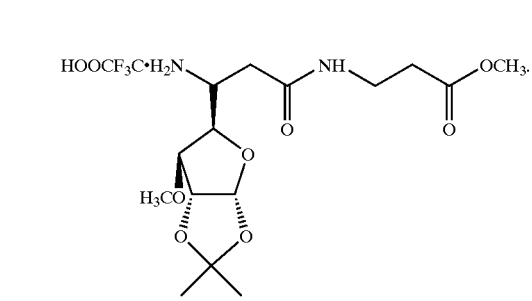

45. A C-linked β-peptide compound as claimed in claim 1, wherein the compound has a structural formula shown below:

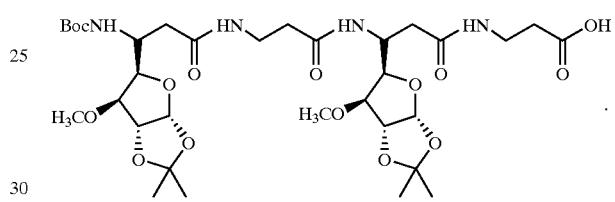

46. A C-linked β-peptide compound as claimed in claim 1, wherein the compound has a structural formula shown below:

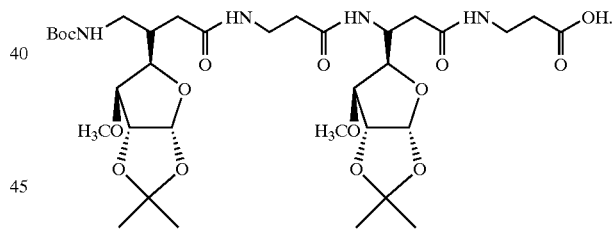

47. A C-linked β-peptide compound as claimed in claim 1, wherein the compound has a structural formula shown below:

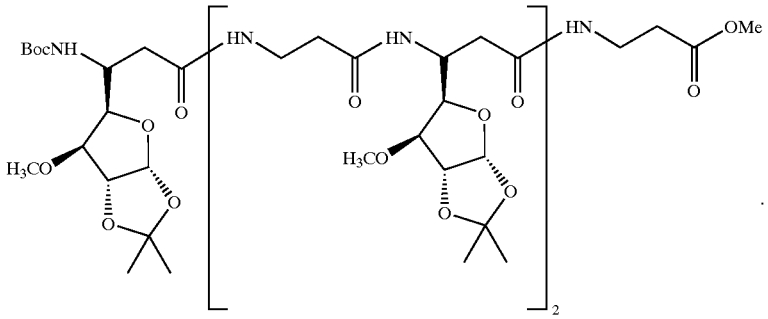

48. A method for preparation of the C-linked β-peptide compound of claim 1, comprising:
   a) reacting a C-linked carbo β-amino acid ester with Pd—C and exposing it to (Boc)$_2$ to give N-Boc C-linked β-amino acid ester;
   b) subjecting a first portion of the N-Boc C-linked carbo β-amino acid ester obtained in step (a) to an aqueous alkaline hydrolysis to give a C-linked carbo β-amino acid;
   c) subjecting a second portion of the N-Boc C-linked carbo β-amino acid ester obtained in step (a) to an acid mediated hydrolysis to give a salt of C-linked β-amino acid ester; and
   d) reacting the C-linked carbo β-amino acid obtained in step (b) with the salt of a C-linked carbo β-amino acid ester obtained in step (c) under peptide formation conditions to give a dipeptide.

49. The method according to claim 48, further comprising the step of e) subjecting the dipeptide obtained in step (d) to an alkaline treatment to give a dipeptide acid.

50. The method according to claim 49, further comprising the steps of (f) subjecting the dipeptide obtained in step (d) to an acid treatment with yield of a dipeptide salt and (g) reacting the dipeptide salt with the dipeptide acid to yield a tetrapeptide.

51. The method according to claim 49, further comprising reacting the dipeptide acid with a β-amino acid monomer amine salt that yields a tripeptide.

52. The method according to claim 50, further comprising subjecting the tetrapeptide to an alkaline treatment to yield tetrapeptide acid and reacting the tetrapeptide acid with the dipeptide salt to yield a hexapeptide.

53. The method according to claim 50, further comprising subjecting the tetrapeptide to an acid treatment to yield a tetrapeptide salt and reacting the tetrapeptide salt with a tetrapeptide acid to yield an octapeptide.

54. A method as claimed in claim 48, wherein the C-linked carbo β-amino acid ester is an (S) amino acid ester or an (R) amino acid ester.

55. A method as claimed in claim 48, wherein the alkaline treatment in step (b) is carried out on an (S) N-Boc C-linked carbo β-amino acid ester or an (R) N-Boc C-linked carbo β-amino acid ester.

56. A method as claimed in claim 48, comprising
   (a) reacting an (S) C-linked carbo β-amino acid with an (S) C-linked carbo β-amino acid ester salt to give an SS dipeptide; or
   (b) reacting (S) C-linked carbo β-amino acid with (R) C-linked carbo β-amino acid ester salt to give SR dipeptide; or
   (c) reacting (R) C-linked carbo β-amino acid with (R) C-linked carbo β-amino acid ester salt to give RR dipeptide; or
   (d) reacting (R) C-linked carbo β-amino acid with (S) C-linked carbo β-amino acid ester salt to give RS dipeptide; or
   (e) reacting (S) C-linked carbo β-amino acid with a β-Alanine ester salt to give C-linked carbo β-amino acid-β-Alanine mixed dipeptide.

57. A method as claimed in claim 49, wherein the alkaline treatment in step (e) is carried out on an
   a) SS dipeptide to give SS dipeptide acid; or
   b) SR dipeptide to give SR dipeptide acid; or
   c) RR dipeptide to give RR dipeptide acid; or
   d) RS dipeptide to give RS dipeptide acid.

58. A method as claimed in claim 50, wherein the acid treatment in step (f) is carried out on an
   a) SS dipeptide to give SS dipeptide salt; or
   b) SR dipeptide to give SR dipeptide salt; or
   c) RR dipeptide to give RR dipeptide salt; or
   d) RS dipeptide to give RS dipeptide salt.

59. A method as claimed in claim 51, wherein the tripeptide is formed by reacting
   a) an SS dipeptide acid with C-linked carbo β-amino acid ester (S) amine salt; or
   b) SR dipeptide acid with C-linked carbo β-amino acid ester (S) amine salt.

60. A method as claimed in claim 50, wherein the tetrapeptide is formed by reacting an
   a) SS dipeptide acid and SS dipeptide amine salt to give SSSS tetrapeptide; or
   b) SR dipeptide acid and SR dipeptide amine salt to give SRSR tetrapeptide; or
   c) RR dipeptide acid and RR dipeptide amine salt to give RRRR tetrapeptide; or
   d) RS dipeptide acid and RS dipeptide amine salt to give RSRS tetrapeptide; or
   e) RS dipeptide acid and SR dipeptide amine salt to give RSSR tetrapeptide; or
   f) SR dipeptide acid and RS dipeptide amine salt to give SRRS tetrapeptide; or
   g) mixed dipeptide acid and mixed dipeptide salt to give mixed tetrapeptide.

61. A method as claimed in claim 52, wherein the alkaline treatment of the tetrapeptide is carried out on
   a) SSSS tetrapeptide to give SSSS tetrapeptide acid; or
   b) SRSR tetrapeptide to give SRSR tetrapeptide acid; or
   c) RRRR tetrapeptide to give RRRR tetrapeptide acid; or
   d) RSRS tetrapeptide to give RSRS tetrapeptide acid; or
   e) S-β-alanineS-β-alanine mixed tetrapeptide to obtain a corresponding acid.

62. A method as claimed in claim 53, wherein the acid treatment of the tetrapeptide is carried out on
   a) SSSS tetrapeptide to give SSSS tetrapeptide amine salt; or
   b) SRSR tetrapeptide to give SRSR tetrapeptide amine salt; or
   c) RRRR tetrapeptide to give RRRR tetrapeptide amine salt; or
   d) RSRS tetrapeptide to give RSRS tetrapeptide amine salt; or
   e) mixed tetrapeptides to give mixed tetrapeptide amine salt.

63. A method as claimed in claim 52, wherein the hexapeptide is prepared by reacting
   a) SSSS tetrapeptide acid and SS dipeptide amine salt to give SSSSSS hexapeptide; or
   b) SRSR tetrapeptide acid and SR dipeptide amine salt to give SRSRSR hexapeptide; or
   c) RRRR tetrapeptide acid and RR dipeptide amine salt to give RRRRRR hexapeptide; or
   d) RSRS tetrapeptide acid and RS dipeptide amine salt to give RSRSRS hexapeptide; or
   e) mixed tetrapeptide acid and mixed dipeptide amine salt to give mixed hexapeptide.

64. A method as claimed in claim 53, wherein the octapeptide is prepared by reacting
   a) SSSS tetrapeptide acid and SSSS tetrapeptide amine salt to give octapeptide; or
   b) SRSR tetrapeptide acid and SRSR tetrapeptide amine salt to give octapeptide; or c) RRRR tetrapeptide acid and RRRR tetrapeptide amine salt to give octapeptide; or
d) RSRS tetrapeptide acid and RSSS tetrapeptide amine salt to give octapeptide.

65. A method as claimed in claim 48, wherein the C-linked β-peptide is of the formula

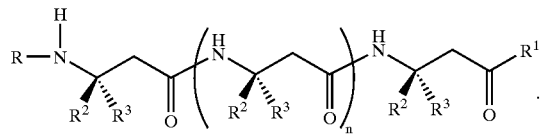

66. A method for preparation of the C-linked β-peptide compound of claim 1, comprising
a) reacting a C-linked carbo β-amino acid ester with Pd—C and exposing it to (Boc)$_2$ to give N-Boc C-linked β-amino acid ester; and
b) subjecting the N-Boc C-linked carbo β-amino acid ester obtained in step (a) to an acid treatment to give a salt of C-linked β-amino acid ester.

67. The method according to claim 66, wherein the acid treatment in step (b) is carried out on a (S) N-Boc C-linked carbo β-amino acid ester or (R) N-Boc C-linked carbo β-amino acid ester.

* * * * *